US008084605B2

(12) United States Patent
Kelly et al.

(10) Patent No.: US 8,084,605 B2
(45) Date of Patent: Dec. 27, 2011

(54) POLYMORPHS OF SUCCINATE SALT OF 2-[6-(3-AMINO-PIPERIDIN-1-YL)-3-METHYL-2,4-DIOXO-3,4-DIHYDRO-2H-PYRIMIDIN-1-YLMETHY]-4-FLUOR-BENZONITRILE AND METHODS OF USE THEREFOR

(76) Inventors: Ron C. Kelly, San Mateo, CA (US); Lien H. Koztecki, Indianapolis, IN (US)

( * ) Notice: Subject to any disclaimer, the term of this patent is extended or adjusted under 35 U.S.C. 154(b) by 764 days.

(21) Appl. No.: 11/947,635

(22) Filed: Nov. 29, 2007

(65) Prior Publication Data

US 2008/0280931 A1 Nov. 13, 2008

Related U.S. Application Data

(60) Provisional application No. 60/867,764, filed on Nov. 29, 2006.

(51) Int. Cl.
*C07D 401/04* (2006.01)
*A61K 31/506* (2006.01)
*A61P 19/02* (2006.01)
*A61P 3/10* (2006.01)
*A61P 35/00* (2006.01)

(52) U.S. Cl. ........................ 544/309; 514/274
(58) Field of Classification Search .................. 544/309; 514/274
See application file for complete search history.

(56) References Cited

U.S. PATENT DOCUMENTS

| | | | |
|---|---|---|---|
| 3,322,756 A | 5/1967 | Hilmer et al. |
| 3,544,570 A | 12/1970 | Timmler et al. |
| 3,823,135 A | 7/1974 | Pilgram et al. |
| 3,960,949 A | 6/1976 | Ahrens et al. |
| 4,494,978 A | 1/1985 | Chan |
| 4,687,777 A | 8/1987 | Meguro et al. |
| 4,935,493 A | 6/1990 | Bachovchin et al. |
| 5,002,953 A | 3/1991 | Hindley |
| 5,366,862 A | 11/1994 | Venton et al. |
| 5,387,512 A | 2/1995 | Balani et al. |
| 5,433,955 A | 7/1995 | Bredehorst et al. |
| 5,462,928 A | 10/1995 | Bachovchin et al. |
| 5,512,549 A | 4/1996 | Chen et al. |
| 5,543,396 A | 8/1996 | Powers et al. |
| 5,580,979 A | 12/1996 | Bachovchin |
| 5,601,986 A | 2/1997 | Takacs |
| 5,614,379 A | 3/1997 | MacKellar |
| 5,614,492 A | 3/1997 | Habener |
| 5,624,894 A | 4/1997 | Bodor |
| 5,798,344 A | 8/1998 | Kuroki et al. |
| 5,811,278 A | 9/1998 | Okamura et al. |
| 5,811,281 A | 9/1998 | Quaroni et al. |
| 5,814,460 A | 9/1998 | Venton et al. |
| 5,885,997 A | 3/1999 | Lohray et al. |
| 5,939,560 A | 8/1999 | Jenkins et al. |
| 5,965,532 A | 10/1999 | Bachovchin |
| 5,985,884 A | 11/1999 | Lohray et al. |
| 6,006,753 A | 12/1999 | Efendic |
| 6,011,155 A | 1/2000 | Villhauer |
| 6,090,786 A | 7/2000 | Augustyns et al. |
| 6,107,317 A | 8/2000 | Villhauer |
| 6,110,949 A | 8/2000 | Villhauer |
| 6,124,305 A | 9/2000 | Villhauer |
| 6,129,911 A | 10/2000 | Faris |
| 6,156,739 A | 12/2000 | Griffin et al. |
| 6,166,063 A | 12/2000 | Villhauer |
| 6,172,081 B1 | 1/2001 | Damon |
| 6,184,020 B1 | 2/2001 | Blinkovsky et al. |
| 6,201,132 B1 | 3/2001 | Jenkins et al. |
| 6,214,340 B1 | 4/2001 | Takeuchi et al. |
| 6,235,493 B1 | 5/2001 | Bissell et al. |

(Continued)

FOREIGN PATENT DOCUMENTS

DE 2150686 A1 4/1973

(Continued)

OTHER PUBLICATIONS

Mukkerjee, Sucharita "[2+2] versus [4+2] cycloaddition reactions of 1,3-diaza-1,3-butadienes with various mono and disubtituted ketenes and supporting mechanistic considerations" HeterOcycles, vol. 47, No. 2, 1998 XP001539476.
Noguchi, Michihiko "Generation of NH-azomethine imine intermediates through the 1,2-hydrogen shift of hydrazones and their intermolecular cycloaddition reaction with olefinic dipolarophiles" Tetrahedron vol. 59 (2003), p. 4123-3.
Abdel-Fattah et al. Indian Journal of Heterocyclic Chemistry (1999), 8(3), 177-182. (Abstract, 2 pages).
Abdel-Rahman, R. M.: Synthesis of some new fluorine bearing trisubstituted 3-thioxo-1, 2, 4-triazin-5-ones as potential anticancer agents: Farmaco, Edizione Scientifica, Societa Chimica Italiana, Pavia, IT, vol. 47, No. 3 (Mar. 1992), pp. 319-326, XP008000322.

(Continued)

*Primary Examiner* — Venkataraman Balasubramanian
(74) *Attorney, Agent, or Firm* — Mitchell R. Brustein

(57) ABSTRACT

Compositions comprising the succinate salt of 2-[6-(3-Amino-piperidin-1-yl)-3-methyl-2,4-dioxo-3,4-dihydro-2H-pyrimidin-1-ylmethyl]-4-fluoro-benzonitrile (referred to herein as Compound I) which has the formula:

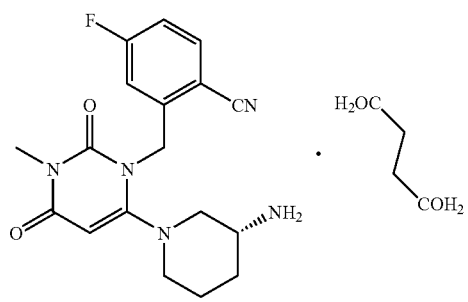

wherein the Compound I is present in one or more polymorphic forms. Also provided are novel methods for the preparation of the polymorphs of Compound I, and kits and articles of manufacture of the compositions, and methods of using the compositions to treat various diseases.

77 Claims, 37 Drawing Sheets

U.S. PATENT DOCUMENTS

| | | |
|---|---|---|
| 6,251,391 B1 | 6/2001 | Wilkinson et al. |
| 6,258,597 B1 | 7/2001 | Bachovchin |
| 6,261,794 B1 | 7/2001 | Chang |
| 6,265,551 B1 | 7/2001 | Duke-Cohan et al. |
| 6,303,661 B1 | 10/2001 | Demuth et al. |
| 6,309,868 B1 | 10/2001 | Monod |
| 6,310,069 B1 | 10/2001 | Lohray et al. |
| 6,319,893 B1 | 11/2001 | Demuth et al. |
| 6,325,989 B1 | 12/2001 | Duke-Cohan et al. |
| 6,335,429 B1 | 1/2002 | Cai et al. |
| 6,337,069 B1 | 1/2002 | Grouzmann et al. |
| 6,342,611 B1 | 1/2002 | Weber et al. |
| 6,355,614 B1 | 3/2002 | Wallner |
| 6,380,398 B2 | 4/2002 | Kanstrup et al. |
| 6,395,767 B2 | 5/2002 | Robl et al. |
| 6,432,969 B1 | 8/2002 | Villhauer |
| 6,447,772 B1 | 9/2002 | Houston |
| 6,448,045 B1 | 9/2002 | Levine et al. |
| 6,458,924 B2 | 10/2002 | Knudsen et al. |
| 6,485,955 B1 | 11/2002 | Huber et al. |
| 6,495,544 B2 | 12/2002 | Hansen, Jr. et al. |
| 6,518,277 B1 | 2/2003 | Sadhu et al. |
| 6,521,644 B1 | 2/2003 | Broqua |
| 6,528,486 B1 | 3/2003 | Larsen et al. |
| 6,545,170 B2 | 4/2003 | Pitzele et al. |
| 6,548,481 B1 | 4/2003 | Demuth et al. |
| 6,548,529 B1 | 4/2003 | Robl et al. |
| 6,555,519 B2 | 4/2003 | Washburn |
| 6,555,521 B2 | 4/2003 | Hermeling et al. |
| 6,559,188 B1 | 5/2003 | Gatlin et al. |
| 6,573,096 B1 | 6/2003 | Chen |
| 6,573,287 B2 | 6/2003 | Sulsky et al. |
| 6,586,198 B2 | 7/2003 | Brown |
| 6,608,038 B2 | 8/2003 | Caplan et al. |
| 6,617,340 B1 | 9/2003 | Villhauer |
| 6,620,821 B2 | 9/2003 | Robl |
| 6,620,910 B1 | 9/2003 | Calas et al. |
| 6,627,636 B2 | 9/2003 | Robl |
| 6,645,995 B2 | 11/2003 | Kanstrup et al. |
| 6,664,273 B2 | 12/2003 | Burnett et al. |
| 6,673,815 B2 | 1/2004 | Devasthale et al. |
| 6,673,829 B2 | 1/2004 | Dorwald et al. |
| 6,686,337 B2 | 2/2004 | Connor |
| 6,699,871 B2 | 3/2004 | Edmondson et al. |
| 6,703,238 B2 | 3/2004 | Bachovchin |
| 6,706,742 B2 | 3/2004 | De Nanteuil et al. |
| 6,710,040 B1 | 3/2004 | Hulin et al. |
| 6,716,843 B2 | 4/2004 | De Nanteuil et al. |
| 6,727,261 B2 | 4/2004 | Gobbi et al. |
| 6,727,271 B2 | 4/2004 | Cheng et al. |
| 6,747,035 B2 | 6/2004 | Guadilliere et al. |
| 6,800,650 B2 | 10/2004 | Boehringer et al. |
| 6,803,357 B1 | 10/2004 | Bachovchin et al. |
| 6,825,169 B1 | 11/2004 | Bachovchin et al. |
| 6,861,440 B2 | 3/2005 | Boehringer et al. |
| 6,867,205 B2 | 3/2005 | Boehringer et al. |
| 6,998,502 B1 | 2/2006 | Majeed et al. |
| 7,230,000 B1 | 6/2007 | Finer et al. |
| 7,304,086 B2 | 12/2007 | Schilling et al. |
| 7,371,871 B2 | 5/2008 | Schilling et al. |
| 7,470,700 B2 | 12/2008 | Feng et al. |
| 7,781,584 B2 * | 8/2010 | Feng et al. .................. 544/309 |
| 7,795,428 B2 * | 9/2010 | Feng et al. .................. 544/309 |
| 2001/0018210 A1 | 8/2001 | Bachovchin et al. |
| 2001/0020006 A1 | 9/2001 | Demuth et al. |
| 2001/0031780 A1 | 10/2001 | Kanstrup et al. |
| 2001/0047078 A1 | 11/2001 | Chang |
| 2001/0051646 A1 | 12/2001 | Demuth et al. |
| 2002/0006899 A1 | 1/2002 | Pospisilik et al. |
| 2002/0016100 A1 | 2/2002 | Okabe et al. |
| 2002/0019411 A1 | 2/2002 | Robl et al. |
| 2002/0037829 A1 | 3/2002 | Aronson et al. |
| 2002/0041871 A1 | 4/2002 | Brudnak |
| 2002/0049153 A1 | 4/2002 | Bridon et al. |
| 2002/0049164 A1 | 4/2002 | Demuth et al. |
| 2002/0061839 A1 | 5/2002 | Scharpe et al. |
| 2002/0071838 A1 | 6/2002 | Demuth et al. |
| 2002/0077340 A1 | 6/2002 | Sulsky et al. |
| 2002/0082292 A1 | 6/2002 | Sahoo et al. |
| 2002/0082427 A1 | 6/2002 | Demuth et al. |
| 2002/0103242 A1 | 8/2002 | Sahoo et al. |
| 2002/0103384 A1 | 8/2002 | Kanstrup et al. |
| 2002/0110560 A1 | 8/2002 | Demuth et al. |
| 2002/0115843 A1 | 8/2002 | Oi et al. |
| 2002/0132979 A1 | 9/2002 | Chen |
| 2002/0147130 A1 | 10/2002 | Huber et al. |
| 2002/0147157 A1 | 10/2002 | Connor |
| 2002/0155565 A1 | 10/2002 | Garin-Chesa et al. |
| 2002/0164759 A1 | 11/2002 | Travis et al. |
| 2002/0165164 A1 | 11/2002 | Demuth et al. |
| 2002/0169159 A1 | 11/2002 | Medina et al. |
| 2002/0183367 A1 | 12/2002 | Sulsky et al. |
| 2002/0193390 A1 | 12/2002 | Villhauer |
| 2002/0198205 A1 | 12/2002 | Himmelsbach et al. |
| 2002/0198242 A1 | 12/2002 | Demuth et al. |
| 2002/0198380 A1 | 12/2002 | Belzer et al. |
| 2003/0008905 A1 | 1/2003 | Demuth et al. |
| 2003/0008925 A1 | 1/2003 | Esteve et al. |
| 2003/0027282 A1 | 2/2003 | Huber et al. |
| 2003/0040478 A1 | 2/2003 | Drucker et al. |
| 2003/0045464 A1 | 3/2003 | Hermeling et al. |
| 2003/0055052 A1 | 3/2003 | Peters et al. |
| 2003/0060412 A1 | 3/2003 | Prouty et al. |
| 2003/0060434 A1 | 3/2003 | Nielsen et al. |
| 2003/0069234 A1 | 4/2003 | Medina et al. |
| 2003/0087935 A1 | 5/2003 | Cheng et al. |
| 2003/0087950 A1 | 5/2003 | DeNanteuil et al. |
| 2003/0089935 A1 | 5/2003 | Fan et al. |
| 2003/0092630 A2 | 5/2003 | Demuth et al. |
| 2003/0092697 A1 | 5/2003 | Cheng et al. |
| 2003/0096846 A1 | 5/2003 | Cheng et al. |
| 2003/0096857 A1 | 5/2003 | Evans |
| 2003/0100563 A1 | 5/2003 | Edmondson et al. |
| 2003/0103968 A1 | 6/2003 | Amelsberg et al. |
| 2003/0105077 A1 | 6/2003 | Kanstrup et al. |
| 2003/0119736 A1 | 6/2003 | Demuth et al. |
| 2003/0119738 A1 | 6/2003 | Niestroj et al. |
| 2003/0119750 A1 | 6/2003 | Demuth et al. |
| 2003/0125304 A1 | 7/2003 | Demuth et al. |
| 2003/0130199 A1 | 7/2003 | von Hoersten et al. |
| 2003/0130281 A1 | 7/2003 | Boehringer et al. |
| 2003/0130306 A1 | 7/2003 | Devasthale et al. |
| 2003/0134802 A1 | 7/2003 | Demuth et al. |
| 2003/0135023 A1 | 7/2003 | Demuth et al. |
| 2003/0139429 A1 | 7/2003 | Cohen |
| 2003/0139434 A1 | 7/2003 | Balkan et al. |
| 2003/0144206 A1 | 7/2003 | Knudsen et al. |
| 2003/0148961 A1 | 8/2003 | Heiser et al. |
| 2003/0149071 A1 | 8/2003 | Gobbi et al. |
| 2003/0153509 A1 | 8/2003 | Bachovchin et al. |
| 2003/0162820 A1 | 8/2003 | Demuth et al. |
| 2003/0166578 A1 | 9/2003 | Arch et al. |
| 2003/0166662 A1 | 9/2003 | Fryburg et al. |
| 2003/0166690 A1 | 9/2003 | Ebdrup et al. |
| 2003/0171358 A1 | 9/2003 | Jeppesen et al. |
| 2003/0171411 A1 | 9/2003 | Kodra et al. |
| 2003/0176357 A1 | 9/2003 | Pospisilik et al. |
| 2003/0181497 A1 | 9/2003 | Chen et al. |
| 2003/0186963 A1 | 10/2003 | Dorwald et al. |
| 2003/0187254 A1 | 10/2003 | Perry et al. |
| 2003/0191112 A1 | 10/2003 | Dorwald et al. |
| 2003/0195188 A1 | 10/2003 | Boehringer et al. |
| 2003/0195190 A1 | 10/2003 | Peschke et al. |
| 2003/0199451 A1 | 10/2003 | Mogensen et al. |
| 2003/0199528 A1 | 10/2003 | Kanstrup et al. |
| 2003/0199563 A1 | 10/2003 | Robl et al. |
| 2003/0199672 A1 | 10/2003 | Knudsen et al. |
| 2003/0203946 A1 | 10/2003 | Behrens et al. |
| 2003/0216382 A1 | 11/2003 | Boehringer et al. |
| 2003/0216450 A1 | 11/2003 | Evans et al. |
| 2003/0220345 A1 | 11/2003 | Hamby et al. |
| 2003/0225102 A1 | 12/2003 | Sankaranarayanan |
| 2003/0232761 A1 | 12/2003 | Hinke et al. |
| 2003/0236272 A1 | 12/2003 | Carr |
| 2004/0002495 A1 | 1/2004 | Sher et al. |
| 2004/0002609 A1 | 1/2004 | Hulin |
| 2004/0006062 A1 | 1/2004 | Smallheer et al. |

| | | |
|---|---|---|
| 2004/0009972 A1 | 1/2004 | Ding et al. |
| 2004/0009998 A1 | 1/2004 | Dhar et al. |
| 2004/0034014 A1 | 2/2004 | Kanstrup et al. |
| 2004/0053369 A1 | 3/2004 | Abbott et al. |
| 2004/0054171 A1 | 3/2004 | Jensen et al. |
| 2004/0058876 A1 | 3/2004 | Hoffmann et al. |
| 2004/0063935 A1 | 4/2004 | Yasuda |
| 2004/0072874 A1 | 4/2004 | Sato et al. |
| 2004/0072892 A1 | 4/2004 | Fukushima et al. |
| 2004/0077645 A1 | 4/2004 | Himmelsbach et al. |
| 2004/0082497 A1 | 4/2004 | Evans et al. |
| 2004/0082607 A1 | 4/2004 | Oi et al. |
| 2004/0087587 A1 | 5/2004 | Himmelsbach et al. |
| 2004/0092478 A1 | 5/2004 | Rothermel et al. |
| 2004/0097510 A1 | 5/2004 | Himmelsbach et al. |
| 2004/0106655 A1 | 6/2004 | Kitajima et al. |
| 2004/0106656 A1 | 6/2004 | Ashton et al. |
| 2004/0106802 A1 | 6/2004 | Sankaranarayanan |
| 2004/0110817 A1 | 6/2004 | Hulin |
| 2004/0116328 A1 | 6/2004 | Yoshikawa et al. |
| 2004/0132713 A1 | 7/2004 | Hulin et al. |
| 2004/0132732 A1 | 7/2004 | Han et al. |
| 2004/0138148 A1 | 7/2004 | Fushimi et al. |
| 2004/0138214 A1 | 7/2004 | Himmelsbach et al. |
| 2004/0138215 A1 | 7/2004 | Eckhardt et al. |
| 2004/0147434 A1 | 7/2004 | Ansorge et al. |
| 2004/0152192 A1 | 8/2004 | Bachovchin et al. |
| 2004/0152745 A1 | 8/2004 | Jackson et al. |
| 2004/0166125 A1 | 8/2004 | Himmelsbach et al. |
| 2004/0167133 A1 | 8/2004 | Edmondson et al. |
| 2004/0167191 A1 | 8/2004 | Demuth et al. |
| 2004/0167341 A1 | 8/2004 | Haffner et al. |
| 2004/0171104 A1 | 9/2004 | Blinkovsky et al. |
| 2004/0171555 A1 | 9/2004 | Demuth et al. |
| 2004/0171848 A1 | 9/2004 | Haffner et al. |
| 2004/0176406 A1 | 9/2004 | Gobbi et al. |
| 2004/0176428 A1 | 9/2004 | Edmondson et al. |
| 2004/0180925 A1 | 9/2004 | Matsuno et al. |
| 2004/0186153 A1 | 9/2004 | Yasuda et al. |
| 2004/0198786 A1 | 10/2004 | Gretzke et al. |
| 2004/0209891 A1 | 10/2004 | Broqua et al. |
| 2004/0229820 A1 | 11/2004 | Bachovchin et al. |
| 2004/0229848 A1 | 11/2004 | Demuth et al. |
| 2004/0236102 A1 | 11/2004 | Brockunier et al. |
| 2004/0242566 A1 | 12/2004 | Feng et al. |
| 2004/0242568 A1 | 12/2004 | Feng et al. |
| 2004/0242636 A1 | 12/2004 | Haffner et al. |
| 2004/0242898 A1 | 12/2004 | Hulin et al. |
| 2004/0254167 A1 | 12/2004 | Biftu et al. |
| 2004/0254226 A1 | 12/2004 | Feng et al. |
| 2004/0259843 A1 | 12/2004 | Madar et al. |
| 2004/0259870 A1 | 12/2004 | Feng et al. |
| 2004/0259883 A1 | 12/2004 | Sakashita et al. |
| 2004/0259902 A1 | 12/2004 | Boehringer et al. |
| 2004/0259903 A1 | 12/2004 | Boehringer et al. |
| 2004/0259919 A1 | 12/2004 | Magnin et al. |
| 2005/0004117 A1 | 1/2005 | Feng et al. |
| 2005/0014732 A1 | 1/2005 | Gulve et al. |
| 2005/0014946 A1 | 1/2005 | Demuth et al. |
| 2005/0020574 A1 | 1/2005 | Hauel et al. |
| 2005/0026921 A1 | 2/2005 | Eckhardt et al. |
| 2005/0032804 A1 | 2/2005 | Cypes et al. |
| 2005/0038020 A1 | 2/2005 | Hamann et al. |
| 2005/0043292 A1 | 2/2005 | Parker et al. |
| 2005/0043299 A1 | 2/2005 | Evans et al. |
| 2005/0058635 A1 | 3/2005 | Demuth et al. |
| 2005/0065144 A1 | 3/2005 | Feng et al. |
| 2005/0065145 A1 | 3/2005 | Cao |
| 2005/0065148 A1 | 3/2005 | Feng et al. |
| 2005/0070530 A1 | 3/2005 | Feng et al. |
| 2005/0070531 A1 | 3/2005 | Feng et al. |
| 2005/0070535 A1 | 3/2005 | Feng et al. |
| 2005/0070706 A1 | 3/2005 | Feng et al. |
| 2005/0075330 A1 | 4/2005 | Feng et al. |
| 2005/0261271 A1* | 11/2005 | Feng et al. ................. 514/210.2 |
| 2006/0135767 A1 | 6/2006 | Feng et al. |
| 2007/0060528 A1 | 3/2007 | Christopher et al. |
| 2007/0060529 A1 | 3/2007 | Christopher et al. |
| 2007/0060530 A1 | 3/2007 | Christopher et al. |
| 2007/0066635 A1 | 3/2007 | Andres et al. |
| 2008/0003283 A1* | 1/2008 | Feng et al. .................... 424/464 |
| 2008/0108807 A1* | 5/2008 | Feng et al. .................... 540/601 |
| 2008/0108808 A1* | 5/2008 | Feng et al. .................... 540/601 |
| 2008/0177064 A1* | 7/2008 | Feng et al. .................... 540/601 |
| 2008/0188501 A1* | 8/2008 | Feng et al. .................... 514/274 |
| 2009/0012059 A1* | 1/2009 | Feng et al. ................ 514/217.06 |

FOREIGN PATENT DOCUMENTS

| | | |
|---|---|---|
| DE | 2361551 A1 | 6/1975 |
| DE | 2500024 A1 | 7/1976 |
| DE | 2801289 A1 | 5/1979 |
| DE | 10256264 A | 6/2004 |
| EP | 0354549 | 2/1900 |
| EP | 0378255 A2 | 7/1990 |
| EP | 0378991 A1 | 7/1990 |
| EP | 0442473 A1 | 8/1991 |
| EP | 0505893 A1 | 9/1992 |
| EP | 0547442 A1 | 6/1993 |
| EP | 0547514 | 6/1993 |
| EP | 0574846 | 12/1993 |
| EP | 0587377 A2 | 3/1994 |
| EP | 0657452 | 6/1995 |
| EP | 0702013 | 3/1996 |
| EP | 0748800 | 12/1996 |
| EP | 0570594 | 7/1997 |
| EP | 0847992 | 6/1998 |
| EP | 0900566 A2 | 3/1999 |
| EP | 0900568 A2 | 3/1999 |
| EP | 1136482 A1 | 9/2001 |
| EP | 1197799 A1 | 4/2002 |
| EP | 1229024 | 8/2002 |
| EP | 1398032 A1 | 3/2004 |
| EP | 1532980 A1 | 5/2005 |
| EP | 1586571 A1 | 10/2005 |
| FR | 2162106 A1 | 11/1972 |
| GB | 699812 | 11/1953 |
| GB | 1377642 | 12/1974 |
| GB | 1441665 A | 7/1976 |
| GB | 1464248 A | 2/1977 |
| GB | 2143542 A | 9/1986 |
| GB | 2230527 A | 10/1990 |
| JP | 9295977 | 11/1997 |
| JP | 2002/338466 | 11/2002 |
| JP | 2003/128551 | 5/2003 |
| JP | 2004/099600 A | 4/2004 |
| JP | 2004/123738 A | 4/2004 |
| WO | WO 89/10701 A1 | 11/1989 |
| WO | WO 91/11457 A1 | 8/1991 |
| WO | WO 91/12001 A1 | 8/1991 |
| WO | WO 93/21162 A2 | 1/1993 |
| WO | WO 93/08259 A2 | 4/1993 |
| WO | WO 93/24634 A1 | 12/1993 |
| WO | WO 94/03055 A1 | 2/1994 |
| WO | WO 95/15309 A1 | 6/1995 |
| WO | WO 95/29691 A1 | 11/1995 |
| WO | WO 95/35031 A1 | 12/1995 |
| WO | WO 96/02667 A1 | 2/1996 |
| WO | WO 96/32384 A1 | 10/1996 |
| WO | WO 96/38550 A1 | 12/1996 |
| WO | WO 97/29776 A1 | 8/1997 |
| WO | WO 97/40832 A1 | 11/1997 |
| WO | WO 98/00439 A2 | 1/1998 |
| WO | WO 98/18763 A1 | 5/1998 |
| WO | WO 98/19998 A2 | 5/1998 |
| WO | WO 98/24780 A2 | 6/1998 |
| WO | WO 98/50046 A1 | 11/1998 |
| WO | WO 98/51803 A1 | 11/1998 |
| WO | WO 99/02705 A1 | 1/1999 |
| WO | WO 99/16864 A1 | 4/1999 |
| WO | WO 99/17799 A1 | 4/1999 |
| WO | WO 99/18856 A1 | 4/1999 |
| WO | WO 99/28474 A2 | 6/1999 |
| WO | WO 99/38501 C2 | 8/1999 |
| WO | WO 99/46272 A1 | 9/1999 |
| WO | WO 99/47152 A1 | 9/1999 |
| WO | WO 99/50249 A2 | 10/1999 |
| WO | WO 99/52893 | 10/1999 |
| WO | WO 99/61431 A1 | 12/1999 |

| | | | | | | |
|---|---|---|---|---|---|---|
| WO | WO 99/62914 A1 | 12/1999 | | WO | WO 03/010197 A2 | 2/2003 |
| WO | WO 99/67278 A1 | 12/1999 | | WO | WO 03/010314 A2 | 2/2003 |
| WO | WO 99/67279 A1 | 12/1999 | | WO | WO 03/011807 A1 | 2/2003 |
| WO | WO 00/07617 A1 | 2/2000 | | WO | WO 03/011814 A1 | 2/2003 |
| WO | WO 00/09666 A2 | 2/2000 | | WO | WO 03/011892 A2 | 2/2003 |
| WO | WO 00/10549 A1 | 3/2000 | | WO | WO 03/014318 A2 | 2/2003 |
| WO | WO 00/15211 A2 | 3/2000 | | WO | WO 03/015775 A1 | 2/2003 |
| WO | WO 00/20416 A1 | 4/2000 | | WO | WO 03/016335 A2 | 2/2003 |
| WO | WO 00/76986 A1 | 4/2000 | | WO | WO 03/017936 A2 | 3/2003 |
| WO | WO 00/34241 A1 | 6/2000 | | WO | WO 03/022871 A2 | 3/2003 |
| WO | WO 00/40583 A2 | 7/2000 | | WO | WO 03/024942 A1 | 3/2003 |
| WO | WO 00/43366 A1 | 7/2000 | | WO | WO 03/024965 A2 | 3/2003 |
| WO | WO 00/47219 A2 | 8/2000 | | WO | WO 03/053330 A2 | 3/2003 |
| WO | WO 00/53171 A1 | 9/2000 | | WO | WO 03/026652 A1 | 4/2003 |
| WO | WO 00/56296 A2 | 9/2000 | | WO | WO 03/027080 A1 | 4/2003 |
| WO | WO 00/56297 A2 | 9/2000 | | WO | WO 03/030946 A1 | 4/2003 |
| WO | WO 00/57721 A2 | 10/2000 | | WO | WO 03/033524 A2 | 4/2003 |
| WO | WO 01/14318 A2 | 3/2001 | | WO | WO 03/033671 A2 | 4/2003 |
| WO | WO 01/16301 A1 | 3/2001 | | WO | WO 03/035057 A1 | 5/2003 |
| WO | WO 01/19866 A1 | 3/2001 | | WO | WO 03/035067 A1 | 5/2003 |
| WO | WO 01/23364 A1 | 4/2001 | | WO | WO 03/035640 A1 | 5/2003 |
| WO | WO 01/34594 A1 | 5/2001 | | WO | WO 03/037327 A1 | 5/2003 |
| WO | WO 01/40180 A2 | 6/2001 | | WO | WO 03/037888 A1 | 5/2003 |
| WO | WO 01/52825 A2 | 7/2001 | | WO | WO 03/038123 A2 | 5/2003 |
| WO | WO 01/55105 A1 | 8/2001 | | WO | WO 03/040114 A1 | 5/2003 |
| WO | WO 01/55119 A2 | 8/2001 | | WO | WO 03/040174 A2 | 5/2003 |
| WO | WO 01/56988 A1 | 8/2001 | | WO | WO 03/045228 A2 | 6/2003 |
| WO | WO 01/62266 A2 | 8/2001 | | WO | WO 03/045977 A2 | 6/2003 |
| WO | WO 01/68603 A2 | 9/2001 | | WO | WO 03/048081 A2 | 6/2003 |
| WO | WO 01/70675 A2 | 9/2001 | | WO | WO 03/048158 A1 | 6/2003 |
| WO | WO 01/70729 A1 | 9/2001 | | WO | WO 03/051848 A2 | 6/2003 |
| WO | WO 01/72290 A2 | 10/2001 | | WO | WO 03/055881 A1 | 7/2003 |
| WO | WO 01/74299 A2 | 10/2001 | | WO | WO 03/057144 A2 | 7/2003 |
| WO | WO 01/79206 A1 | 10/2001 | | WO | WO 03/057200 A1 | 7/2003 |
| WO | WO 01/81304 A1 | 11/2001 | | WO | WO 03/057666 A2 | 7/2003 |
| WO | WO 01/81337 A1 | 11/2001 | | WO | WO 03/063903 A2 | 8/2003 |
| WO | WO 01/89569 A1 | 11/2001 | | WO | WO 03/065983 A2 | 8/2003 |
| WO | WO 01/94597 A1 | 12/2001 | | WO | WO 03/068748 A1 | 8/2003 |
| WO | WO 01/96295 A2 | 12/2001 | | WO | WO 03/068757 A1 | 8/2003 |
| WO | WO 01/97808 A1 | 12/2001 | | WO | WO 03/072197 A1 | 9/2003 |
| WO | WO 02/02560 A2 | 1/2002 | | WO | WO 03/072556 A1 | 9/2003 |
| WO | WO 02/04610 A2 | 1/2002 | | WO | WO 03/074500 A2 | 9/2003 |
| WO | WO 02/08931 A1 | 1/2002 | | WO | WO 03/076393 A1 | 9/2003 |
| WO | WO 02/09716 A2 | 2/2002 | | WO | WO 03/076414 A2 | 9/2003 |
| WO | WO 02/14271 A1 | 2/2002 | | WO | WO 03/076418 A1 | 9/2003 |
| WO | WO 02/20488 A2 | 3/2002 | | WO | WO 03/077935 A1 | 9/2003 |
| WO | WO 02/20804 A1 | 3/2002 | | WO | WO 03/080070 A2 | 10/2003 |
| WO | WO 02/26703 A1 | 4/2002 | | WO | WO 03/080633 A1 | 10/2003 |
| WO | WO 02/28742 A1 | 4/2002 | | WO | WO 03/082817 A2 | 10/2003 |
| WO | WO 02/30890 A1 | 4/2002 | | WO | WO 03/082859 A1 | 10/2003 |
| WO | WO 02/30891 A1 | 4/2002 | | WO | WO 03/082898 A2 | 10/2003 |
| WO | WO 02/31134 A2 | 4/2002 | | WO | WO 03/084940 A1 | 10/2003 |
| WO | WO 02/34242 A2 | 5/2002 | | WO | WO 03/092605 A2 | 11/2003 |
| WO | WO 02/34900 A1 | 5/2002 | | WO | WO 03/099279 A1 | 12/2003 |
| WO | WO 02/38541 A1 | 5/2002 | | WO | WO 03/099286 A1 | 12/2003 |
| WO | WO 02/38742 A2 | 5/2002 | | WO | WO 03/099818 A1 | 12/2003 |
| WO | WO 02/051836 A1 | 7/2002 | | WO | WO 03/101449 A2 | 12/2003 |
| WO | WO 02/053170 A2 | 7/2002 | | WO | WO 03/101958 A2 | 12/2003 |
| WO | WO 02/059301 A1 | 8/2002 | | WO | WO 03/104207 A2 | 12/2003 |
| WO | WO 02/059343 A2 | 8/2002 | | WO | WO 03/104208 | 12/2003 |
| WO | WO 02/062764 C2 | 8/2002 | | WO | WO 03/104229 | 12/2003 |
| WO | WO 02/066627 A1 | 8/2002 | | WO | WO 03/106416 A2 | 12/2003 |
| WO | WO 02/068420 A1 | 9/2002 | | WO | WO 03/106456 A2 | 12/2003 |
| WO | WO 02/076450 A1 | 10/2002 | | WO | WO 2004/002535 A1 | 1/2004 |
| WO | WO 02/083109 A1 | 10/2002 | | WO | WO 2004/002986 A2 | 1/2004 |
| WO | WO 02/083128 A1 | 10/2002 | | WO | WO 2004/004655 A2 | 1/2004 |
| WO | WO 02/092127 A1 | 11/2002 | | WO | WO 2004/004661 A2 | 1/2004 |
| WO | WO 02/094178 A2 | 11/2002 | | WO | WO 2004/004665 A2 | 1/2004 |
| WO | WO 02/096357 A2 | 12/2002 | | WO | WO 2004/007446 | 1/2004 |
| WO | WO 03/000180 A2 | 1/2003 | | WO | WO 2004/007468 | 1/2004 |
| WO | WO 03/000181 A2 | 1/2003 | | WO | WO 2004/011640 | 2/2004 |
| WO | WO 03/000250 A1 | 1/2003 | | WO | WO 2004/014860 A2 | 2/2004 |
| WO | WO 03/002530 A2 | 1/2003 | | WO | WO 2004/017989 A1 | 3/2004 |
| WO | WO 03/002531 A2 | 1/2003 | | WO | WO 2004/018467 A2 | 3/2004 |
| WO | WO 03/002553 A2 | 1/2003 | | WO | WO 2004/018468 A2 | 3/2004 |
| WO | WO 03/002596 A2 | 1/2003 | | WO | WO 2004/018469 A1 | 3/2004 |
| WO | WO 03/004496 A1 | 1/2003 | | WO | WO 2004/020407 A1 | 3/2004 |
| WO | WO 03/004498 A1 | 1/2003 | | WO | WO 2004/024184 A1 | 3/2004 |
| WO | WO 03/007888 A2 | 1/2003 | | WO | WO 2004/026822 A2 | 4/2004 |

| WO | WO 2004/028524 A1 | 4/2004 |
| --- | --- | --- |
| WO | WO 2004/031175 A2 | 4/2004 |
| WO | WO 2004/031374 A2 | 4/2004 |
| WO | WO 2004/032836 A2 | 4/2004 |
| WO | WO 2004/032861 A2 | 4/2004 |
| WO | WO 2004/033455 A2 | 4/2004 |
| WO | WO 2004/037169 A2 | 5/2004 |
| WO | WO 2004/037176 A2 | 5/2004 |
| WO | WO 2004/037181 A2 | 5/2004 |
| WO | WO 2004/041795 A1 | 5/2004 |
| WO | WO 2004/043940 A1 | 5/2004 |
| WO | WO 2004/046106 A1 | 6/2004 |
| WO | WO 2004/048352 A2 | 6/2004 |
| WO | WO 2004/050022 A2 | 6/2004 |
| WO | WO 2004/050656 A1 | 6/2004 |
| WO | WO 2004/050658 A1 | 6/2004 |
| WO | WO 2004/052850 A2 | 6/2004 |
| WO | WO 2004/058266 A1 | 7/2004 |
| WO | WO 2004/062613 A2 | 7/2004 |
| WO | WO 2004/064778 A2 | 8/2004 |
| WO | WO 2004/067509 A1 | 8/2004 |
| WO | WO 2004/069162 A2 | 8/2004 |
| WO | WO 2004/071454 A2 | 8/2004 |
| WO | WO 2004/075815 A2 | 9/2004 |
| WO | WO 2004/075891 A1 | 9/2004 |
| WO | WO 2004/076401 A1 | 9/2004 |
| WO | WO 2004/076433 A1 | 9/2004 |
| WO | WO 2004/076434 A1 | 9/2004 |
| WO | WO 2004/078777 A2 | 9/2004 |
| WO | WO 2004/080958 A2 | 9/2004 |
| WO | WO 2004/082599 A2 | 9/2004 |
| WO | WO 2004/083212 A1 | 9/2004 |
| WO | WO 2004/085408 A1 | 10/2004 |
| WO | WO 2004/085661 A2 | 10/2004 |
| WO | WO 2004/087053 C2 | 10/2004 |
| WO | WO 2004/087650 A2 | 10/2004 |
| WO | WO 2004/087880 A2 | 10/2004 |
| WO | WO 2004/089362 A1 | 10/2004 |
| WO | WO 2004/096806 A1 | 11/2004 |
| WO | WO 2004/098625 A2 | 11/2004 |
| WO | WO 2004/099134 A2 | 11/2004 |
| WO | WO 2004/099185 A1 | 11/2004 |
| WO | WO 2004/101514 A1 | 11/2004 |
| WO | WO 2004/103276 A2 | 12/2004 |
| WO | WO 2004/103993 A1 | 12/2004 |
| WO | WO 2004/104215 A2 | 12/2004 |
| WO | WO 2004/104216 A2 | 12/2004 |
| WO | WO 2004/110436 A1 | 12/2004 |
| WO | WO 2004/111041 A1 | 12/2004 |
| WO | WO 2004/111051 A1 | 12/2004 |
| WO | WO 2004/112701 A2 | 12/2004 |
| WO | WO 2005/000846 A1 | 1/2005 |
| WO | WO 2005/000848 A1 | 1/2005 |
| WO | WO 2005/003135 A1 | 1/2005 |
| WO | WO 2005/004906 A2 | 1/2005 |
| WO | WO 2005/011581 A2 | 2/2005 |
| WO | WO 2005/012249 A2 | 2/2005 |
| WO | WO 2005/016911 A1 | 2/2005 |
| WO | WO 2005/019168 A2 | 3/2005 |
| WO | WO 2005/095381 A1 | 10/2005 |
| WO | WO 2007/033265 | 3/2007 |
| WO | WO 2007/033266 | 3/2007 |
| WO | WO 2007/033350 | 3/2007 |

OTHER PUBLICATIONS

Abstract of Barnela et al. HCAPLUS Accesssion No. 1987:138384 Indian Journal of Chemistry Section B: Organic Chemistry Including Medicinal Chemistry (1986), 25B(7), 709-11. (Abstract 2 pages).
Abstract of Barnickel et al. STN Printout (one page). Accession No. 1996:12269. Abstract of WO 06/23364.
Abstract of Lakhan et al. Journal of Indian Chemical Society (1987), 64 (5), 316-18 (2 pages).
Abstract of Shyam et al. Current Science (1975), 44(16), 572-4 (one page).
Abstract of Tiwari et al. Indian of Journal of Pharmaceutical Sciences (1978), 40(2), 40-3 (2 pages).
Abstract of Pattanaik et al. Indian Journal of Chemistry, Section B; Organic Chemistry including Medicinal Chemistry (1998), 37B (12), 1304-1306 from STN CAS online search printout (3 pages).

Akahoshi, F. et al.: "Synthesis and pharmacological activitey of □riazole[1,5-a]triazine derivatives inhibiting eosinophilia." Journal of Medicinal Chemistry, vol. 41, No. 16, (Jul. 30, 1998), pp. 2985-2993, XP002390903.
Alagarsamy, V. et al. "Synthesis and pharmacological investigation . . . " Pharmazie, vol. 57, No. 5 2002, pp. 306-307, XP008084498.
Algarsamy, V. et al. "Synthesis, analgesic, antii-inflammatory . . . " Bio & Pharm. Bulletin of Japan, Pharma society of JP, vol. 25, No. 11, 2002, pp. 1432-1435, XP008084513 ISSN: 0918-6158.
Argaud, Doriane et al., Metaformin decreases gluconeogenesis by enhancing the pyruvate kinase flux in isolated rat hepatocytes, European J. Biochem. 213, 1341-1348 (1993).
Ashcroft, Stephen J.H. et al., Structure-activity relationships of alloxan-like compounds derived from uric acid, Br. J. Pharmac. (1986), 89 pp. 469-472.
Bahaji E-H et al. Database Biosis [Online] Biosciences Information Service, Philadelphia, PA, US; 1991,: "Studies on Immunostimulating Derivatives Synthesis of Some Pyrrolo-1 2-C-Pyrimidines" XP002392081. Database accession No. PREV199192140000 abstract.
Baker, B.R. et al., Irreversible Enzyme Inhibitors. On the Mode of Pyrimidine Binding of 5-alkyl and 5-Arylpyrimidines to Dihydrofolic Reductase (1,2), Journal of Heterocyclic Chemistry vol. 4 (1967) pp. 39-48.
Bal, Gunther, Dipeptidyl Peptidase IV and Prolyl Oligopeptidase: Design, Synthesis and Evaluation of Substrates and Inhibitors, (2002) Universiteit Antwerpen.
Banker, G.S. et al, "Modern Pharmaceutices, $3^{rd}$ edition", Marcel Dekker, New York, 1996, pp. 451 and 596.
Barakat, S.E.S., Synthesis and hypoglycemic activity of some new 3-[4- [[[(cyclohexylamino) carbonyl] amino]sulfony]phenyl]-4(3H)-quinazolinones, Az. J. Pharm. Sci., vol. 25, (2000), pp. 48-57.
Barakat, S.E.S., Synthesis and Hypoglycemic Activity of Some New 4(3H) —Quinazolinone Analogues, Saudi Pharmaceutical Journal, vol. 8, No. 4 (2000) pp. 198-204.
Belgodere, Elena et al., Synthesis of Substituted Pyrimidines, Study of the Structure and of the Tautomeric Equilibria, (1976) Chem. Abstracts, Columbus, OH vol. 85 No. 9. XP002298337.
Bhaduri, A.P. et al., Urinary Metabolite of 2-Piperazino-3 (H)-4-Quinazolone (Centpiperalone), A Potent Blood Sugar Lowering Agent, Indian J. Biochem. Biophys., vol. 12 (1975), pp. 413-414.
Borrell, J.I. et al.: "Synthesis, structure and cytotoxicity evaluation of palladium(II) complexes of 4-amino-3-hydrazino-1,2,4-triazin-5(4h)-on es and 4-amino-3-(n-methylhydrazino)-1,2,4-triazi N-5(4H)-ones" Anales De Quimica, vol. 91, No. ¾, 1995, pp. 243-252, XP008000323.
Botta, M., Saladino, R., Lamba, D. Nicoletti, R.: Researches on Antiviral Agents. 31. Synthesis and Transformations of Racemic and Chiral 6-Oxiranyl Pyrimidinones, Tetrahedron, vol. 49, 1993, pp. 6053-6070, XP002329846.
Bouras, Mohammed, et al., Metabolism of enterostatin in rat intestine, brain, membranes and serum: differential involvement of proline-specific peptidases, Peptides, vol. 16, No. 3, (1995), pp. 399-405.
Brun, Jean-Frederic, et al., Effects of Oral Zinc Gluconate on Glucose Effectiveness and Insulin Sensitivity in Humans, Biological Trace Element Research vol. 47 (1995), pp. 385-391.
Buckley, DI, Analysis of the Degradation of Insulinotropin [GLP-1 (7-37)] In Human Plasma and Production of Degradation Resistant Analogs.
Buysens, K. J. et al.: "Synthesis of New Pyrrolo[3,4-b]- and [3,4-c]□uinazol(on)es and related 1,7-Naphthyridinones and 2,7-naphthyridines via intramolecular diels-alder reactions of 2(1 H)-pyrazinones" Tetrahedron, Elsevier Science Publishers, Amsterdam, NL, vol. 52, No. 27, (Jul. 1, 1996), pp. 9161-9178, XP004104003.
Cairo M R: "Crystalline Polymorphism of Organic Compounds" Topics in Current Chemistry, Springer, Berlin, DE, vol. 198, 1998, pp. 163-208, XP001156954 ISSN: 0340-1022 p. 165.
Callebaut, Christian et al. "T Cell Activation Antigien, CD26, as a Cofactor of Entry of HIV in CD4+ Cells" Science, (1993), vol. 262, pp. 2045-2050.

Cecil Textbook of Medicine, edited by Bennet, J.C., and Plum F., 20th edition, vol. 1, 1004-10, 1996.

Chatterjee, A.K. et al., Effect of Centpiperalone, a New Hypoglycemic Agent on Insulin Biosynthesis & Release from Isolated Pancreatic Islets of Rat, Indian Journal of Experimental Biology vol. 20 (1981) pp. 270-272.

Chatterjee, A.K. et al., Effect of Centpiperalone in Insulin Deficient Diabetes, Indian Journal of Experimental Biology vol. 18 (1980), pp. 1005-1008.

Chenard et al. J. Med Chem. 2001, 44, 1710-1717.

Cheng, Hung-Chi et al. "Lung Endothelial Dipeptidyl Peptidase IV Promoted Adhesion and Metastasis of Rat Brest Cancer Cells via Tumor Cell Surface-associated Gibronectin" J. of Bio. Chem., (1998), vol. 273, No. 37, pp. 24207-24215.

Coppola, Gary M. et al., 1-Aminomethylisoquinoline-4-carboxylates as Novel Dipeptidylpeptidase IV Inhibitors, Bioorganic & Medicinal Chemistry Letters vol. 10 (2000), pp. 1555-1558.

Database Beilstein [online] Beilstein Corssfire Institut Zur Foerderung Der Chemischen Wissenschaften, DE; 1989 XP002392086. Database Accession No. BRN 5951213 abstract.

Database Beilstein [online] Beilstein Crossfire Institut Zur Foerderung Der Chemischen Wissenschaften, DE; 1924, XP002392085. Database Accession No. BRN 3799088 abstract.

Database Beilstein [online] Beilstein Crossfire Institut Zur Foerderung Der Chemischen Wissenschaften, DE; 1960 XP002392087. Database Accession No. BRN 609897 abstract.

Database Beilstein [online] Beilstein Crossfire Institut Zur Foererung Der Chemischen Wissenschaften DE; 1974 XP002392089. Database Accession No. BRN 514343 abstract.

Database Beilstein [online] Beilstein Crossfire Institut Zur Foerderung Der Chemischen Wissenschaften, DE; 1993 XP002392088. Database Accession No. BRN 6139401 abstract.

Database Beilstein [online] Beilstein Crossfire Institut Zur Foerderung Der Chemischen Wissenschaften, DE; Citation No. 5593678 1991, XP00239083.

Database CA [online] Chemical Abstract service, Columbus, Ohio, US; Reg No. 102482-94-0 Liu, Gang: "Fungal endophyte-epichloe and its secondary metabolites" XP002392084. Database Accession No. 2004:340837 abstract.

Database Crossfire Beilstein Institut zur Foerderung der Wissenchaften, Frankfurt am Main, DE; XP002335066. Database Accession No. 386682 & J.Chem.Soc., 1952, pp. 4985-4990.

Database Crossfire Beilstein Institut zur Foerderung der Wissenchaften, Frankfurt am Main, DE; XP002335067. Database Accession No. 389575 & Chem.Ber., vol. 88, 1968, pp. 106-109.

Database Crossfire Beilstein Institut zur Foerderung der Wissenchaften, Frankfurt am Main, DE; XP002335074. Database Accession No. 392446, J.Heterocycl.Chem., vol. 8, 1971, pp. 367-371.

Database Crossfire Beilstein Institut zur Foerderung der Wissenchaften, Frankfurt am Main, DE; XP002335068. Database Accession No. 472441 & Yakugaku Zasshi, vol. 88, 1968, pp. 106-109.

Database Crossfire Beilstein Institut zur Foerderung der Wissenchaften, Frankfurt am Main, DE; XP002335076. Database Accession No. 490809, & Angew.Chem., vol. 84, 1972, p. 1185.

Database Crossfire Beilstein Institut zur Foerderung der Wissenchaften, Frankfurt am Main, DE; XP002335072. Database Accession No. 990008, J.Prakt.Chem., vol. 315, 1973, pp. 1166-1168.

Database Crossfire Beilstein Institut zur Foerderung der Wissenchaften, Frankfurt am Main, DE; XP002335065. Database Accession No. 1447134 & J.Org.Chem., vol. 43, 1978, pp. 4069-4074.

Database Crossfire Beilstein Institut zur Foerderung der Wissenchaften, Frankfurt am Main, DE; XP002335069. Database Accession No. 1447840 & Chem.Ber., vol. 101, No. 8, 1968, pp. 2679-2689.

Database Crossfire Beilstein Institut zur Foerderung der Wissenchaften, Frankfurt am Main, DE; XP002335064. Database Accession No. 1447881 & J. Heterocycl.Chem., vol. 305, 1972, pp. 724-730.

Database Crossfire Beilstein Institut zur Foerderung der Wissenchaften, Frankfurt am Main, DE; XP002335070. Database Accession No. 1448669 & Chem.Ber., vol. 101, No. 8, 1968, pp. 2679-2689.

Database Crossfire Beilstein Institut zur Foerderung der Wissenschaften, Franfurt am Main, DE: XP002335063. Database-Accession No. 1525341 & J. Heterocycl.Chem., vol. 12, 1975, pp. 683-687.

Database Crossfire Beilstein Institut zur Foerderung der Wissenchaften, Frankfurt am Main, DE; XP002335075. Database Accession No. 4742608, J. Prakt.Chem., vol. 333, No. 1, 1991, pp. 149-151.

Database Crossfire Beilstein Institut zur Foerderung der Wissenchaften, Frankfurt am Main, DE; XP002335071. Database Accession No. 4991064, J.Chem.Soc.Perkin Trans.1, 1980, pp. 1370-1380.

Database Crossfire Beilstein Institut zur Foerderung der Wissenchaften, Frankfurt am Main, DE; XP002335073. Database Accession No. 6219070, J.Prakt.Chem., vol. 330, No. 2, 1988, pp. 323-324.

Database Beilstein [online] Beilstein Crossfire Institut Zur Forderung Der Chemischen Wissenschaften, DE; 1991, XP002392082. Database Accession No. BRN 5340228 abstract.

Deacon, Carolyn F. et al., Both Subcutaneously and Intravenously Administered Glucagon-Like Peptide I Are Rapidly Degraded From the $NH_2$-Terminus in Type II Diabetic Patients and in Healthy Subjects, Diabetes, vol. 44 (1996), pp. 1125-1131.

Deacon, Carolyn F. et al., Degradation of Glucagon-Like Peptide 1 in Vitro Yields an N-Terminally Truncated Peptide That is a Major Endogenous Metabolite in Vivo, Journal of Clinical Endocrinology and Metabolism vol. 80, No. 3 (1995), pp. 952-957.

Deacon, Carolyn F. et al., Dipeptidyl peptidase IV Inhibition Influences GLP-1 Metabolism in Vivo, Regulatory Peptides vol. 64 Issues 1-3 (1996) p. 30.

Deacon, Carolyn F. et al., Dipeptidyl peptidase IV Inhibition Potentiates the Insulinotropic Effect of Glucagon-Like Peptide 1 in the Anesthetized Pig, Diabetes, vol. 47 (1998), pp. 764-769.

Deacon, Carolyn F. et al., Dipeptidyl peptidase IV Inhibition as an Approach to the Treatment and Prevention of Type 2 Diabetes: a Historical Perspective, Biochemical and Biophysical Research Communications 294 (2002), pp. 1-4.

Demuth, Hans-Ulrich et al., Rebuttal to Deacon and Holst: "Metaformin effects on ☐uinazolin peptidase IV degradation of glucagons-like peptide-1" versus "dipeptidyl peptidase inhibition as an approach to the treatment and prevention of type 2 diabetes: a historical perspective" Biochemical and Biophysical Research Communications 296 (2002) pp. 229-232.

Desai N C et al "Synthesis and anti-Hiv . . . " Indian Journal of Experimental Bio.,vol. 36, No. 12, 1998 pp. 1280-1283, XP008084509 ISSN: 0019-5889.

Dey, Paramita D., et al., Regioselective [4+2] Cycloaddition versus Nucleophilic Reactions of N-Arylamino Substituted 1,3-Diaza-1,3-Butadienes with Ketenes: Synthesis of Pyrimidinone and Fused Pyrimidione Derivatives. Part II. Tetrahedron, vol. 53, No. 40, pp. 13829-13840, 1997.

Dumas, Donald J. "Total synthesis of peramine" Journal of Organic Chemistry, American Chemical Society, Easton, US, vol. 5, 1988, pp. 4650-4653, XP002087391.

Engel, Michael et al., The crystal structure of dipeptidyl peptidase IV (CD26) reveals its functional regulation and enzymatic mechanism, Proc. Nat. Acad. Sci. Early Edition (2003), pp. 1-6.

EP 900568A2 Abstract from STN CAS online search printout (3 pages).

Fantus et al "Mechanism of Action . . . " Journal of Clinical. Endocrin. And Metabol. vol. 63, No. 4, pp. 898-905.

Felczak et al. Database Crossfire Beilstein Institut Zur Foerderung Der Chmischen Wissenschaften. XP002310121. Beilstein Registry No. 7289032 & Nucleosides Nucleotides, vol. 14, No. 3-5, 1995, pp. 653-656.

Fraisse, L., et al. Long-Chained Substituted Uric Acid and 5,6-Diaminouracil Derivatives as Novel Agents against Free Radical Processes: Synthesis and in Vitro Activity, Journal of Medicinal Chemistry, vol. 36, 1993, pp. 1456-1473, XP002329847.

Fraser & Kermack "The Reaction of Paludrine (Proguanil) with Ethyl Acetoacetate" 1951 pp. 2682-2686.

Garratt, Peter J. et al., One-Carbon Compounds as Synthetic Intermediates. The Synthesis of Hydropyrimidines and Hydroquinazolines by Sequential Nucleophilic Addition to Diphenyl Cyanocarbonimidate With Concomitant Cyclization, J. Org. Chem. (1988), pp. 1062-1069.

Garratt, Peter J. et al., A Novel Synthesis of Dihydropyrimidines, J. Chem. Soc., Chem. Commun. (1987), pp. 568-569. XP002298336.

Gazit, Aviv et al., Tyrphostins IV—Highly Potent Inhibitors of EGF Receptor Kinase. Structure-Activity Relationship Study of 4-Anilidoquinazolines, Bioorganic & Medicinal Chemistry, vol. 4, No. 8 (1996) pp. 1203-1207.

Green et al., Expert Opin. Emergin Drugs, 11(3); 525-539, 2006.

Guerrieri, N., et al., Vanadium Inhibition of Serine and Cysteine Proteases, Comparative Biochemistry and Physiology Part A 122 (1997), pp. 331-336.

Gupta, A. et al.: "Fluorine containing Biologically Active Agents: Synthesis of some new Pyrimidine Derivatives" J.Ind. Chem.Soc., vol. 71 1994, pp. 635-636, XP000889664 compound 1.

Gupta, C.M. et al., A Novel Class of Hypoglycaemic Agents: Syntheses & SAR in 2-Substituted 4(3H)-Quinazolones, 2-Substituted 4-Hydroxypolymethylene 5,6]pyrimidines & 3-Substituted 4-Oxopyrido [I,2-a] pyrimidines, Indian Journal of Chemistry, vol. 9 (1971), pp. 201-206.

Gupta, C.M. et al., Drugs Acting on the Central Nervous System. Syntheses of Substituted Quinazolones and Quinazolines and Triazepino-and Triazocionquinazolones, Division of Medicinal Chemistry, Central Drug Research Institute, Lucknow, India (1967), pp. 392-395.

Hamid et al. Scientia Pharmaceutica (2001), 69(4), 351-366.

Hcaplus 121: 35089 Snider, Barry B. et al. Tetrahedron Ltrs 1994 35(4) 531-4.

Hcaplus 122: 132810 Snider, Barry B. et al. Jornal of Organic Chem. 1994, 59(26) 8065-70.

Hermecz, Istvan et al., Pyrido[1,2-a]Pyrimidines; New Chemical Entities in Medicinal Chemistry, Medicinal Research Reviews, vol. 8, No. 2 (1988) pp. 203-230.

Hildebrandt, Martin et al. "A guardian angel: the involvement of dipeptidyl peptidase IV in psychoneuroendocrine function, nutrition and immune defence" Clinical Science, (2000), vol. 99, pp. 93-104.

Hinke, Simon A. et al., Metaformin Effects on Dipeptidylpeptidase IV Degradation of Glucagon-like Peptide-1, Biochemical and Biophysical Research Communications, 291 (2002) pp. 1302-1308.

Hinke, Simon A. et al., On Combination Therapy of Diabetes With Metaformin and Dipeptidyl Peptidase IV Inhibitors, Diabetes Care, vol. 25, No. 8 (2002) pp. 1490-1492.

Holz, George G. et al, Pancreatic Beta-Cells are Rendered Glucose-Competent by the Insulinotropic Hormone Glucagon-Like Peptide-1(7-37), Nature, vol. 361 (1993), pp. 362-365.

Jakubkiene, Virginija, et al., (G-Methyl-2methylsulfany1-4-oxo-3,4-dihydro-3-pyrimidinyl)acetic acid and related compounds exhibiting anti-inflammatory activity. Pharmazie 57 (2002) 9, pp. 610-613.

Jones, Terence R., et al., Azafluorenes Containing Two Bridgehead Nitrogen Atoms. Journal of the Chemical Society, Perkin Transactions 1, No. 12, Dec. 1987, pp. 2585-2592.

Kamata et al., CAPLUS Abstract 105: 191027, 1986 Chemical & Pharma Bulletin (1985), 33(8), 3160-75.

Kazuo, M. et al. "Reaction of Copper (II) Complexes Optically . . . " J. Chem. Soc. Dalton Trans. 1987, pp. 1127-1132, XP008082357.

Kesarwani, A. P. et al.: Solid-phase synthesis of ☐uinazoline-(3H)-ones with three-point diversity, Tetrahedron Letters, vol. 43, (2002) pp. 5579-5581.

Khalid, Noraini M., et al., Purification and Partial Characterization of a Prolyl-Dipeptidyl Aminopeptidase From *Lactobacillus helveticus* CNRZ 32, Applied and Environmental Microbiology (1990), pp. 381-388.

Kieffer, Timothy J. et al., Degradation of Glucose-Dependant Insulinotropic Polypeptide and Truncated Glucagon-Like Peptide 1 in Vitro and in Vivo by Dipeptidyl Peptidase IV, Endocrinology, vol. 136, No. 8 (1995) 3585-3596.

Kim, H.O. et al., Structure-Activity Relationships of 1,3-Dialkylxanthine Derivatives at Rat $A_3$ Adenosine Receptors, Journal of Medicinal Chemistry, vol. 37, 1994, pp. 3373-3382, XP002329848.

Kimura, Toshikiro et al., Oral Administration of Insulin as Poly(Vinyl Alcohol)-Gel Spheres in Diabetic Rats, Biological & Pharmaceutical Bulletin, vol. 19, No. 6 (1996), 897-900.

Kobe, J. et al.: "The synthesis of s-triazolo[4.3-a]1,3,5-triazines" Tetrahedron, Elsevier Science Publishers, Amsterdam, NL, vol. 26, Jul. 1970, pp. 3357-3368, XP002390908.

Koreeda, Yuji et al. "Isolation and characterization of dipeptidyl peptidase IV from *Prevotella loescheii* ATCC 15930" Archives of Oral Biology, vol. 46, 2001, 759-766.

Kotani, T. et al., "Highly selective aldose reductase . . . " Journal of Medicinal Chem., American Chem. Society. Washington, US, vol. 40, No. 5, 1997, pp. 684-694 XP000652330.

Kotra, L. P. et al.: "4-Azido-2-pyrimidone Nucleosides and Related Chemistry" Journal of Organic Chemistry, American Chemical Society. Easton, US, vol. 62, 1997, pp. 7267-7271, XP002390905.

Kozhevnikov et al. Tr. Perm. Sel.-Khoz. Inst. (1971), No. 79, 66-72 From ref. Zh., Khim. 1972, Abstr. No. 9Zh404 Journal (English Abstract attached).

Kusar, Mihael et al., Diethyl $N,N$-Dimethylaminomethylenemalonate in the Synthesis of Fused Heterocyclic Systems, Heterocyclic Chem. 33 (1996) pp. 1041-1046.

Lambeir, Anne-Marie et al. "Dipeptidyl-Peptidase IV from Bench to Bedside: An Update of Structural Properties, Functions, and Clinical Aspects f the Enzyme DPPIV" Clinical Reviews in Clinical Laboratory sciences, (2003), vol. 40(3), pp. 209-294.

Lin et al., CAPLUS Abstract 104:65665, 1986 Journal of Medicinal Chem. (1986), 29(1), 84-9.

Lin, Jian, Total Synthesis and Biological Evaluation of Fluoroolefin-containing Dipeptidyl Isosteres as Inhibitors of Dipeptidyl Peptidase IV (CD26), Dissertation presented to State University of New York at Albany, Department of Chemistry (1998).

Li Jinping, et al., Permolybdate and Pertungstate—Potent Stimulators of Insulin Effects in Rat Adipocytes: Mechanism of Action, Biochemistry, 34 (1995) 6218-6225.

Loeser, Eric et al., Selective $N$-Alkylation of Primary Amines with Chloroacetamides Under pH-Controlled Aqueous Conditions, Synthetic Communications, 32(3) (2002) pp. 403-409.

Majim R. Berichet der Deutschen Chemischen Gesellschaft 1908 41 pp. 176-186.

Mall et al. Reactivity Difference of Cis-Trans Pairs: I Behavior of Stillbene Oxides and Activates Stibene Imines, 1987, Journal of Organic Chemistry, 1987, vol. 52, pp. 4812-4814.

Mannucci, Eduardo, et al., Effect of Metaformin on Glucagon-Like Peptide-1 (GLP-1) and Leptin Levels in Obese Nondiabetic Subjects, Diabetes Care, vol. 24, No. 3 (2001) 489-494.

Marcus et al. PubMed Abstract (Intervirology, 45/4-6):260-6) 2002.

Mentlein, Rolf et al., Dipeptidyl-Peptidase IV Hydrolyses gastric Inhibitory Polypeptide, Glucagon-Like Peptide-1(7-36)amide, Peptide Histidine Methionine and is Respoinsible for Their Degradation in Human Serum, Eur. J. Biochem, vol. 214, 829-835 (1993).

Meyerovitch, Josph et al. "Oral Administration of Vanadate Normalizes Blood Glucose Levels in Streptozotocin-treated Rats" Journal of Biological Chemistry, 1987, vol. 262, No. 14, pp. 6658-6662.

Misra, V. et al. "Synthesis of N-aryl-n . . . " Pol. J. Pharmacol Pharm vol. 31, 1979, pp. 161-167, XP008084507.

Molina, P. et al.: "Iminophosphorane-mediated annulation of 1,3,5-triazine to benzimidazole: Synthesis of 1,3,5-triazino[1,2-a]benzimidazoles" Synthesis 1992 Germany, No. 3, 1992—pp. 297-302, XP002390907.

Mukherjee et al "A novel hypoglycemic compound" Biochemical Pharmacology, vol. 22, 1972, pp. 1529-1531.

Mukerjee, S.S. et al., Chronic Toxicity Studies of a Hypoglycemic Compound: Centpiperalone in Rats & Rhesus Monkeys, Indian Journal of Experimental Biology, vol. 17 (1979) pp. 1346-1349.

Mukerjee, S.S. et al., Tissue Distribution of [3H]Centpiperalone after Oral Administration, Indian J. Biochem. Biophys., vol. 17 (1980) pp. 399-401.

Mukerjee, Surath K. et al., Effect of 2-piperazino-4(3H)-quinazolinone monoacetate on some aspects of carbohydrate metabolism of albino rats, Biochemical Pharmacology, vol. 22 (1973) pp. 2205-2206.

Mukerjee, S.S. et al., Effect of 2-piperazino-4(3H)-quinazolinone monoacetate on the tissue respiration, glucose uptake and lactic acid production by rat hemidiaphragm, Biochemical Pharmacology, vol. 23 (1974) 3066-3067.

Mukherjee, Surath K. et al., Influence of Timing Oral Dosing of a Novel Hypoglycaemic Agent A-4166 in Relation to Food, Diabetologia vol. 38 A194 Supplement 1 (1995).

Mukerjee, S.S. et al., Studies on the Mechanism of Centpiperalone-Induced Hypoglycemia, Acta Diabet. Lat 13, 8 (1976) p. 8.

Mukherjee, Surath K. et al., Studies on the Metabolic Changes Induced by a Synthetic Insulinogenic Agent, Ind. J. Physiol. & Allied Sci., vol. 30, No. 3 (1976) pp. 105-116.

Murthy, G. Rama et al., New Hypoglycemic Agents: Synthesis and Hypogylcemic Activity of Some New 1-[{p-(4-OXO-2-Substituted-3(4H)-Quinazolinyl)-Phenyl) Sulphonyl]-3-Aryl/Cyclohexyl-2-Thioureas, Current Science, vol. 56, No. 24 (1987) pp. 1263-1265.

Murthy, G. Rama et al., New Hypoglycemic Agents: Part V—Synthesis & Hypoglycemic Activity of Some New 1-[[p-(4-OXO-2-Methyl/Phenyl-3 (4H)-Quinazolinyl) Phenyl]] 3-Aryl-2-Ureas, Indian Drugs, 25 (1) (1987) pp. 19-22.

Nakamura, Seiji, et al., Effect of Chronic Vanadate Administration in Partially Depancreatized Rats, Diabetes Research and Clinical Practice 27 (1995) pp. 51-59. (Abstract Only).

Ohkubo, I., et al., Dipeptidyl Peptidase IV From Porcine Seminal Plasma: Purification, Characterization, and N-Terminal Amino Acid Sequence, J. Biochem. (Tokyo) (1994) 116(5) pp. 1182-11826.

Oord, J.J.Van Den "Expression of CD26/dipeptidyl-peptidase IV in benign and malignant pigment-cell lesions of the skin" British Journal of Dermatology, 1998, vol. 138, pp. 615-621.

Pandeya, S.N. et al., Synthesis of Some New Amidine Derivatives As Potent Hypoglycemic Agents, Pharmacological Research Communications, vol. 17, No. 8 (1985) pp. 699-709.

Patent Asbstracts of Japan Publication No. 2002338551, Publication Date Nov. 27, 2002.

Patent Abstracts of Japan, vol. 2003, No. 12, Xanthine Derivative, Dec. 5, 2003 & JP 2003 300977 A (Sumitomo Pharmaceut Co Ltd), Oct. 21, 2003, Abstract.

Pauly, et al. "Inhibition of DPPIV in Rat . . . " RegulatoryPeptides, vol. 64, Issues 1-3, 1996, p. 148.

Pederson, et al. "Improved Glucose Tolerance in Zucker Fatty Rats by Oral Administration of the Dipeptidyl Peptidase IV Inhibitor Isoleucine Thiazolidide" Diabetes, vol. 47, 1998, pp. 1253-1258.

Pillai, Sreekumar et al. "Effects of ATP, Vanadate and Molybdate on Cathepsin D-catalyzed Proteolysis" J of Bio Chem, No. 14, pp. 8384-8389.

Podanyi, B. et al. "Nitrogen Bridge Compounds . . . " Journal Organic Chemistry, 1986, vol. 51, pp. 394-399.

Poje "Diabetogenic_action_of_alloxan-like . . . " Experientia—vol. 36—1980—pp. 78-79.

Poje et al. "Oxidation of Uric Acid. 4, Synthesis, Structure, and Diabetogenic Action of 5-Imino-2,4,6(1H,3H,5H_-pyrimidinetrione Salts and Their Alloxan-Like Covalent Adducts" J. of Med. Chem. 1988, vol. 28, pp. 861-861.

Polacek et al. "Hypoglycemic Activity of Amine Derivatives" Preliminary Observations Chemische Fabrik von Heyden GmbH. Rogensburg. Azneim-Forsh / Drug Res. 28(1), Heft 5 (1978), pp. 791-793.

Ram, Vishnu Ji et al., Synthesis and Antihyperglycemic Activity of Suitably Functionalized 3H-quinazolin-4-ones, Bioorganic & Medicinal Chemistry 11 (2003), pp. 2439-2444.

Rauchman, B.S. et al. "2,4-Diamino-5-benylpyrimidines and Analogues as antibacterial Agents", Journal of Med. Chem., vol. 23, 1980, pp. 384-391, XP002335048 Scheme II.

Sammour et al. Egyptian Journal of Chemistry (1979) Volume Date 1976, 19(6), 1109-16. (Abstract 2 pages).

Sawyer, James H. et al., Pyrido[1,2-a]pyrimidinium Salts. Part 1. Synthesis from 2-Aminopyridines and Interconversion with 2-(2-Acylvinylamino) pyridines, J.C.S. Perkin I (1972), 1138-1143.

Saxena, A.M. et al., Mode of action of three structurally different hypoglycemic agents: A comparative study, Indian Journal of Experimental Biology, vol. 34 (1996), pp. 351-355.

Schilling et al., CAPLUS 2005:1050865 DN 143:347172.

Sedo, Aleksi et al., Dipeptidyl peptidase IV-like molecules: homologous proteins or homologous activities? Biochimica et Biophysica Acta 1550 (2001), pp. 107-116.

Sekiya, T. et al., Pyrimidine derivatives. III (1) Synthesis of hypoglycemic 4-alkoxy-2-piperazino-activity of 6-polymethylenepyrmidines, Eur. J. Med. Chem. (1982), 75-79.

Senten, Kristel et al., Development of Potent and Selective Dipeptidyl Peptidase II Inhibitors, Bioorganic & Medicinal Chemistry Letters 12 (2002) pp. 2825-2828.

Seth, M. et al., Syntheses of 2-Substituted & 2,3-Distributed 4(3H)-Quinazolones, Indian Journal of Chemistry, vol. 14B (1975), 536-540.

Sharma, Arun K., et al. Tandem sigmatropic shifts in [4 +2] cycloaddition reactions of 1,3-diazabuta-1,3-dienes with butadienylketene: synthesis of pyrimidinone derivatives. J. Chem. Soc., Perkin Trans. 1, 2002, 774-784.

Shimazawa, Rumiko et al. "Novel Small Molecule Nonpeptide Aminopeptidase N Inhibitors with a Cyclic Imide Skeleton" Journal of Enzyme Inhibition, vol. 14, 1999, pp. 259-275.

Shisheva, Assia, et al., Insulinlike Effects of Zinc Ion in Vitro and in Vivo; Preferential Effects on Desensitized Adipocytes and Induction of Normoglycemia in Streptozocin-Induced Rats, Diabetes, vol. 41 (1992), pp. 982-988.

Sinyak, R. S. et al., Synthesis and Biological Properties of Derivatives of 4-Heterylmercaptoquinazoline, Translated from Khimiko-farmatsevticheskii Zhurnal, vol. 20, No. 2, pp. 168-171 (1986), pp. 103-105.

Sokal, Joseph E., Basal Plasma Glucagon Levels of Man, Journal of Clinical Investigation, vol. 46, No. 5 (1967) pp. 778-785.

Soliman et al. Journal of the Chemical Society of Pakistan (1986), 8(2), 97-106. (Abstract 2 pages).

Somasekhara et al. Indian Journal of Pharmacey (1972), 34(5), 121-2.

Srivastava, P.P. et al., Efficacy of Centpiperalone in Combination With Biguanide & Sulfonylurea, Indian Journal of Experimental Biology, vol. 21 (1983), pp. 390-392.

Sun et al. CAPLUS Abstract 128:257413 (1998).

Syadyaryavichyute et al. Database Crossfire Beilstein Institut Zur Foerderung Der Chmischen Wissenschaften. XP002310118. Beilstein Registry No. 7643626 & Khim. Geterotsikl. Soedin., vol. 32, No. 5, 1996, pp. 703-707.

Tam, S. Y-K, et al.: "Nucleosides 112. Synthesis of Some New Pyrazolo-1 5-A-1 3 5-Triazines and Their C Nucleosides" Journal of Organic Chemistry, vol. 44, No. 25, 1979, pp. 4547-4553, XP002390906.

Tanaka, Keiji et al, Vanadate Inhibits the ATP-Dependant Degradation of Proteins in Reticulocytes Without Affecting Ubiquitin Conjugation, The Journal of Biological Chemistry, vol. 259, No. 4 (1983), 2803-2809.

Troschuetz, R. et al. Database CA Online Chemical Abstracts Service, Columbus, OH, US;, the reaction of O-functional benzylmalononitriles with N-bisnucleophiles as well as alcoholates. XP002311761 retrieved from STN Database accession No. 1994:217538 abstract & Archly Der Pharmazie (Winheim, Germany), 326(11), 865-9 Coden: ARPMAS; ISSN: 0365-6233, 1993.

Van Heeswijk et al., PubMed Abstract (Antivir Ther. 6(4);2001-29) Dec. 2001.

Villhauer, Edwin B. et al., 1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties, J. Med. Chem. 46 (2003), pp. 2774-2789.

Villhauer, Edwin B. et al., DPP-IV Inhibition and Therapeutic Potential, Annual Reports in Chemistry 36 (2001), 191-200.

Vippagunta et al, Advanced Drug Delivery Reviews 48: 3-26, 2001.

Wang, F. et al.: "A novel Synthesis of Aryl[1,2-a]pyrazine Derivatives" Molecules, Molecular Diversity Preservation International, Basel, CH, vol. 9, May 2004, pp. 574-582, XP002390904.

Wang et al. "Studies of Quinolinones . . . " Biorganic & Med hem.. Letters, Oxford, GB, vol. 12, No. 4, 2002, pp. 571-574, XP009077496 ISSN 0960-894X.

Weber, A.E.: Dipeptidyl Peptidase IV Inhibitors for the Treatment of Diabetes, Journal of Medicinal Chemistry, vol. 47, 2004 pp. 4135-4141, XP002329845.

West, Antony R., Solid State Chemistry and its Applictions, Wile, New York, 1988, pp. 358 & 365.

Wiedeman, Paul E. et al. "Dipeptidyl peptidase IV inhibitors for the treatment of impaired glucose tolerance and type 2 diabetes" Current Opinion in Investigational Drugs, 2003, vol. 4, No. 4, pp. 412-420.
Wolfe et al., CAPLUS Abstract 115: 114452 (1991).
Wolfe et al. Database Crossfire Beilstein Institut Zur Foerderung Der Chmischen Wissenschaften. XP002310119. Beilstein Registry No. 649497 & J. Pharm. Sci. vol. 80, No. 7, 1991, pp. 705-706.
Wolf Manfred E. "Burger's Medicinal Chemistry, 5ed, Part 1" John Wiley and Sons, 1995, pp. 975-977.
Yakubkene et al. Database Crossfire Beilstein Institut Zur Foerderung Der Chmischen Wissenschaften. XP002310117. Beilstein Registry No. 8373244 & Khim. Geterotsikl. Soedin., No. 8, 1998, pp. 1125-1129.
Yasuda, Nobuyuki et al. "Enhanced secretion of glucagon-like peptide 1 by biguande compouns" Biochem and Biophysical Research Communications, vol. 298, 2002, pp. 779-784.

Yuen, V.G. et al. "Acute and chronic oral administration of bis(maltolato)oxovanadium(IV) in Zucker diabetic fatty (ZDF) rats" Diabetes Research and Clinical Practice, vol. 43, 1999, pp. 9-19.
Zander, Mette et al. "Additive glucose-loweing effects of glucagon-like peptide-1 and metformin in type 2 diabetes" Diabetes Care, vol. 24, 2001, pp. 720-725.
Zhang, Anqi et al. "Vanadate Stimulation of Insulin Release in Normal Mouse Islets" Journal of Biological Chemistry, vol. 266, No. 32, 1991, pp. 21649-21656.
Zorbach et al. Database Crossfire Beilstein Institut Zur Foerderung Der Chmischen Wissenschaften. XP002310120. Beilstein Registry No. 638238 & Synthetic Procedures in Nucleic Acid Chemistry, vol. 1, 1968, p. 92.

* cited by examiner

POLYMORPHS OF SUCCINATE SALT OF 2-[6-(3-AMINO-PIPERIDIN-1-YL)-3-METHYL-2,4-DIOXO-3,4-DIHYDRO-2H-PYRIMIDIN-1-YLMETHY]-4-FLUOR-BENZONITRILE AND METHODS OF USE THEREFOR

RELATED APPLICATION

This application claims the benefit of U.S. Provisional Application No. 60/867,764 filed Nov. 29, 2006, and the disclosure of which is expressly incorporated by reference in its entirety. This application also relates to U.S. Patent Application Publication No. 2008/0227798, entitled POLYMORPHS OF SUCCINATE SALT OF 2-[6-(3-AMINO-PIPERIDIN-1-YL)-3-METHYL-2,4-DIOXO-3,4-DIHYDRO-2H-PYRIMIDIN-1-YLMETHY]-4-FLUOR-BENZONITRILE AND METHODS OF USE THEREFOR, filed on the same day by the same inventive entities as the present application, and the disclosure of which is expressively incorporated by reference in its entirety.

FIELD OF THE INVENTION

The present invention relates generally to polymorphic forms of the succinic acid salt of 2-[6-(3-amino-piperidin-1-yl)-3-methyl-2,4-dioxo-3,4-dihydro-2H-pyrimidin-1-ylmethyl]-4-fluoro-benzonitrile, (referred to herein as "Compound I") and methods for their preparation. The present invention also relates to pharmaceutical compositions, kits and articles of manufacture comprising polymorphs of Compound I, and methods of their use.

DESCRIPTION OF RELATED ART

Compound I, which has the formula:

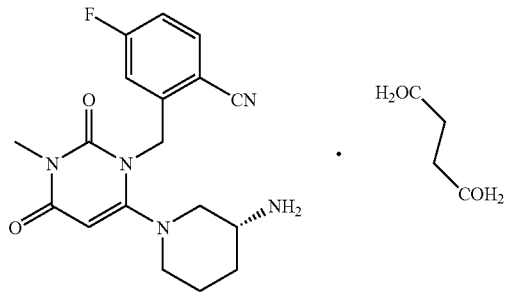

is a DPP-IV inhibitor that is described in U.S. patent application Ser. No. 11/080,992 filed Mar. 15, 2005 (see Compound 34). Its dosing, administration and biological activities are described in U.S. patent application Ser. No. 11/531,671 filed Sep. 13, 2006. U.S. patent application Ser. No. 11/080,992 and Ser. No. 11/531,671 are incorporated herein by reference in their entirety.

Dipeptidyl peptidase IV (IUBMB Enzyme Nomenclature EC.3.4.14.5) (referred herein as "DPP-IV") is a type II membrane protein and a non-classical serine aminodipeptidase that removes Xaa-Pro dipeptides from the amino terminus (N-terminus) of polypeptides and proteins. DPP-IV is constitutively expressed on epithelial and endothelial cells of a variety of different tissues (e.g., intestine, liver, lung, kidney and placenta), and is also found in body fluids. DPP-IV is also expressed on circulating T-lymphocytes and has been shown to be synonymous with the cell-surface antigen, CD-26. DPP-IV has been implicated in a number of human disease states, including, but are not limit to, diabetes, particularly type II diabetes mellitus, diabetic dislipidemia, conditions of impaired glucose tolerance (IGT), conditions of impaired fasting plasma glucose (IFG), metabolic acidosis, ketosis, appetite regulation and obesity; autoimmune diseases such as inflammatory bowel disease, multiple sclerosis and rheumatoid arthritis; AIDS; and cancers.

DPP-IV inhibitors are believed to be useful agents for the prevention, delay of progression, and/or treatment of conditions mediated by DPP-IV.

SUMMARY OF THE INVENTION

The present invention provides novel polymorphic forms of Compound I and methods of preparing these polymorphic forms, as well as compositions comprising one or more of the novel polymorphs. For ease of reference, the different polymorphs described herein are referred to consistently throughout the application as Forms A through G, and Amorphous Form.

Form A

In one embodiment, the present invention relates to a polymorph of Compound I, referred to herein as Form A. Based on its physical properties, Form A is a crystalline form.

Form A may be characterized as having one or more of the following physical characteristics (it being noted that a composition need not necessarily exhibit all of these characteristics in order to indicate the presence of Form A):

(a) may be crystallized from a solvent selected from the group consisting of (i) acetone, (ii) acetonitrile, (iii) dichloromethane, (iv) 1,4-dioxane, (v) dimethylformamide, (vi) ethanol, (vii) ethylacetate, (viii) diethylether, (ix) hexane; (x) methanol, (xi) isopropanol, (xii) tetrahydrofuran, (xiii) toluene, (xiv) trifluoroethanol, (xv) water, (xvi) acetonitrile:water (85:15), (xvii) ethanol:water (95:5), (xviii) isopropanol:water (88:12), and (xix) tetrahydrofuran:water (9:1);

(b) may be precipitated by adding a miscible antisolvent to Compound I dissolved in a solvent, wherein the solvent/antisolvent system is selected from the group consisting of (i) dimethylformamide/acetonitrile, (ii) dimethylformamide/toluene, (iii) dimethylformamide/ethylacetate, (iv) dimethylformamide/isopropanol, (v) methanol/acetonitrile, (v) methanol/dichloromethane, (vi) trifluoroethanol/isopropanol, (vii) trifluoroethanol/acetonitrile, (viii) trifluoroethanol/ethylacetate, (ix) water/acetonitrile, and (x) water/tetrahydrofuran;

(c) has an X-ray powder diffraction pattern (CuKα, λ=1.5418 Å) comprising diffraction peaks at about 11.31, 11.91, and 22.32 degree 2-theta (°2θ), more particularly, comprising five or move diffraction peaks selected from the group consisting of diffraction peaks at about 4.80, 11.31, 11.91, 12.86, 14.54, 15.81, 16.83, 17.59, 18.11, 19.26, 19.52, 20.32, 21.04, 21.80, 22.32, 23.42, 23.83, 24.78, 25.28, 25.84, 26.14, 26.63, 27.62, 27.84, 28.14, 29.39, 29.87, 30.27, 31.60, 31.88, 32.44, 33.86, 34.51, 35.87, 36.36, 37.31, 38.64, and 39.49° 2θ, even more particularly, comprising diffraction peaks at about 11.31, 11.91, 19.26, 21.04, and 22.32° 2θ;

(d) has a Fourier transform infra-red absorption spectrum comprising absorption bands at about 3141, 2953, 2934, 2266, 1699, 1657, 1450, and 1206 wave number (cm$^{-1}$), and more particularly absorption bands at about 3141, 2953, 2934, 2266, 2225, 1699, 1657, 1450, 1206, 886, 760, 685, 594, and 516 cm$^{-1}$;

(e) has a Raman spectrum comprising Raman peaks at about 2954, 2935, 2225, 1698, 1659, and 1607 cm$^{-1}$, and more particularly comprising Raman peaks at about 3068, 2954, 2935, 2225, 1698, 1659, 1607, 1586, 1223, 1180, 901, 780, 751, 669, and 516 cm$^{-1}$;

(f) a differential scanning calorimetry spectrum having an endotherm centered at about 195° C.; and (g) insignificant weight loss when heated from 25° C. to 165° C.

Form B

Form B may be characterized as having one or more of the following physical characteristics (it being noted that a composition need not necessarily exhibit all of these characteristics in order to indicate the presence of Form B):

(a) may be crystallized from a solvent selected from the group consisting of (i) isopropanol, (ii) ethanol:water (95:5), (ii) isopropanol:water (88:12), (iii) tetrahydrofuran:water (9:1), and (iv) water;

(b) may be precipitated by adding dioxane to Compound I dissolved in water;

(c) has an X-ray powder diffraction pattern (CuKα, λ=1.5418 Å) which comprises characteristic peaks at about 12.51, 18.83, and 24.46° 2θ;

(d) has a differential scanning calorimetry thermogram comprising a broad endotherm at about 100° C., and two small endotherms at about 138° C. and about 163° C., and another endotherm at about 193° C.;

(e) has a significant weight loss (>2.0%) when heated from about 25° C. to 175° C.; and (f) converts to Form A when dissolved in water and recovered by evaporation of the solvent.

Form C

Form C may be characterized as having one or more of the following physical characteristics (it being noted that a composition need not necessarily exhibit all of these characteristics in order to indicate the presence of Form C):

(a) may be crystallized from an isopropanol solution of Compound I; and (b) has an X-ray powder diffraction pattern (CuKα, λ=1.5418 Å) which comprises diffraction peaks at about 5.44±0.2 and 6.07±0.2° 2θ.

Form D

Form D may be characterized as having one or more of the following physical characteristics (it being noted that a composition need not necessarily exhibit all of these characteristics in order to indicate the presence of Form D):

(a) may be precipitated by adding a miscible antisolvent to a solution of Compound I; e.g., adding acetonitrile to a water solution of Compound I;

(b) has an X-ray powder diffraction pattern (CuKα, λ=1.5418 Å) comprising diffraction peaks at about 12.19, 22.88, and 24.33° 2θ; alternatively, a diffraction pattern comprising one diffraction peak at about 24.33° 2θ and four other peaks selected from the group consisting of diffraction peaks at about 12.19, 14.04, 16.71, 17.75, 18.86, 19.96, 22.08, 22.88, 23.27, 25.02, 25.49, 26.03, and 27.99° 2θ, and more particularly, a diffraction pattern comprising one diffraction peak at about 24.33° 2θ and four other peaks selected from the group consisting of diffraction peaks at about 12.19, 16.71, 22.08, 22.88, and 23.27° 2θ;

(c) has a differential scanning calorimetry thermogram having a broad, noisy endotherm centered at about 88° C., and two others endotherms at about 107° C. and 192° C.; and (d) has a weight loss of >20% when heated from 20° C. to 85° C. due to water loss.

Form E

Form E may be characterized as having one or more of the following physical characteristics (it being noted that a composition need not necessarily exhibit all of these characteristics in order to indicate the presence of Form E):

(a) may be precipitated by adding a miscible antisolvent to a solution of Compound I; e.g., by adding acetonitrile to a water solution of Compound I;

(b) has an X-ray powder diffraction pattern (CuKα, λ=1.5418 Å) comprising two diffraction peaks at about 21.27 and 17.15° 2θ, and three other diffraction peaks selected from the group consisting of peaks at about 11.90, 12.66, 13.10, 13.59, 13.94, 17.54, 22.03, 22.61, 24.06, 24.70, 26.31, 27.34, and 31.10° 2θ, and more particularly a diffraction pattern comprising diffraction peaks at about 13.10, 13.94, 17.15, and 21.27° 2θ;

(c) has a differential scanning calorimetry thermogram having two small endotherms at about 59° C. and about 75° C., a forked endotherm having peaks at about 107° C., 110° C. and 114° C., and another endotherm at about 192° C.; and (d) has a weight loss of >2% when heated from 25° C. to 85° C.

Form F

Form F may be characterized as having one or more of the following physical characteristics (it being noted that a composition need not necessarily exhibit all of these characteristics in order to indicate the presence of Form F):

(a) may be crystallized from a tetrahydrofuran and water solution of Compound I; and (b) has an X-ray powder diffraction pattern (CuKα, λ=1.5418 Å) which comprises diffraction peaks at about 12.39, 20.63, 26.03, and 30.05° 2θ.

Form G

Form G may be characterized as having one or more of the following physical characteristics (it being noted that a composition need not necessarily exhibit all of these characteristics in order to indicate the presence of Form G):

(a) may be formed by crystallization from a tetrahydrofuran and water solution of Compound I; and (b) has an X-ray powder diffraction pattern (CuKα, λ=1.5418 Å) comprising three or more diffraction peaks selected from a group consisting of peaks at about 13.22, 14.23, 18.62, 19.77, 24.36, 25.06, and 30.71° 2θ.

Amorphous Form

The amorphous form ("Amorphorus Form") may be characterized as having one or more of the following physical characteristics (it being noted that a composition need not necessarily exhibit all of these characteristics in order to indicate the presence of Amorphous Form):

(a) may be formed by lyophilizing a water solution of Compound I;

(b) has an XRPD spectrum characterized by a large halo with no discernable peak;

(c) has a differential scanning calorimetry spectrum showing the glass transitional temperature at 82° C., an exotherm at about 138° C. and an endotherm at about 199° C.

Methods by which the above referenced analyses were performed in order to identify these physical characteristics are described in the Example 3.

Compositions Comprising Compound I

The present invention relates to compositions comprising Compound I, wherein Compound I is present in a form selected from the group consisting of Form A, Form B, Form C, Form D, Form E, Form F, Form G, and Amorphous Form. It is noted that other crystalline and amorphous forms of Compound I may also be present in the composition.

In one variation, the composition comprises at least 0.1%, 0.25%, 0.5%, 1%, 5%, 10%, 25%, 50%, 75%, 80%, 85%, 90%, 95%, 97%, or 99% of Compound I where greater than 0.1%, 0.25%, 0.5%, 1%, 5%, 10%, 25%, 50%, 75%, 80%, 85%, 90%, 95%, 97% or 99% of Compound I (by weight) is present in the composition in a form selected from the group consisting of Form A, Form B, Form C, Form D, Form E, Form F, Form G, and Amorphous Form. The composition may optionally be a pharmaceutical composition. The pharmaceutical composition may optionally further include one or more pharmaceutical carriers.

Kits and Articles of Manufacture Comprising Compound I

The invention also provided are kits and other articles of manufacture comprising a composition that comprises Compound I, wherein Compound I is present in a form selected from the group consisting of Form A, Form B, Form C, Form D, Form E, Form F, Form G, and Amorphous Form. In one variation, the composition comprises at least 0.1%, 0.25%, 0.5%, 1%, 5%, 10%, 25%, 50%, 75%, 80%, 85%, 90%, 95%, 97%, or 99% of Compound I where greater than 0.1%, 0.25%, 0.5%, 1%, 5%, 10%, 25%, 50%, 75%, 80%, 85%, 90%, 95%, 97% or 99% of Compound I (by weight) is present in the composition in a form selected from the group consisting of Form A, Form B, Form C, Form D, Form E, Form F, Form G, and Amorphous Form. The composition in the kits and articles of manufacture may optionally be a pharmaceutical composition. The pharmaceutical composition may optionally further include one or more pharmaceutical carriers.

In regard to each of the above embodiments including a pharmaceutical composition, the pharmaceutical composition may be formulated in any manner where at least a portion of Compound I is present in a form selected from the group consisting of Form A, Form B, Form C, Form D, Form E, Form F, Form G, and Amorphous Form. Optionally, a portion of Compound I is present in a form selected from the group consisting of Form A, Form B, Form C, Form D, Form E, Form F, Form G, and Amorphous Form for a period of time subsequent to administration of the pharmaceutical formulation to a human.

Methods of Making Form A Through Form G and Amorphous Form

Various methods are also provided for making Form A through Form G, and Amorphous Form. Various methods are also provided for manufacturing pharmaceutical compositions, kits and other articles of manufacture comprising one or more of Form A through Form G, and Amorphous Form.

Methods of Using Form A Through Form G and Amorphous Form

Methods of using a pharmaceutical composition, kit and other article of manufacture comprising one or more of Form A through Form G, and Amorphous Form to treat various diseases mediated by DPP-IV are also provided.

In one embodiment, the present invention relates to a method of inhibiting dipeptidyl peptidases comprising administering a composition where greater than 0.1%, 0.25%, 0.5%, 1%, 5%, 10%, 25%, 50%, 75%, 80%, 85%, 90%, 95%, 97% or 99% of Compound I (by weight) is present in the composition in a form selected from the group consisting of Form A, Form B, Form C, Form D, Form E, Form F, Form G, and Amorphous Form. Optionally, the composition comprises at least 0.1%, 0.25%, 0.5%, 1%, 5%, 10%, 25%, 50%, 75%, 80%, 85%, 90%, 95%, 97%, or 99% of Compound I.

In another embodiment, the present invention relates to a method of inhibiting dipeptidyl peptidases in a subject (e.g., human body) with Compound I by administering Compound I where greater than 0.1%, 0.25%, 0.5%, 1%, 5%, 10%, 25%, 50%, 75%, 80%, 85%, 90%, 95%, 97% or 99% of Compound I (by weight) is present in the composition in a form selected from the group consisting of Form A, Form B, Form C, Form D, Form E, Form F, Form G, and Amorphous Form, when the compound is administered. Optionally, the composition comprises at least 0.1%, 0.25%, 0.5%, 1%, 5%, 10%, 25%, 50%, 75%, 80%, 85%, 90%, 95%, 97%, or 99% of Compound I.

In another embodiment, the present invention relates to a method of inhibiting dipeptidyl peptidases in a subject (e.g., human body) with Compound I by administering Compound I where greater than 0.1%, 0.25%, 0.5%, 1%, 5%, 10%, 25%, 50%, 75%, 80%, 85%, 90%, 95%, 97% or 99% of Compound I (by weight) is present in the composition in a form selected from the group consisting of Form A, Form B, Form C, Form D, Form E, Form F, and Amorphous Form for a period of time after the compound has been administered to a subject. Optionally, the composition comprises at least 0.1%, 0.25%, 0.5%, 1%, 5%, 10%, 25%, 50%, 75%, 80%, 85%, 90%, 95%, 97%, or 99% of Compound I.

In still another embodiment, the present invention provides a method of treating a disease state for which dipeptidyl peptidases possesses activity that contributes to the pathology and/or symptomology of the disease state, comprising administering to a subject (e.g., human body) a composition where greater than 0.1%, 0.25%, 0.5%, 1%, 5%, 10%, 25%, 50%, 75%, 80%, 85%, 90%, 95%, 97% or 99% of Compound I (by weight) is present in the composition in a form selected from the group consisting of Form A, Form B, Form C, Form D, Form E, Form F, Form G, and Amorphous Form when administered. Optionally, the composition comprises at least 0.1%, 0.25%, 0.5%, 1%, 5%, 10%, 25%, 50%, 75%, 80%, 85%, 90%, 95%, 97%, or 99% of Compound I.

In still another embodiment, the present invention provides a method of treating a disease state for which dipeptidyl peptidases possesses activity that contributes to the pathology and/or symptomology of the disease state, comprising causing a composition to be present in a subject (e.g., human body) where greater than 0.1%, 1%, 5%, 10%, 25%, 50%, 75%, 80%, 85%, 90%, 95%, 97% or 99% of Compound I (by weight) is present in the composition in a form selected from the group consisting of Form A, Form B, Form C, Form D, Form E, Form F, Form G, and Amorphous Form, for a period of time after the composition has been administered to a subject. Optionally, the composition comprises at least 0.1%, 0.25%, 0.5%, 1%, 5%, 10%, 25%, 50%, 75%, 80%, 85%, 90%, 95%, 97%, or 99% of Compound I.

In another embodiment, a method is provided for preventing, delaying the of progression, and/or treating conditions mediated by DPP-IV, in particular diabetes and more particularly, type 2 diabetes mellitus, diabetic dislipidemia, conditions of impaired glucose tolerance (IGT), conditions of impaired fasting plasma glucose (IFG), metabolic acidosis, ketosis, appetite regulation and obesity; autoimmune diseases such as inflammatory bowel disease, multiple sclerosis and rheumatoid arthritis; AIDS, cancers, and others.

In each instance where it is stated that Compound I may be present in the composition in a form selected from the group consisting of Form A, Form B, Form C, Form D, Form E, Form F, Form G, and Amorphous Form, it is intended for the invention to encompass compositions where only one form is present, where two forms are present (all combinations) and where three, four or more forms are present (all combinations).

DETAILED DESCRIPTION OF THE INVENTION

Figure 1:
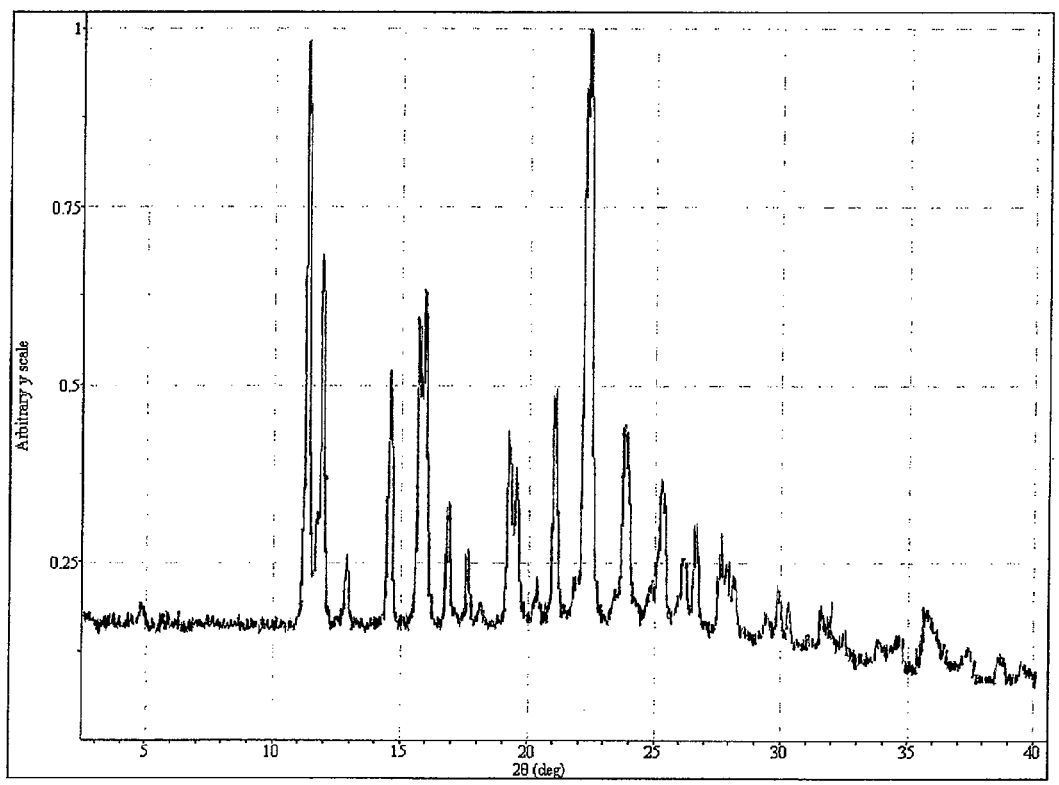
FIG. 1 is a characteristic x-ray powder diffraction (XRPD) spectrum of Form A.

The present invention is directed to novel polymorphs, and compositions comprising the succinic acid salt of 2-[6-(3-amino-piperidin-1-yl)-3-methyl-2,4-dioxo-3,4-dihydro-2H-pyrimidin-1-ylmethyl]-4-fluoro-benzonitrile (Compound 1) of the formula

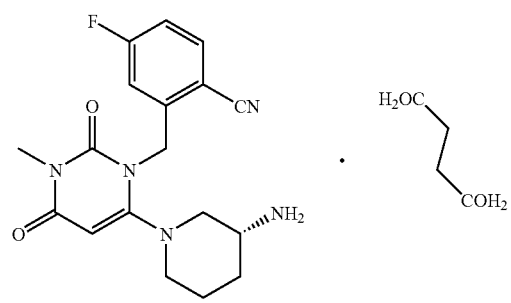

where at least a portion of Compound I is present in the composition in a form selected from the group consisting of crystalline forms, Forms A to G, and an amorphous form, Amorphous Form.

Also provided are kits and other articles of manufacture with compositions comprising Compound I where at least a portion of Compound I is present in the composition in a form selected from the group consisting of crystalline Forms A to G, and Amorphous Form.

Various methods are also provided including methods of making each of the disclosed forms; methods for manufacturing pharmaceutical compositions comprising Compound I where at least a portion of Compound I is present in the composition in a form selected from the group consisting of crystalline Forms A to G, and Amorphous Form; and methods of using compositions comprising Compound I where at least a portion of Compound I is present in the composition in a form selected from the group consisting of crystalline Forms A to G, and Amorphous Form.

As one will appreciate, depending on how a composition comprising a given compound is produced and then, once produced, how the composition is stored and manipulated, will influence the crystalline content of the composition. Accordingly, it is possible for a composition to comprise no crystalline content or may comprise higher concentrations of crystalline content.

It is further noted that a compound may be present in a given composition in one or more different polymorphic forms, as well as optionally also being present as an amorphous material. This may be the result of (a) physically mixing two or more different polymorphic forms; (b) having two or more different polymorphic forms be generated from crystallization conditions; (c) having all or a portion of a given polymorphic form convert into another polymorphic form; (d) having all or a portion of a compound in an amorphous state convert into two or more polymorphic forms; as well as for a host of other reasons.

As can be seen, depending on how a composition comprising a compound is prepared, the percentage, by weight, of that compound in a given polymorphic form can vary from 0% to 100%. According to the present invention, compositions are provided where greater than 0.1%, 1%, 5%, 10%, 25%, 50%, 75%, 80%, 85%, 90%, 95%, 97%, or 99% or more of Compound I (by weight) is present in the composition in a form selected from the group consisting of Forms A to G, and Amorphous Form.

DEFINITIONS

"Crystalline", as the term is used herein, refers to a material, which may be hydrated and/or solvated, and has sufficient ordering of the chemical moiety to exhibit a discernable diffraction pattern by XRPD or other diffraction techniques. Often, a crystalline material that is obtained by direct crystallization of a compound dissolved in a solution or by inter-conversion of crystals obtained under different crystallization conditions, will have crystals that contain the solvent used in the crystallization, termed a crystalline solvate. Also, the specific solvent system and physical embodiment in which the crystallization is performed, collectively termed crystallization conditions, may result in the crystalline material having physical and chemical properties that are unique to the crystallization conditions, generally due to the orientation of the chemical moieties of the compound with respect to each other within the crystal and/or the predominance of a specific polymorphic form of the compound in the crystalline material.

Depending upon the polymorphic form(s) of the compound that are present in a composition, various amounts of the compound in an amorphous solid state may also be present, either as a side product of the initial crystallization, and/or a product of degradation of the crystals comprising the crystalline material. Thus, crystalline, as the term is used herein, contemplates that the composition may include amorphous content; the presence of the crystalline material among the amorphous material being detectably among other methods by the composition having a discernable diffraction pattern.

The amorphous content of a crystalline material may be increased by grinding or pulverizing the material, which is evidenced by broadening of diffraction and other spectral lines relative to the crystalline material prior to grinding. Sufficient grinding and/or pulverizing may broaden the lines relative to the crystalline material prior to grinding to the extent that the XRPD or other crystal specific spectrum may become undiscernable, making the material substantially amorphous or quasi-amorphous.

Continued grinding would be expected to increase the amorphous content and further broaden the XRPD pattern with the limit of the XRPD pattern being so broadened that it can no longer be discerned above noise. When the XRPD pattern is broadened to the limit of being indiscernible, the material may be considered no longer a crystalline material, but instead be wholly amorphous. For material having increased amorphous content and wholly amorphous material, no peaks should be observed that would indicate grinding produces another form.

"Amorphous", as the term is used herein, refers to a composition comprising a compound that contains too little crystalline content of the compound to yield a discernable pattern by XRPD or other diffraction techniques. Glassy materials are a type of amorphous material. Glassy materials do not have a true crystal lattice, and technically resembling very viscous non-crystalline liquids. Rather than being true solids, glasses may better be described as quasi-solid amorphous material.

"Broad" or "broadened", as the term is used herein to describe spectral lines, including XRPD, NMR and IR spectroscopy, and Raman spectroscopy lines, is a relative term that relates to the line width of a baseline spectrum. The baseline spectrum is often that of an unmanipulated crystalline form of a specific compound as obtained directly from a given set of physical and chemical conditions, including solvent composition and properties such as temperature and pressure. For example, broadened can be used to describe the spectral lines of a XRPD spectrum of ground or pulverized material comprising a crystalline compound relative to the material prior to grinding. In materials where the constituent molecules, ions or atoms, as solvated or hydrated, are not tumbling rapidly, line broadening is indicative of increased randomness in the orientation of the chemical moieties of the compound, thus indicative of an increased amorphous content. When comparisons are made between crystalline materials obtained via different crystallization conditions, broader spectral lines indicate that the material producing the relatively broader spectral lines has a higher level of amorphous material.

"About" as the term is used herein, refers to an estimate that the actual value falls within ±5% of the value cited.

"Forked" as the term is used herein to describe DSC endotherms and exotherms, refers to overlapping endotherms or exotherms having distinguishable peak positions.

Preparation and Characterization of the Polymorphs

A. Preparation of Compound I

Various methods may be used to synthesize Compound I. A representative method for synthesizing Compound I is provided in Example 1. It is noted, however, that other synthetic routes may also be used to synthesize Compound I including those disclosed in U.S. patent application Ser. No. 11/080, 992, filed Mar. 15, 2005, the disclosure of which is hereby incorporated by reference in its entirety.

B. Preparation of the Polymorphs of Compound I

General methods for precipitating and crystallizing a compound may be applied to prepare the various polymorphs described herein. These general methods are known to those skilled in the art of synthetic organic chemistry and pharmaceutical formulation, and are described, for example, by J. March, "*Advanced Organic Chemistry: Reactions, Mechanisms and Structure*," 4$^{th}$ Ed. (New York: Wiley-Interscience, 1992).

In general, a given polymorph of a compound may be obtained by direct crystallization of the compound or by crystallization of the compound followed by inter-conversion from another polymorphic form or from an amorphous form. Depending on the method by which a compound is crystallized, the resulting composition may contain different amounts of the compound in crystalline form as opposed to as an amorphous material. Also, the resulting composition may contain differing mixtures of different polymorphic forms of the compound.

Compositions comprising a higher percentage of crystalline content (e.g., forming crystals having fewer lattice defects and proportionately less glassy material) are generally prepared when using conditions that favor slower crystal formation, including slow solvent evaporation and those affecting kinetics. Crystallization conditions may be appropriately adjusted to obtain higher quality crystalline material as necessary. Thus, for example, if poor crystals are formed under an initial set of crystallization conditions, the solvent temperature may be reduced and ambient pressure above the solution may be increased relative to the initial set of crystallization conditions in order to slow down crystallization.

Precipitation of a compound from solution, often affected by rapid evaporation of solvent, is known to favor the compound forming an amorphous solid as opposed to crystals. A compound in an amorphous state may be produced by rapidly evaporating solvent from a solvated compound, or by grinding, pulverizing or otherwise physically pressurizing or abrading the compound while in a crystalline state.

Compound I as prepared by the method described in Example 1 may be used as the starting material for preparation of all other polymorphic forms. The methods for testing the solubility of Compound I are described in Example 2, and the solubilities of Compound I in various solvents are summarized in Table A of Example 2. Poor solubility was observed in most solvents with the exceptions of dimethyl formamide (DMF), methanol, trifluoroethanol (TFE), water, and water:solvent mixtures.

Methods by which the various polymorphic forms may be prepared are described in Subsection A, Example 3. Specific methods by which Forms A-G, and Amorphous Form may be prepared are described in Tables B and C of Example 3. Methods useful for forming Form A, Form A+B, Form C, Form D, Form E, Form A+F, Form A+E+G, and Amorphous Form are described in Examples 3-10, respectively.

C. Polymorphs of Compound I

Seven crystalline forms and one amorphous solid were identified by conducting a polymorph screen (Example 3).

Described herein are Form A, Form B, Form C, Form D, Form E, Form F, Form G, and Amorphous Form of Compound I. Where possible, the results of each test for each different polymorph are provided. Forms A, C, D and E were prepared as pure forms. Forms B, F, and G were prepared as mixtures with Form A.

Various tests were performed in order to physically characterize the polymorphs of Compound I including X-ray powder diffraction (XRPD), differential scanning calorimetry (DSC), thermogravimetric analysis (TGA), hot stage microscopy, Fourier transform infrared spectroscopy (FT-IR), Fourier transform Raman spectrometry, linked thermogravimetric-infrared spectroscopy (TG-IR), solution proton nuclear magnetic resonance ($^1$H-NMR), solid state $^{13}$-carbon nuclear magnetic resonance ($^{13}$C-NMR), and moisture sorption and desorption analysis (M S/Des). Detailed experimental conditions for each of the analytical techniques are described in Example 3, Subsection B. The characterization of Forms A-G and Amorphous Form are described in Examples 1-18. Methods for testing the stabilities of the various forms of Compound I, and the conditions under which the polymeric forms interconvert are describe in Examples 19-25.

1. Form A

Form A may be prepared by crystallization from the various solvents and under the various crystallization conditions used during the polymorph screen (e.g., fast and slow evaporation, cooling of saturated solutions, slurries, and solvent/antisolvent additions). Tables B and C of Example 3 summarize the procedures by which Form A was prepared. For example, Form A was obtained by room temperature slurry of an excess amount of Compound I in acetone, acetonitrile, dichloromethane, 1,4-dioxane, diethyl ether, hexane, methanol, isopropanol, water, ethylacetate, tetrahydrofuran, toluene, or other like solvents on a rotating wheel for approximately 5 or 7 days. The solids were collected by vacuum filtration, and air dried in the hood. Also, Form A was precipitated from a methanol solution of Compound I by slow evaporation (SE).

Form A was characterized by XRPD, TGA, hot stage microscopy, IR, Raman spectroscopy, solution $^1$H-NMR, and solid state $^{13}$C-NMR.

FIG. 1 shows a characteristic XRPD spectrum (CuKα, λ=1.5418 Å) of Form A. The XRPD pattern confirmed that Form A was crystalline. Major X-Ray diffraction lines expressed in °2θ and their relative intensities are summarized in Table 1.

TABLE 1

Characteristic XRPD Peaks (CuKα) of Form A

| Peak No. | 2θ (°) | d-spacing | Intensity | I/I$_o$ |
|---|---|---|---|---|
| 1 | 4.80 | 18.40 | 91 | 3 |
| 2 | 11.31 | 7.82 | 2382 | 80 |
| 3 | 11.91 | 7.43 | 1416 | 48 |
| 4 | 12.86 | 6.88 | 266 | 9 |
| 5 | 14.54 | 6.09 | 1009 | 34 |
| 6 | 15.81 | 5.60 | 1457 | 49 |
| 7 | 16.83 | 5.26 | 522 | 18 |
| 8 | 17.59 | 5.04 | 299 | 10 |
| 9 | 18.11 | 4.89 | 91 | 3 |
| 10 | 19.26 | 4.60 | 816 | 27 |
| 11 | 19.52 | 4.54 | 642 | 22 |
| 12 | 20.32 | 4.37 | 178 | 6 |
| 13 | 21.04 | 4.22 | 996 | 34 |
| 14 | 21.80 | 4.07 | 174 | 6 |
| 15 | 22.32 | 3.98 | 2969 | 100 |
| 16 | 23.42 | 3.80 | 127 | 4 |
| 17 | 23.83 | 3.73 | 1025 | 35 |
| 18 | 24.78 | 3.59 | 181 | 6 |
| 19 | 25.28 | 3.52 | 684 | 23 |
| 20 | 25.84 | 3.45 | 120 | 4 |
| 21 | 26.14 | 3.41 | 352 | 12 |
| 22 | 26.63 | 3.34 | 477 | 16 |
| 23 | 27.62 | 3.23 | 342 | 12 |
| 24 | 27.84 | 3.20 | 303 | 10 |
| 25 | 28.14 | 3.17 | 274 | 9 |
| 26 | 29.39 | 3.04 | 132 | 4 |
| 27 | 29.87 | 2.99 | 255 | 9 |
| 28 | 30.27 | 2.95 | 183 | 6 |
| 29 | 31.60 | 2.83 | 163 | 5 |
| 30 | 31.88 | 2.80 | 166 | 6 |
| 31 | 32.44 | 2.76 | 106 | 4 |
| 32 | 33.86 | 2.65 | 123 | 4 |
| 33 | 34.51 | 2.60 | 141 | 5 |
| 34 | 35.87 | 2.50 | 305 | 10 |
| 35 | 36.36 | 2.47 | 133 | 4 |
| 36 | 37.31 | 2.41 | 146 | 5 |
| 37 | 38.64 | 2.33 | 129 | 4 |
| 38 | 39.49 | 2.28 | 90 | 3 |

The above set of XRPD peak positions or a subset thereof can be used to identify Form A. One subset comprises peaks at about 11.31, 11.91, 12.86, 14.54, 15.81, 16.83, 17.59, 19.26, 19.52, 21.04, 22.32, 26.63, and 29.87° 2θ. Another subset comprises peaks at about 11.31, 11.91, 19.26, 21.04, and 22.32° 2θ; the peaks of this subset show no shoulder peaks or peak split greater than 0.2° 2θ. Another subset comprises peaks at about 11.31, 11.91 and 22.32° 2θ.

Figure 2:
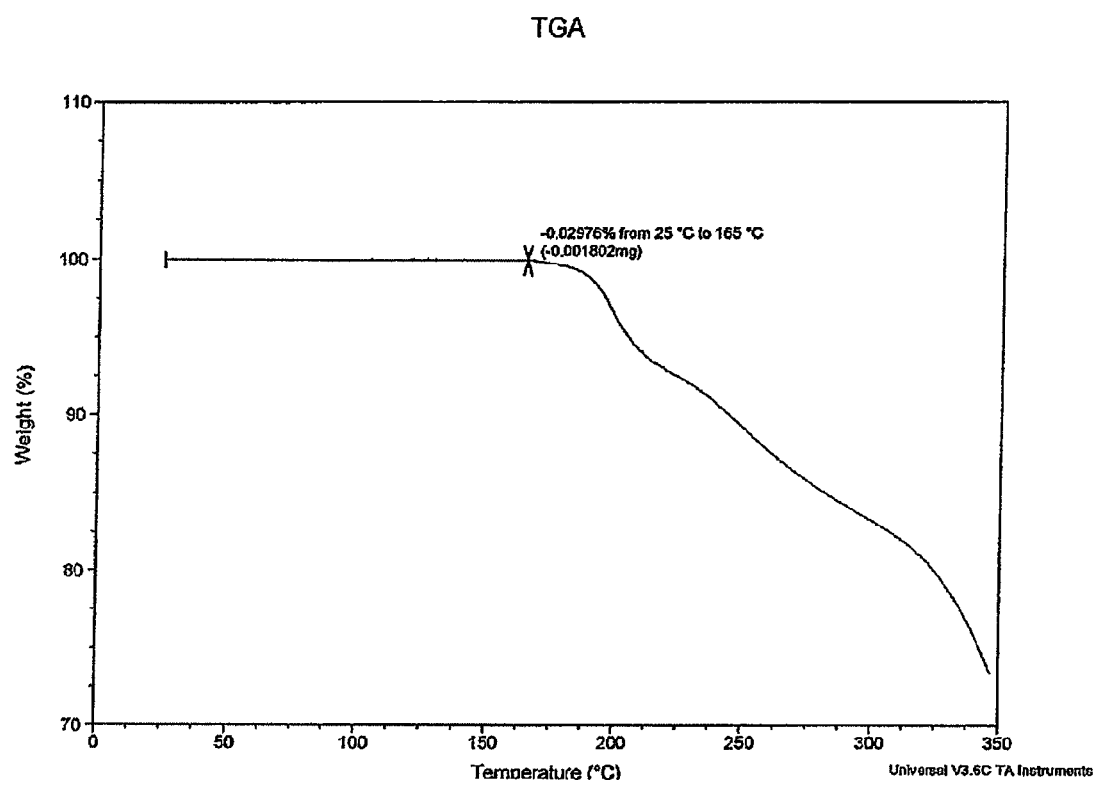
FIG. 2 is a characteristic thermgravimetric analysis (TGA) thermogram of Form A.

FIG. 2 is a TGA thermogram of Form A. TGA analysis showed that Form A exhibited insignificant weight loss when heated from 25° C. to 165° C.; this result is indicative that Form A was an anhydrous solid.

Figure 3:
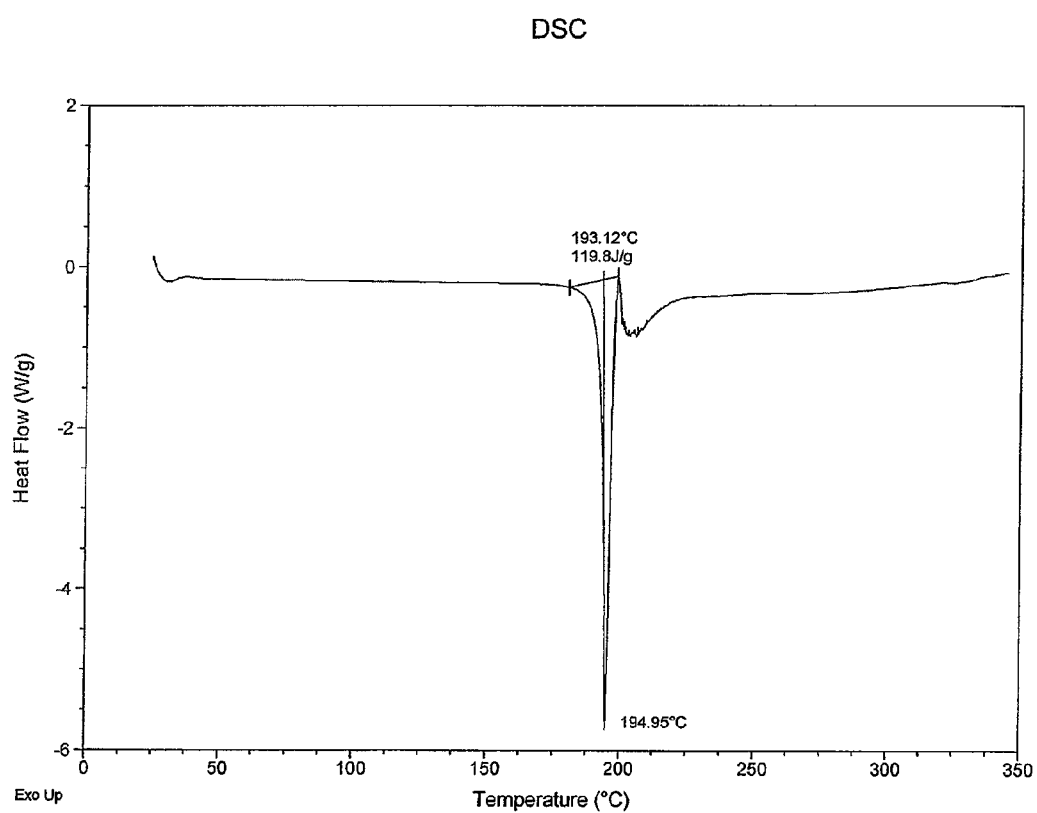
FIG. 3 is a characteristic differential scanning calorimetric (DSC) thermogram of Form A.
Figure 4A:
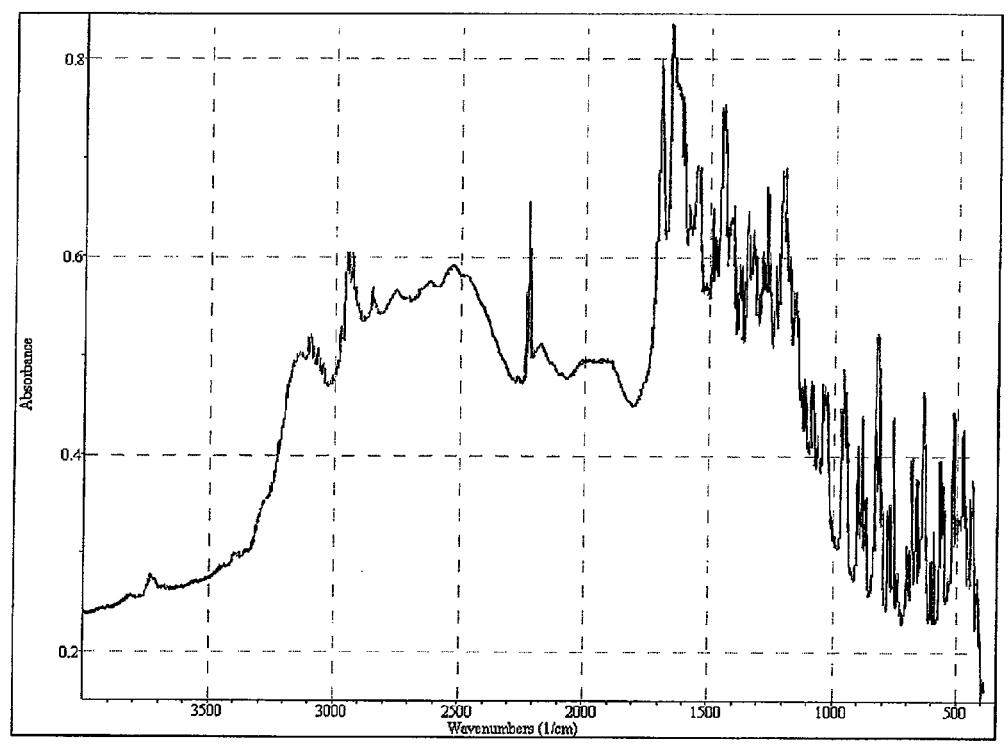
FIG. 4A is a characteristic Fourier transform infrared absorption (FT-IR) spectrum (4000-400 wavenumbers (cm-1)) of Form A.
Figure 4B:
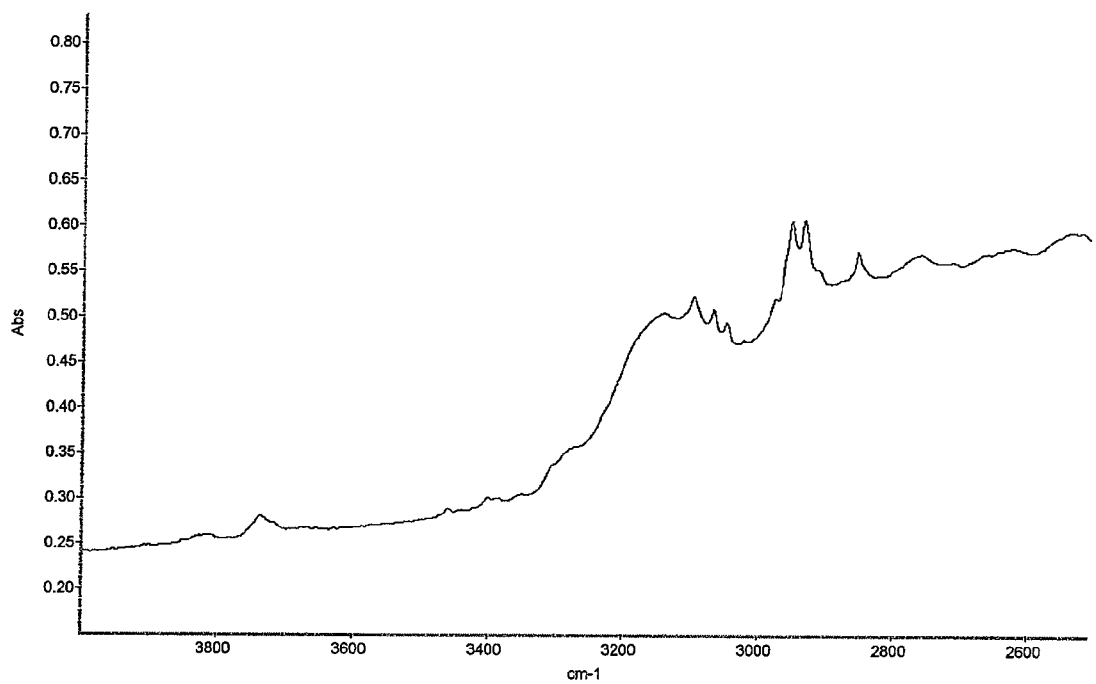
FIG. 4B is an expansion (4000-2500 cm-1) of the FT-IR spectrum of FIG. 4A.
Figure 4C:
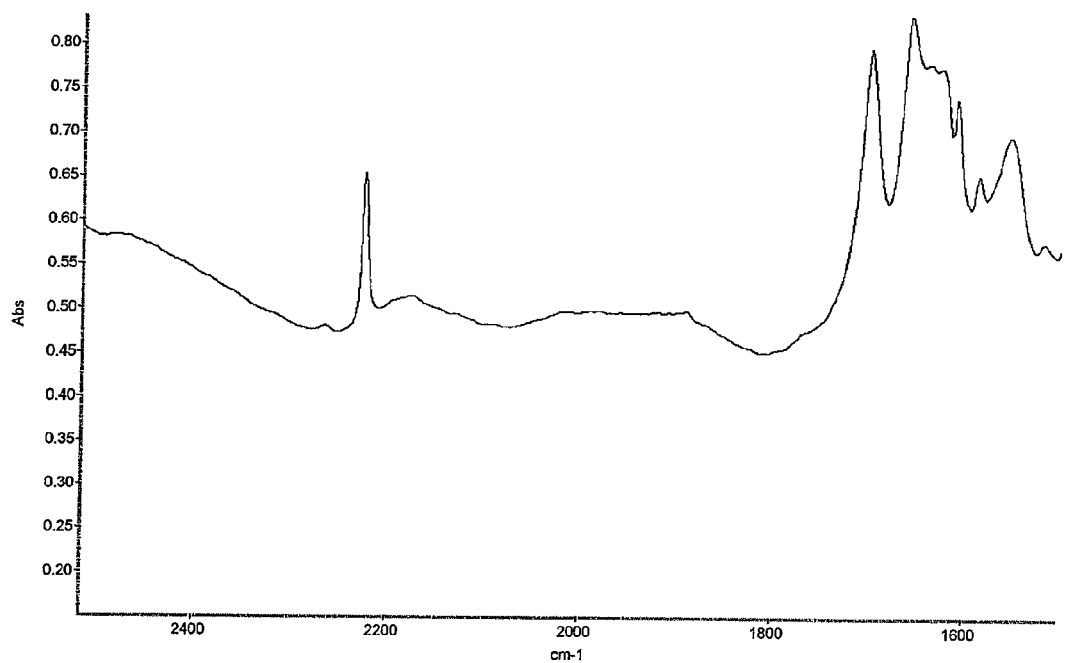
FIG. 4C is an expansion (2500-1500 cm-1) of the FT-IR spectrum of FIG. 4A.
Figure 4D:
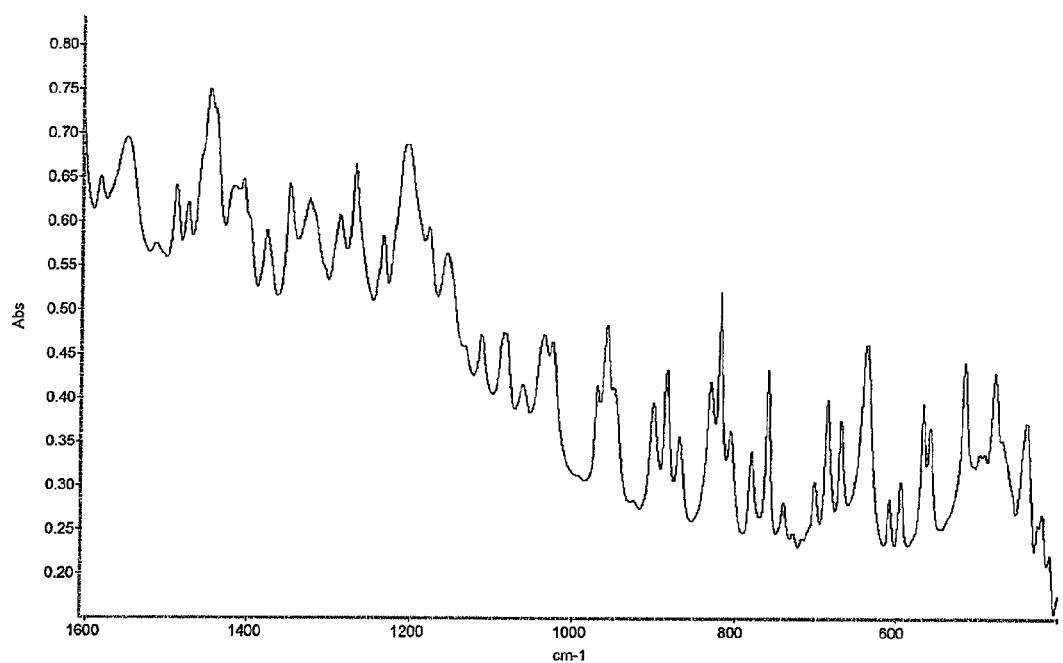
FIG. 4D is an expansion (1600-400 cm-1) of the FT-IR spectrum of FIG. 4A.
Figure 5A:
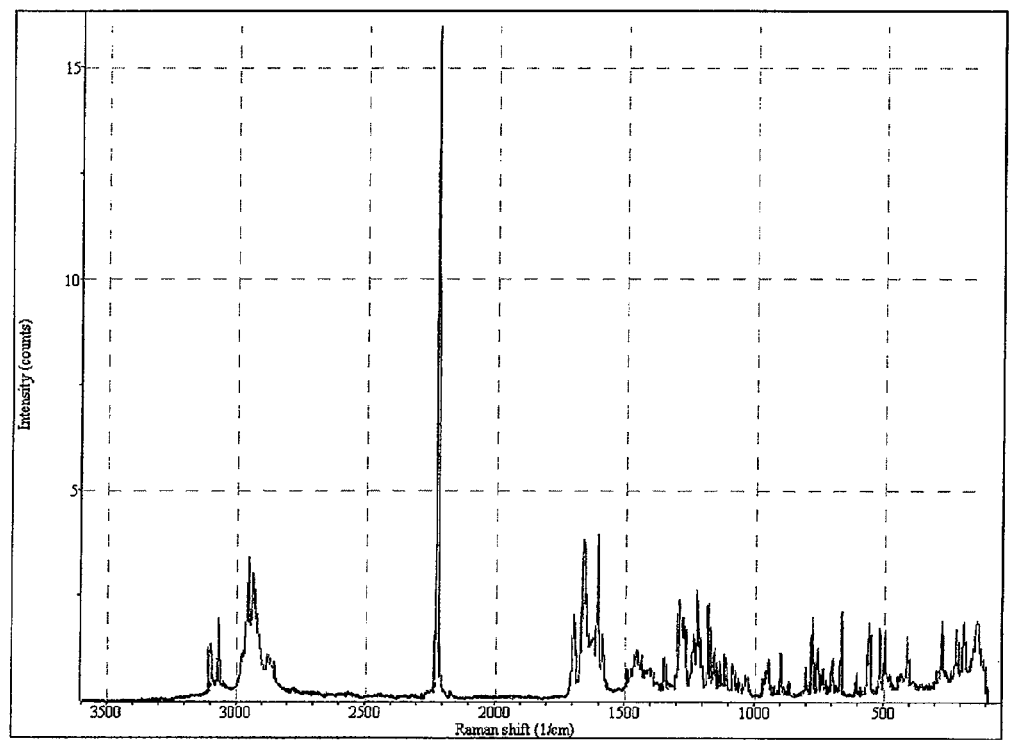
FIG. 5A is a characteristic FT-Raman spectrum (3600-0 cm-1) of Form A.
Figure 5B:
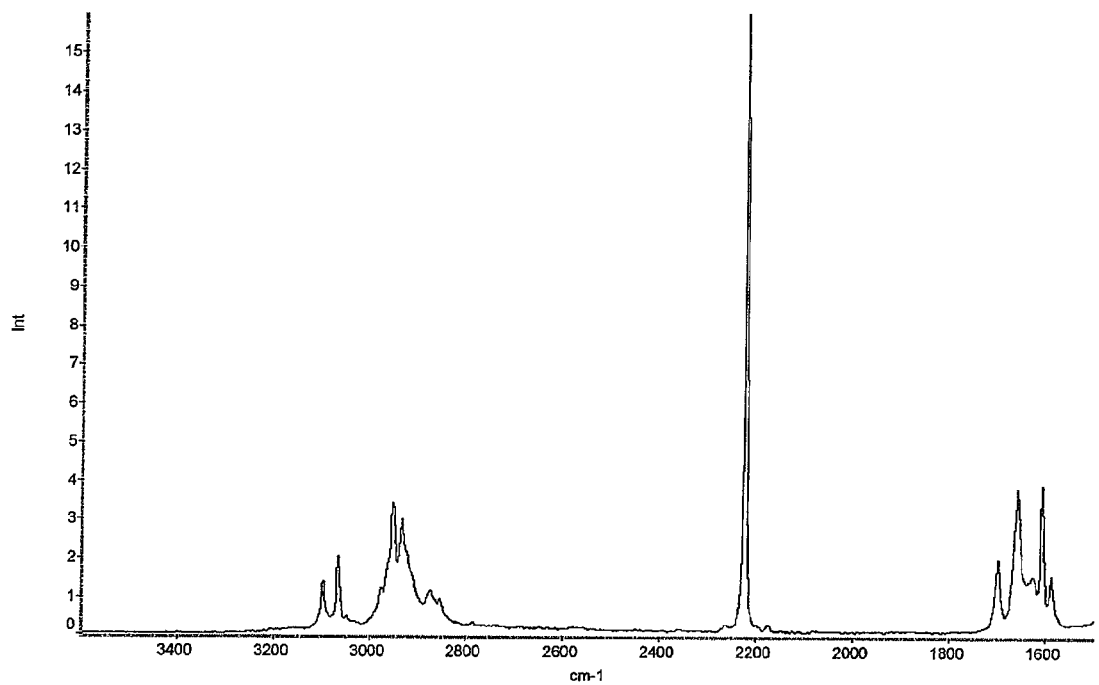
FIG. 5B is an expansion (3600-1500 cm-1) of the FT-Raman spectrum of FIG. 5A.
Figure 5C:
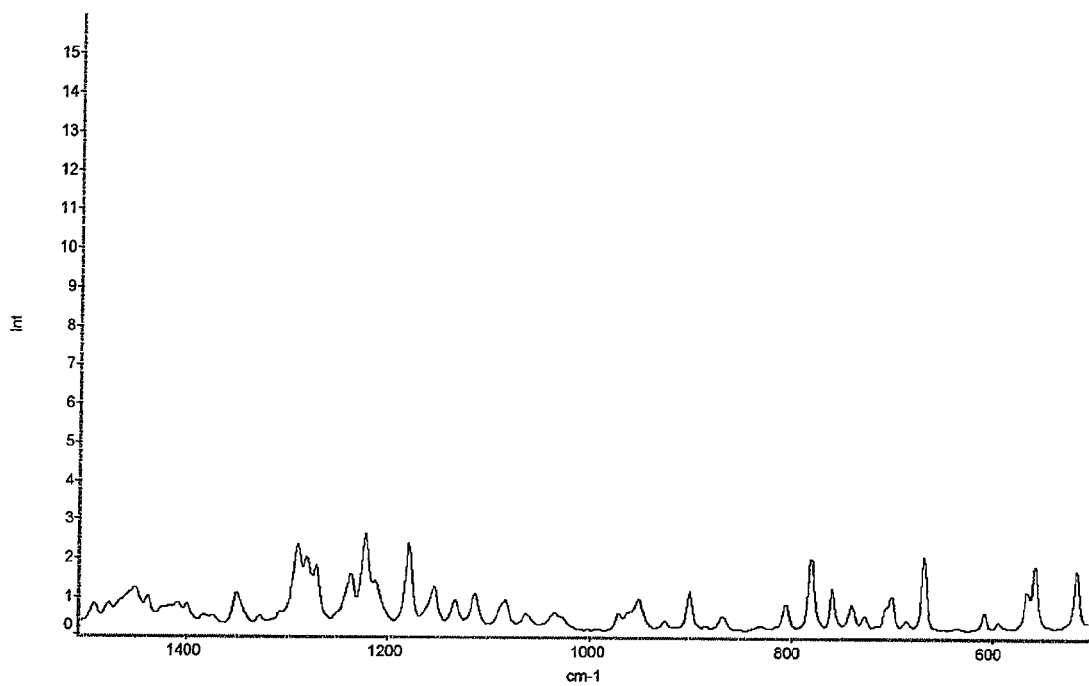
FIG. 5C is an expansion (1500-500 cm-1) of the FT-Raman spectrum of FIG. 5A.
Figure 5D:
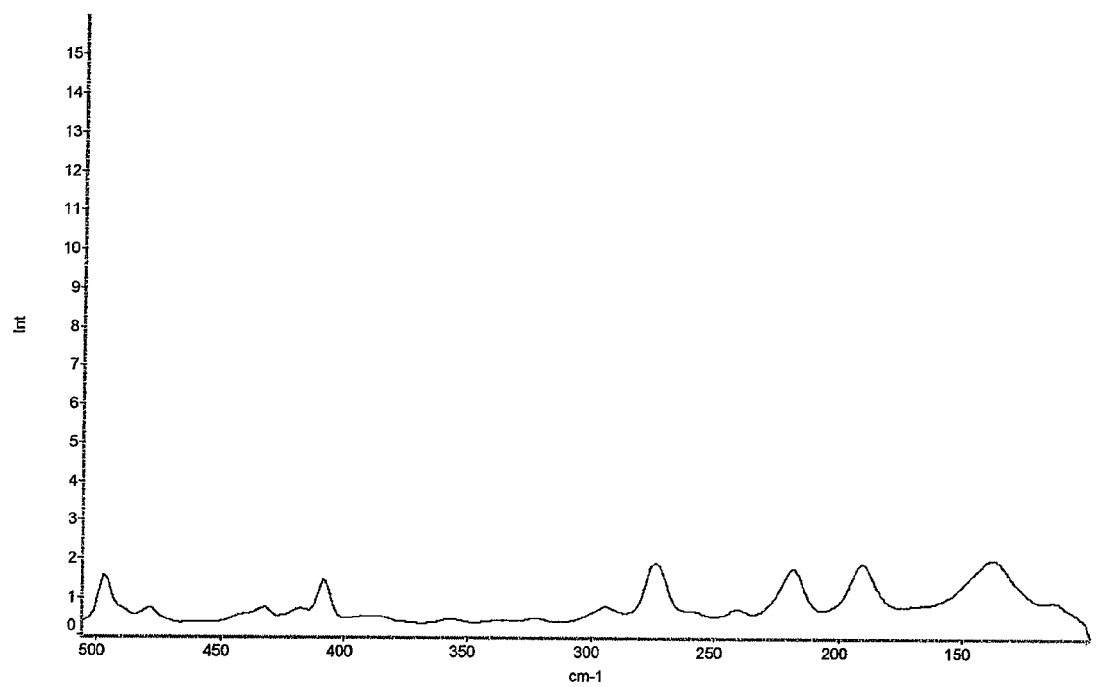
FIG. 5D is an expansion (500-100 cm-1) of the FT-Raman spectrum of FIG. 5A.

FIG. 3 shows a characteristic DSC thermogram of Form A. DSC analysis showed a single endothermic event occurred at approximately 195° C. (peak maximum). This endothermic event was confirmed by hot stage microscopy which showed the melting of Form A, which onset around 177° C. and the melting point estimated to be at approximately 184° C.

FIG. 4(A-D) shows a characteristic FT-IR spectrum of Form A. The major bands expressed in reciprocal wavelengths (wavenumber in cm$^{-1}$) are positioned at about 3815, 3736, 3675, 3460, 3402, 3141, 3098, 3068, 3049, 2953, 2934, 2854, 2760, 2625, 2536, 2481, 2266, 2225, 2176, 1990, 1890, 1699, 1657, 1638, 1626, 1609, 1586, 1553, 1517, 1492, 1478, 1450, 1419, 1409, 1380, 1351, 1327, 1289, 1271, 1236, 1206, 1180, 1158, 1115, 1087, 1085, 1064, 1037, 1027, 971, 960, 951, 926, 902, 886, 870, 831, 820, 806, 780, 760, 740, 728, 701, 685, 668, 637, 608, 594, 567, 558, and 516 cm$^{-1}$ (values rounded to the nearest whole number). This unique set of IR absorption bands or a subset thereof can be used to identify Form A. One such subset comprises absorption bands at about 3141, 3098, 3068, 3049, 2953, 2934, 2854, 2266, 2225, 1699, 1657, 1609, 1586, 1553, 1517, 1492, 1478, 1450, 1380, 1351, 1327, 1236, 1206, 1115, 1063, 902, 886, 870, 820, 780, 760, 685, 608, 594, and 516 cm$^{-1}$. Another subset comprises absorption bands at about 3141, 2953, 2934, 2854, 2266, 2225, 1699, 1657, 1450, 1206, 886, 760, 685, 594, and 516 cm$^{-1}$. Yet another subset comprises absorption bands at about 3141, 2953, 2934, 2266, 1699, 1657, 1450, and 1206 cm$^{-1}$.

FIG. 5(A-D) shows a characteristic Raman spectrum of Form A. The major Raman bands expressed in reciprocal wavelengths (wavenumber in cm$^{-1}$) are positioned at about 3100, 3068, 3049, 2977, 2954, 2935, 2875, 2855, 2787, 2263, 2225, 2174, 1698, 1659, 1626, 1607, 1586, 1492, 1478, 1451, 1439, 1409, 1400, 1382, 1351, 1328, 1290, 1281, 1271, 1237, 1223, 1213, 1180, 1155, 1134, 1115, 1084, 1063, 1035, 971, 952, 926901, 868, 805, 780, 759, 740, 727, 701, 686, 669, 609, 594, 566, 558, 516, 487, 479, 433, 418, 409, 294, 274, 241, 218, 191 and 138 cm$^{-1}$ (values rounded to the nearest whole number). This unique set of Raman bands or a subset thereof may be used to identify Form A. One such subset comprises Raman bands at about 2954, 2935, 2225, 1698, 1659, and 1607 cm$^{-1}$. Another subset comprises Raman bands at about 3068, 2954, 2935, 2225, 1698, 1659, 1607, 1586, 1223, 1180, 901, 780, 759, 669, and 516 cm$^{-1}$. Yet another subset comprises Raman bands at about 3100, 3068, 2225, 1698, 1659, 1607, 1586, 1351, 1237, 1223, 1180, 1155, 1134, 1115, 1063, 952, 926, 901, 868, 805, 780, 759, 740, 669, 609, and 516 cm$^{-1}$.

Figure 6:
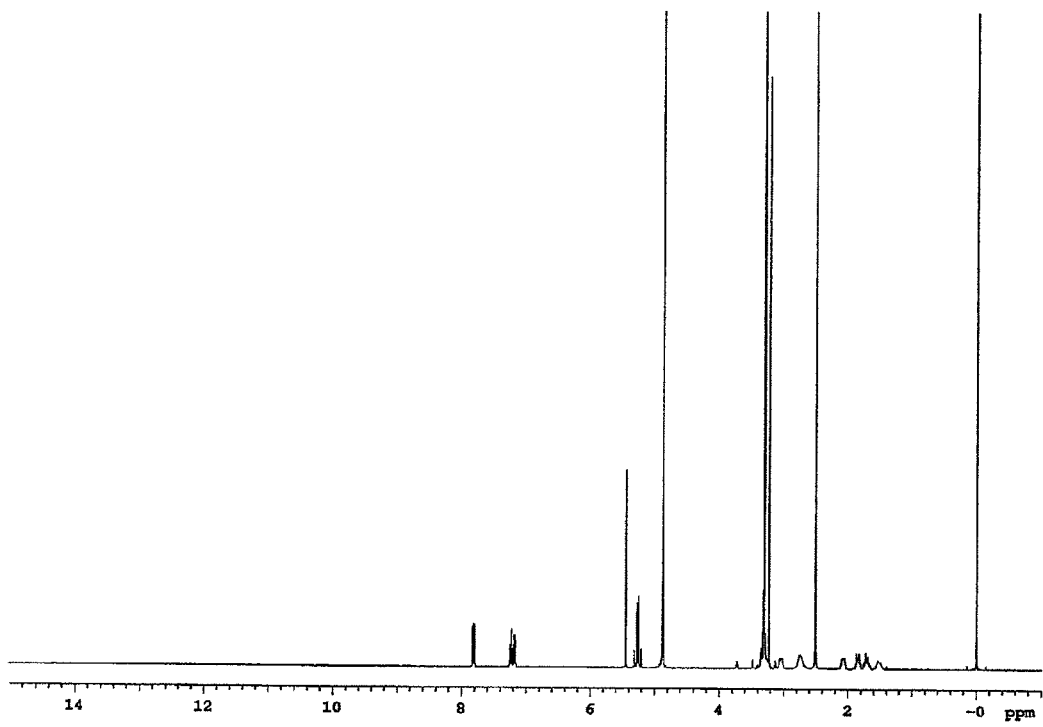
FIG. 6 is a solution proton nuclear magnetic resonance ($^1$H NMR) spectrum of Form A.
Figure 7:
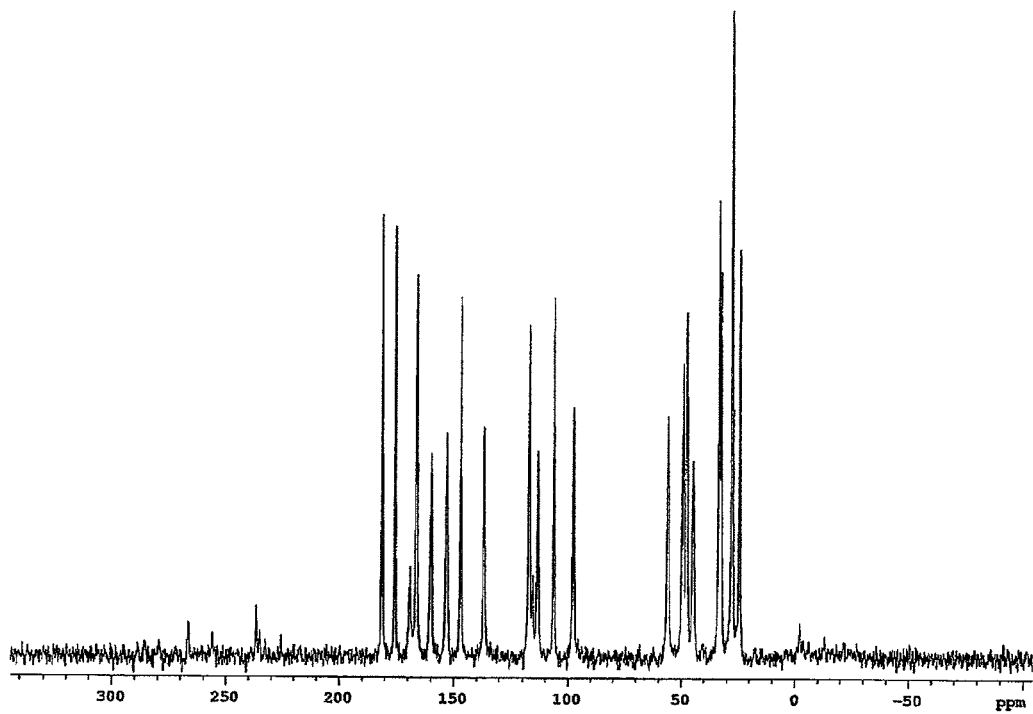
FIG. 7 is a solid state Carbon-13 nuclear magnetic resonance ($^{13}$C NMR) spectrum of Form A.

Form A was further characterized by solution $^1$H NMR and solid-state $^{13}$-carbon NMR. The spectra are reported in FIGS. 6 and 7, respectively. Chemical assignments were not performed; however, the spectra are consistent with the known chemical structure of Compound I.

A relative humidity stressing study (Example 19) showed that after storing under approximately 58% and 97% relative humidity for 29 days, Form A did not exhibit form changes as evidenced by XRPD. Additional relative humidity stressing studies, studies showed that Form B and Amorphous Form also converted to Form A.

Based on the above available characterization data, Form A was anhydrous and stable at ambient conditions.

2. Form B

Form B was prepared as a mixture with Form A (hereinafter refers to as "Form A+B") (Example 5). Form A+B was characterized by XRPD, TGA, DSC, hot stage microscopy, TG-IR, and moisture sorption/desorption analysis.

Figure 8:
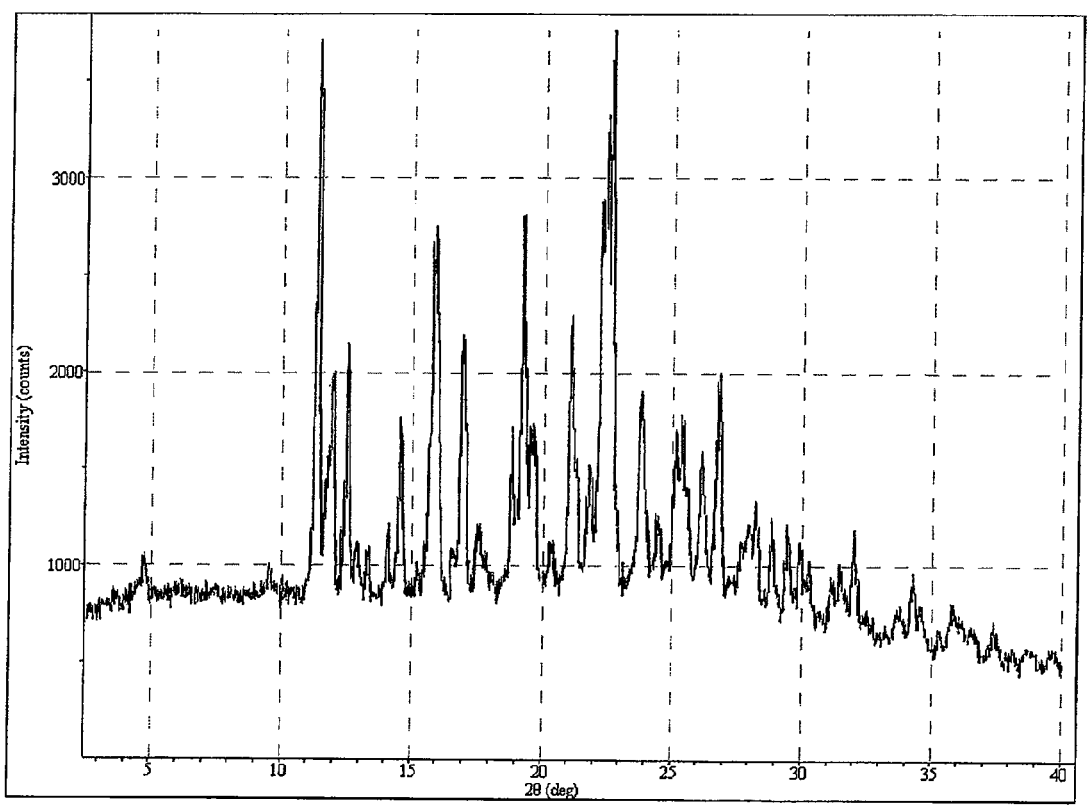
FIG. 8 is a characteristic XRPD spectrum of a mixture of Form A and Form B (Form A+B).

The XRPD pattern of Form A+B displayed in FIG. 8 confirmed that Form A+B was crystalline. The characteristic diffraction lines expressed in °2θ (CuKα, λ=1.5418 Å) and their relative intensity are summarized in Table 2 below.

TABLE 2

Characteristic XRPD Peaks (CuKα) of Form A + B

| Peak No. | 2θ (°) | d-spacing | Intensity | I/I$_o$ |
|---|---|---|---|---|
| 1 | 4.69 | 18.82 | 146 | 10 |
| 2 | 9.53 | 9.28 | 71 | 5 |
| 3 | 11.32 | 7.81 | 1121 | 74 |
| 4 | 11.87 | 7.45 | 605 | 40 |
| 5 | 12.51 | 7.07 | 483 | 32 |
| 6 | 13.29 | 6.66 | 91 | 6 |
| 7 | 14.05 | 6.30 | 130 | 9 |
| 8 | 14.53 | 6.09 | 371 | 25 |
| 9 | 15.83 | 5.59 | 1062 | 70 |
| 10 | 16.92 | 5.24 | 646 | 43 |
| 11 | 17.60 | 5.03 | 156 | 10 |
| 12 | 18.83 | 4.71 | 279 | 18 |
| 13 | 19.19 | 4.62 | 907 | 60 |
| 14 | 19.59 | 4.53 | 478 | 32 |
| 15 | 20.33 | 4.36 | 92 | 6 |
| 16 | 21.10 | 4.21 | 646 | 43 |
| 17 | 21.79 | 4.08 | 259 | 17 |
| 18 | 22.44 | 3.96 | 1513 | 100 |
| 19 | 23.80 | 3.74 | 542 | 36 |
| 20 | 24.46 | 3.64 | 160 | 11 |
| 21 | 25.27 | 3.52 | 505 | 33 |
| 22 | 26.12 | 3.41 | 349 | 23 |
| 23 | 26.74 | 3.33 | 520 | 34 |
| 24 | 27.93 | 3.19 | 262 | 17 |
| 25 | 28.80 | 3.10 | 177 | 12 |
| 26 | 29.41 | 3.03 | 182 | 12 |
| 27 | 30.02 | 2.97 | 166 | 11 |
| 28 | 31.34 | 2.85 | 139 | 9 |
| 29 | 31.96 | 2.80 | 194 | 13 |
| 30 | 33.69 | 2.66 | 86 | 6 |
| 31 | 34.37 | 2.61 | 148 | 10 |
| 32 | 35.90 | 2.50 | 126 | 8 |

This unique set of XRPD peaks or a subset thereof can be used to identify Form A+B of Compound I. A subset set of peaks that is characteristic of Form B was obtained by subtracting the XRPD peak positions of Form A from those of Form A+B. This subset which may be used to identify the presence of Form B comprises peaks positioned at about 12.51, 18.83 and 24.46° 2θ.

Figure 12:
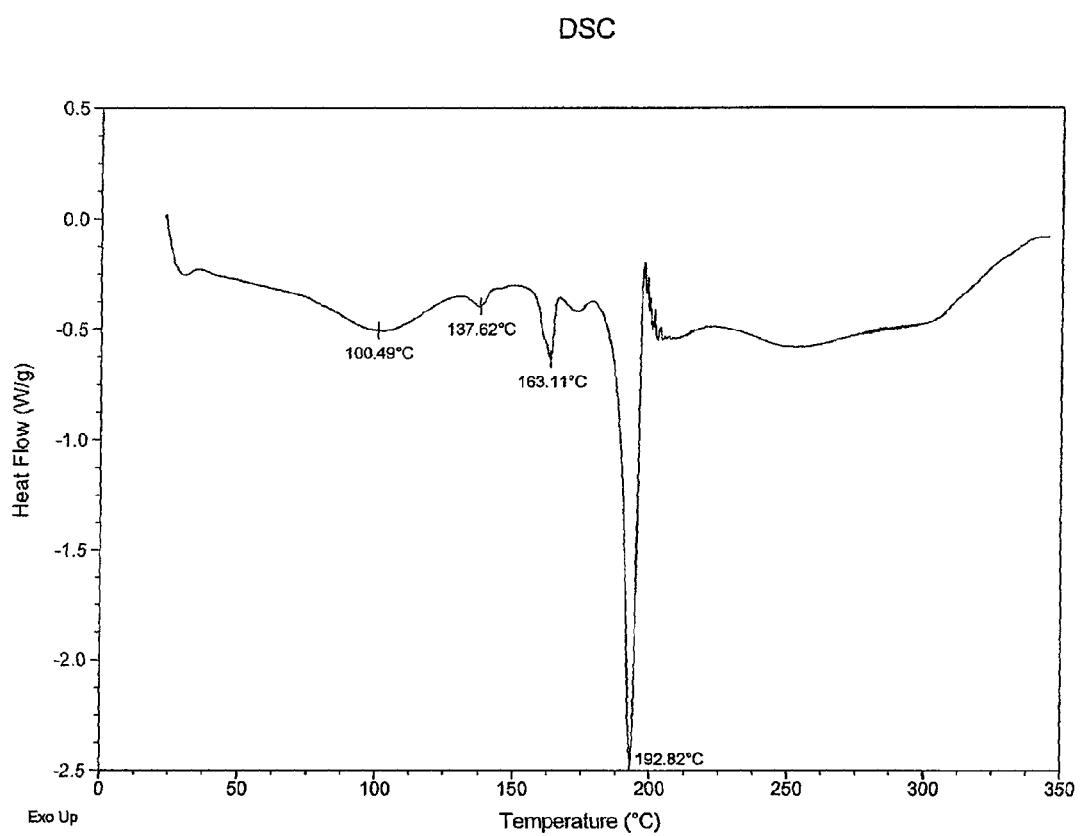
FIG. 12 is a characteristic DSC thermogram of Form A+B.

DSC analysis (FIG. 12) showed a broad endotherm at about 100° C., followed by small endotherms at 138° C. and 163° C. and a major endotherm at 193° C. These events suggested a slow desolvation/dehydration of Form A+B, and then melting of the desolvated Form B (163° C.) and Form A (193° C.).

These melting events were confirmed by hot stage microscopy which also showed portion of the particles melted at approximately 179° C. and the rest of the particles melted at 188° C. (micrographs not included).

Figure 9:
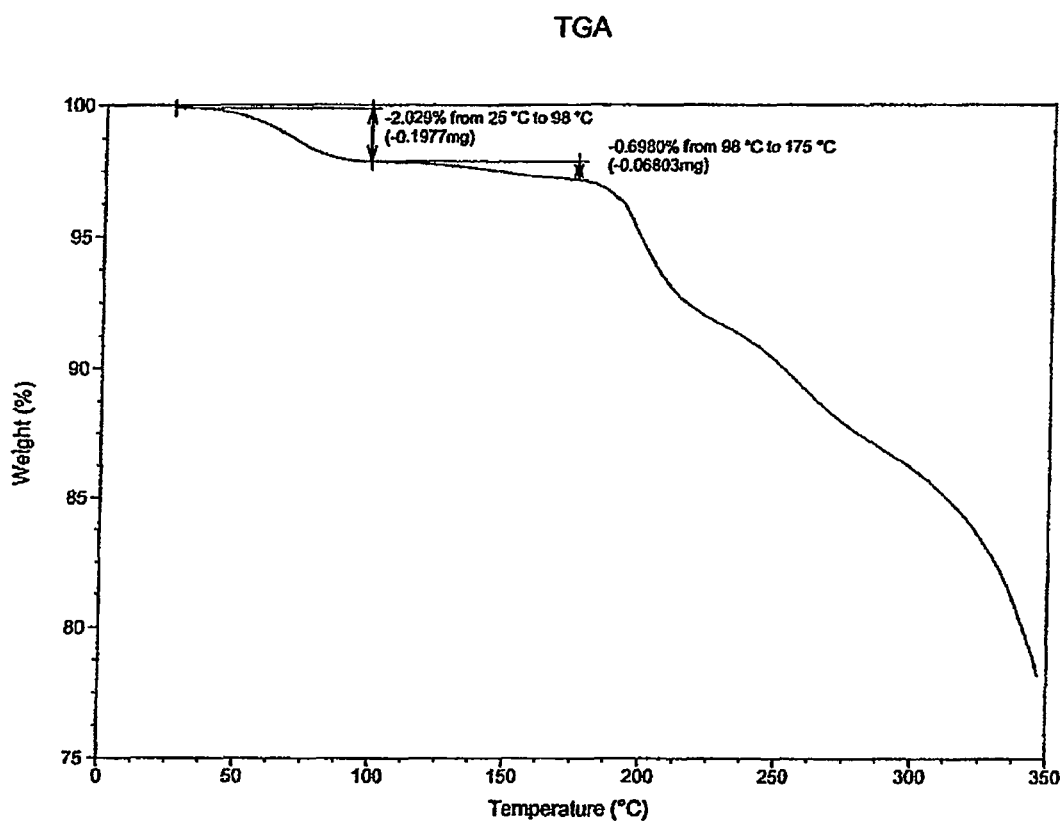
FIG. 9 is a characteristic TGA thermogram of Form A+B.

The TGA analysis (FIG. 9) indicated a 2.0% weight loss when Form A+B was heated from 25° C. to 98° C. and an additional 0.7% weight loss when heating continued from 98° C. to 175° C.

Figure 10:
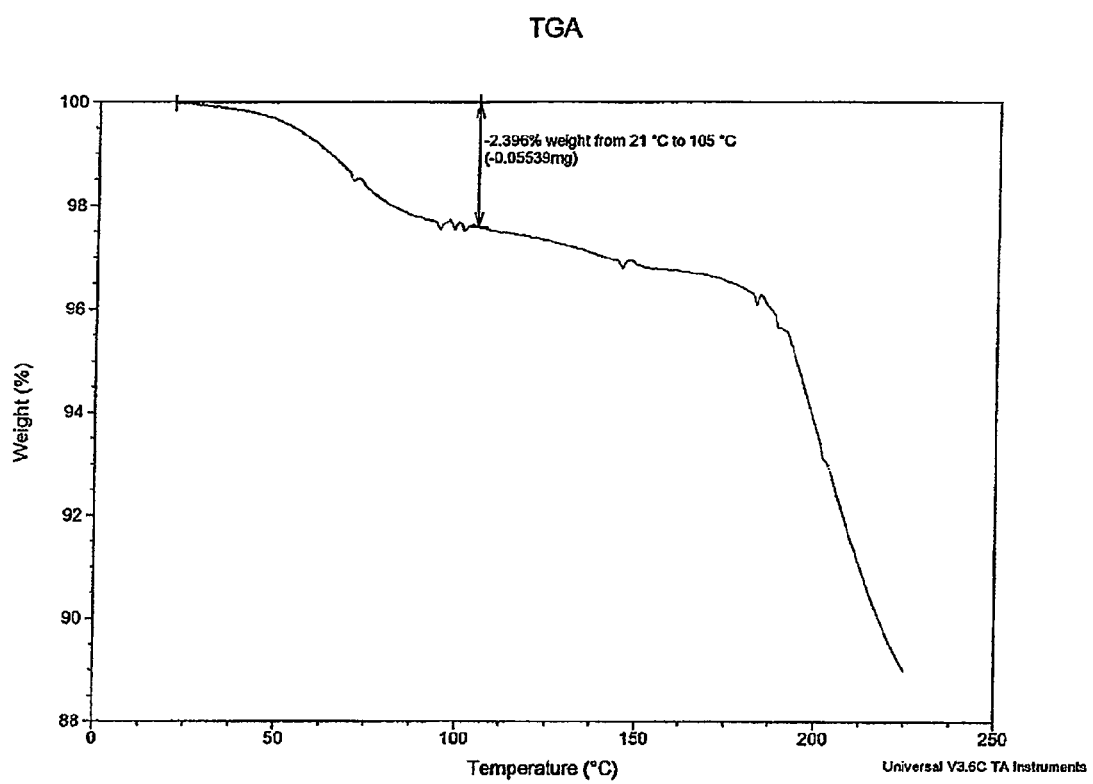
FIG. 10 is the TGA thermogram of a TG-IR analysis of Form A+B.
Figure 11:
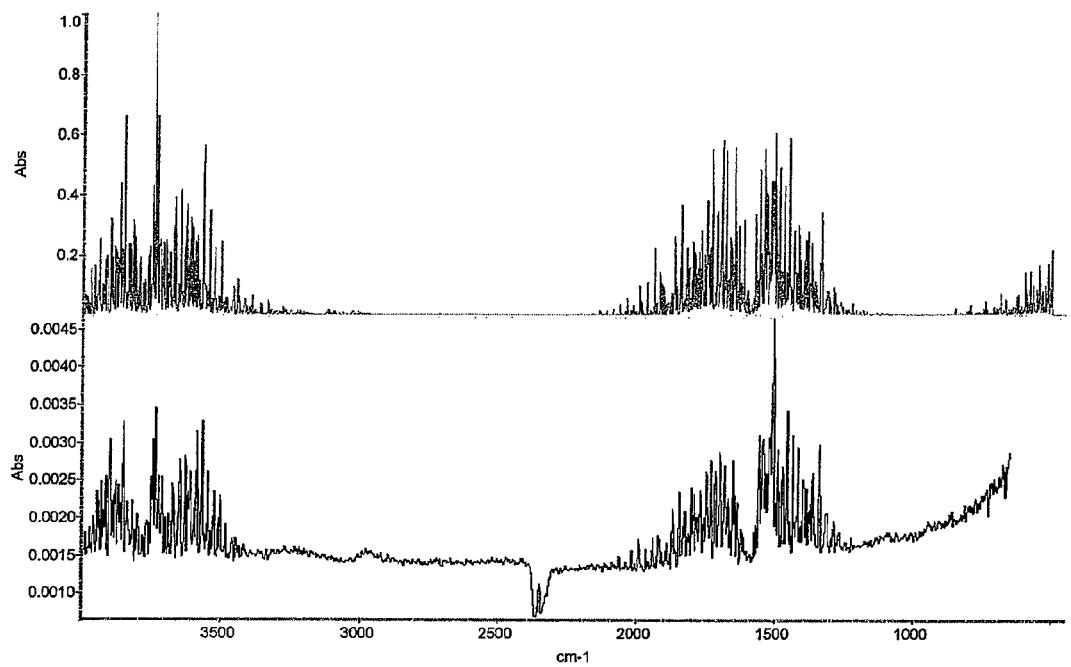
FIG. 11 is the linked (~5 minutes delay) IR spectrum of the TG-IR analysis of Form A+B. The bottom spectrum is the IR analysis of the volatiles evolved at ~5 minutes from the start of the TG analysis (FIG. 10). The top spectrum is a reference spectrum of water.

TG-IR (FIGS. 10 and 11) analysis revealed that the weight loss shown by TGA (FIG. 10) was due to the volatilization of water (FIG. 11). A 2.4% weight loss was consistent with approximately 0.5 to 1.0 moles of water. Since Form A was showed to be anhydrous, these results suggest that Form B was a hydrated solid form.

Figure 13:
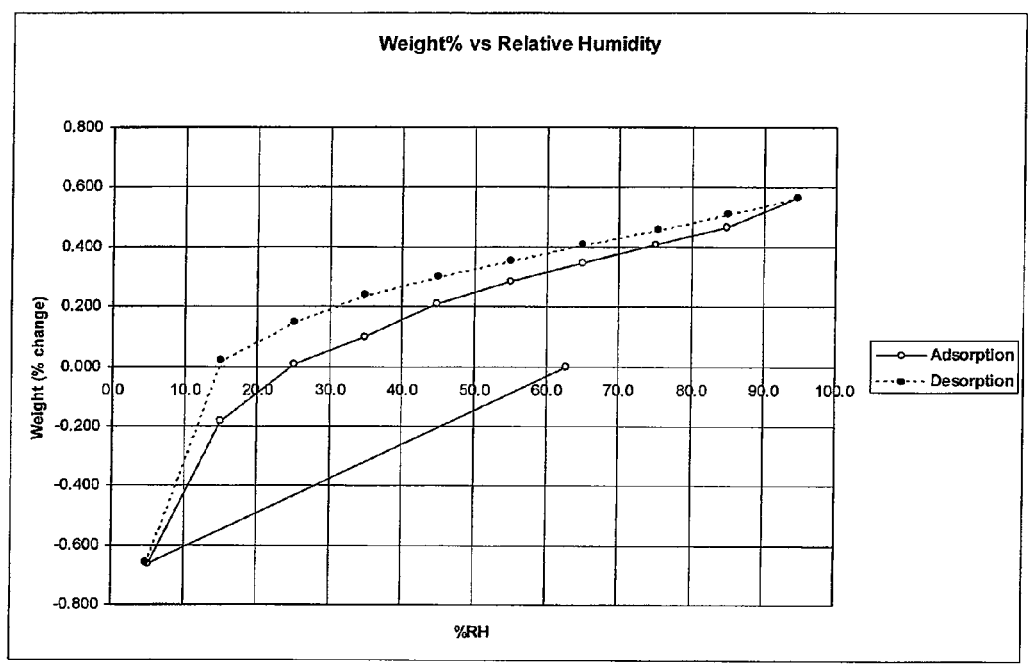
FIG. 13 is a moisture sorption and desorption isotherm of Form A+B.

Moisture sorption/desorption analysis (FIG. 13 and Example 23) showed a 0.7% weight loss on equilibration at 5% relative humidity. A reversible weight change of 1.2% weight was observed on sorption/desorption. XRPD analysis of the material remaining after the moisture sorption analysis was consistent with Form A.

Form B may be converted to Form A under dehydrating conditions. When Form A+B was stressed at 58% and 88% relative humidity for 23 days, the solids remained were Form A (Example 19). When Form A+B was exposed to ambient conditions for two days and in a vacuum oven at ambient temperature for one day, Form A+B converted to Form A (Example 20). When Form A+B was slurried in water and the water subsequently removed by evaporation, Form A+B converted to Form A (Example 21).

Based on the characterization data collected, Form B was a crystalline, hydrated solid.

3. Form C

Form C was prepared by precipitation from an IPA solution of Compound I by slow cooling (Example 5). XRPD confirmed that Form C was crystalline.

Figure 14:
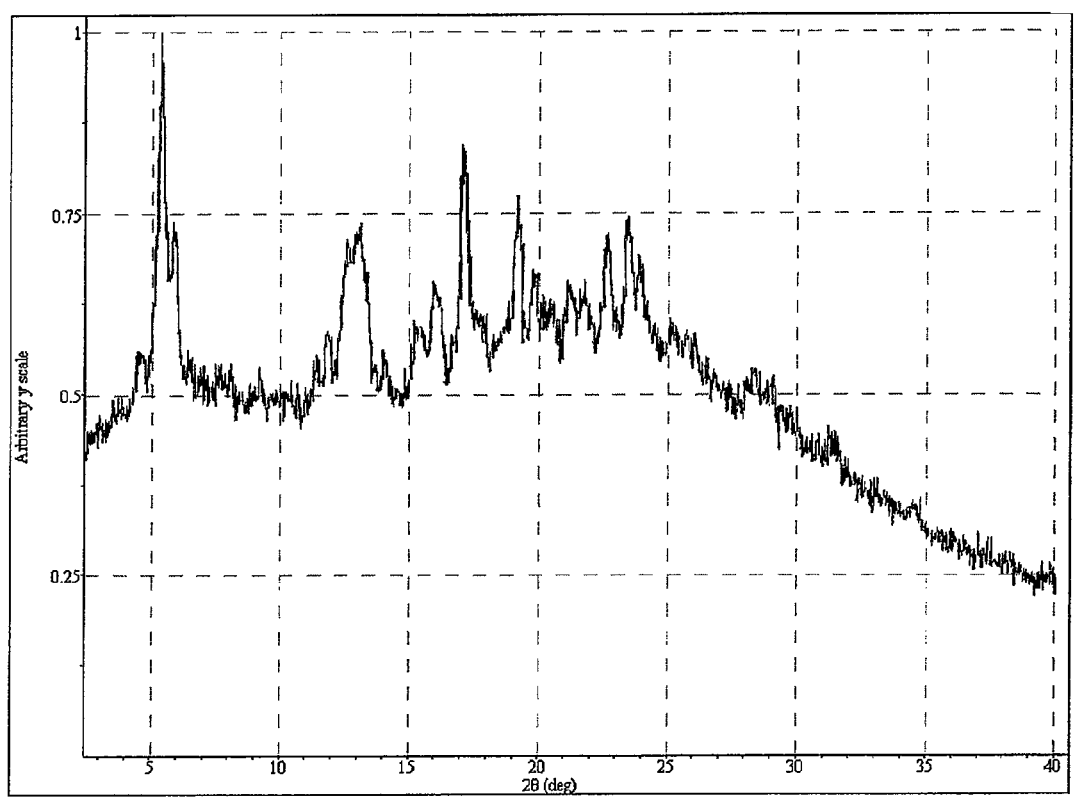
FIG. 14 is a characteristic XRPD spectrum of Form C.

The characteristic XRPD spectrum (CuKα, λ=1.5418 Å) of Form C is shown in FIG. 14. The major diffraction peaks expressed in °2θ and their relative intensities are summarized in Table 3 below.

TABLE 3

Characteristic XRPD Peaks (CuKα) of Form C.

| Peak No. | 2θ (°) | d-spacing | Intensity | I/I$_o$ |
|---|---|---|---|---|
| 1 | 4.39 | 20.13 | 143 | 16 |
| 2 | 5.44 | 16.24 | 885 | 100 |
| 3 | 6.07 | 14.56 | 318 | 36 |
| 4 | 11.63 | 7.60 | 136 | 15 |
| 5 | 12.87 | 6.87 | 540 | 61 |
| 6 | 15.72 | 5.63 | 210 | 24 |
| 7 | 17.12 | 5.17 | 419 | 47 |
| 8 | 19.18 | 4.62 | 281 | 32 |
| 9 | 20.13 | 4.41 | 133 | 15 |
| 10 | 21.43 | 4.14 | 161 | 18 |
| 11 | 22.61 | 3.93 | 247 | 28 |
| 12 | 23.66 | 3.76 | 343 | 39 |
| 13 | 25.42 | 3.50 | 135 | 15 |

This unique set of XRPD peak positions or a subset thereof can be used to identify Form C. Particularly useful for identification of Form C are peaks at about 5.44 and 6.07° 2θ because these peaks did not exhibit a shoulder or peak split greater than 0.2° 2θ.

4. Form D

Form D was precipitated by adding acetonitrile (a miscible antisolvent) to a water solution of Compound I (Example 6). The precipitates were characterized by solution $^1$H NMR, XRPD, TGA, DSC, TG-IR, and hot stage microscopy.

Solution $^1$H NMR data (spectrum not included) showed that Form D had the same chemical structure as Compound I.

Figure 15:
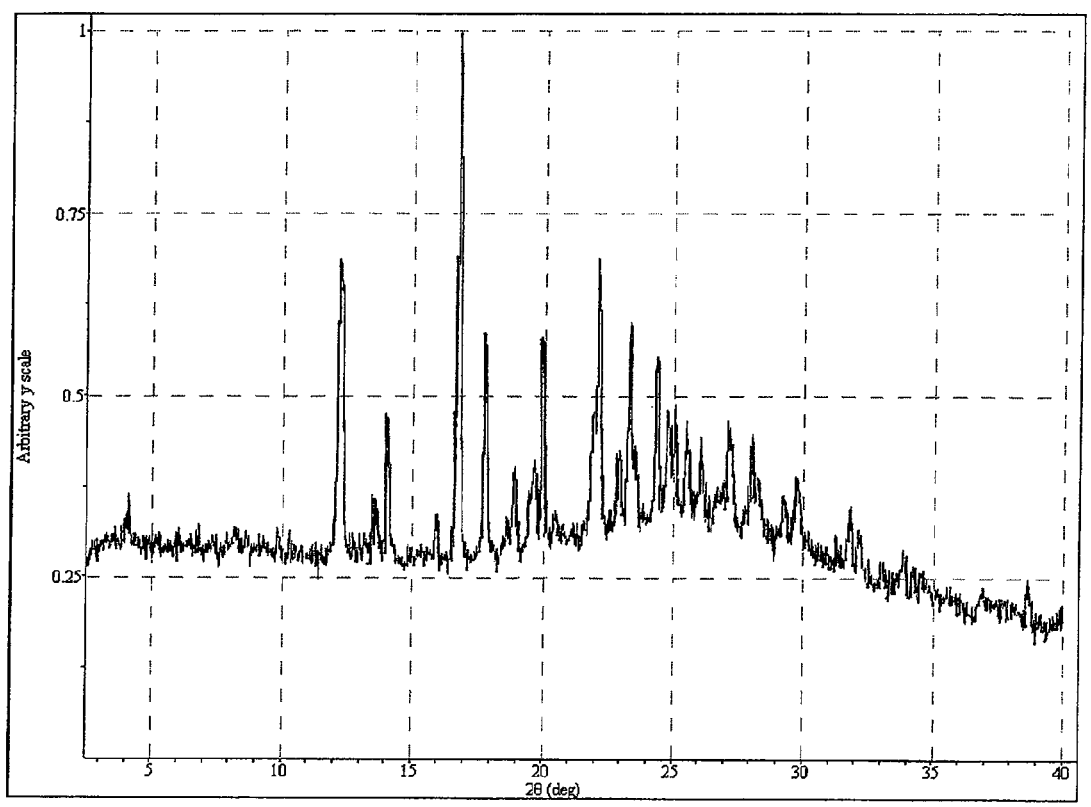
FIG. 15 is a characteristic XRPD spectrum of Form D.

The characteristic XRPD spectrum (CuKα) of Form D is shown in FIG. 15. The XRPD diffraction pattern confirmed that Form D was crystalline. The major diffraction peaks expressed in °2θ and their relative intensities are summarized in Table 4.

TABLE 4

Characteristic XRPD Peaks (CuKα) of Form D

| Peak No. | 2θ (°) | d-spacing | Intensity | I/I$_o$ |
|---|---|---|---|---|
| 1 | 4.06 | 21.73 | 110 | 8 |
| 2 | 12.19 | 7.25 | 787 | 59 |
| 3 | 13.45 | 6.58 | 123 | 9 |
| 4 | 13.61 | 6.50 | 120 | 9 |
| 5 | 14.04 | 6.30 | 351 | 26 |
| 6 | 15.91 | 5.57 | 123 | 9 |
| 7 | 16.71 | 5.30 | 1344 | 100 |
| 8 | 17.75 | 4.99 | 516 | 38 |

TABLE 4-continued

Characteristic XRPD Peaks (CuKα) of Form D

| Peak No. | 2θ (°) | d-spacing | Intensity | I/I$_o$ |
|---|---|---|---|---|
| 9 | 18.59 | 4.77 | 83 | 6 |
| 10 | 18.86 | 4.70 | 210 | 16 |
| 11 | 19.45 | 4.56 | 124 | 9 |
| 12 | 19.63 | 4.52 | 227 | 17 |
| 13 | 19.96 | 4.44 | 541 | 40 |
| 14 | 20.46 | 4.34 | 75 | 6 |
| 15 | 21.89 | 4.06 | 334 | 25 |
| 16 | 22.08 | 4.02 | 687 | 51 |
| 17 | 22.88 | 3.88 | 190 | 14 |
| 18 | 23.27 | 3.82 | 528 | 39 |
| 19 | 23.51 | 3.78 | 188 | 14 |
| 20 | 24.33 | 3.65 | 433 | 32 |
| 21 | 24.76 | 3.59 | 291 | 22 |
| 22 | 25.02 | 3.56 | 289 | 22 |
| 23 | 25.49 | 3.49 | 217 | 16 |
| 24 | 26.03 | 3.42 | 200 | 15 |
| 25 | 26.59 | 3.35 | 76 | 6 |
| 26 | 26.89 | 3.31 | 86 | 6 |
| 27 | 27.15 | 3.28 | 261 | 19 |
| 28 | 27.99 | 3.18 | 276 | 21 |
| 29 | 28.23 | 3.16 | 167 | 12 |
| 30 | 29.17 | 3.06 | 145 | 11 |
| 31 | 29.33 | 3.04 | 87 | 6 |
| 32 | 29.76 | 3.00 | 201 | 15 |
| 33 | 31.75 | 2.82 | 152 | 11 |
| 34 | 32.11 | 2.79 | 147 | 11 |
| 35 | 33.02 | 2.71 | 67 | 5 |
| 36 | 33.81 | 2.65 | 106 | 8 |
| 37 | 36.81 | 2.44 | 68 | 5 |
| 38 | 37.10 | 2.42 | 67 | 5 |
| 39 | 38.61 | 2.33 | 87 | 6 |

This above set of XRPD peak positions or a subset thereof can be used to identify Form D of Compound I. Particularly useful for identifying Form D are the subsets of peaks that comprise a peak located at about 24.33° 2θ and four other peaks selected from the group consisting of peaks at about 12.19, 14.04, 16.71, 17.75, 18.86, 19.96, 22.08, 22.88, 23.27, 25.02, 25.49, 26.03, and 27.99° 2θ. More particularly useful are the subsets of peaks that comprise a peak located at about 24.33° 2θ and four other peaks selected from the group consisting of peaks at about 12.19, 16.71, 22.08, 22.88, and 23.27° 2θ. Other subsets of peaks that are useful for identifying Form D are those comprising the peaks at about 12.19, 22.88 and 24.33° 2θ, ±0.2° 2θ.

Figure 16:
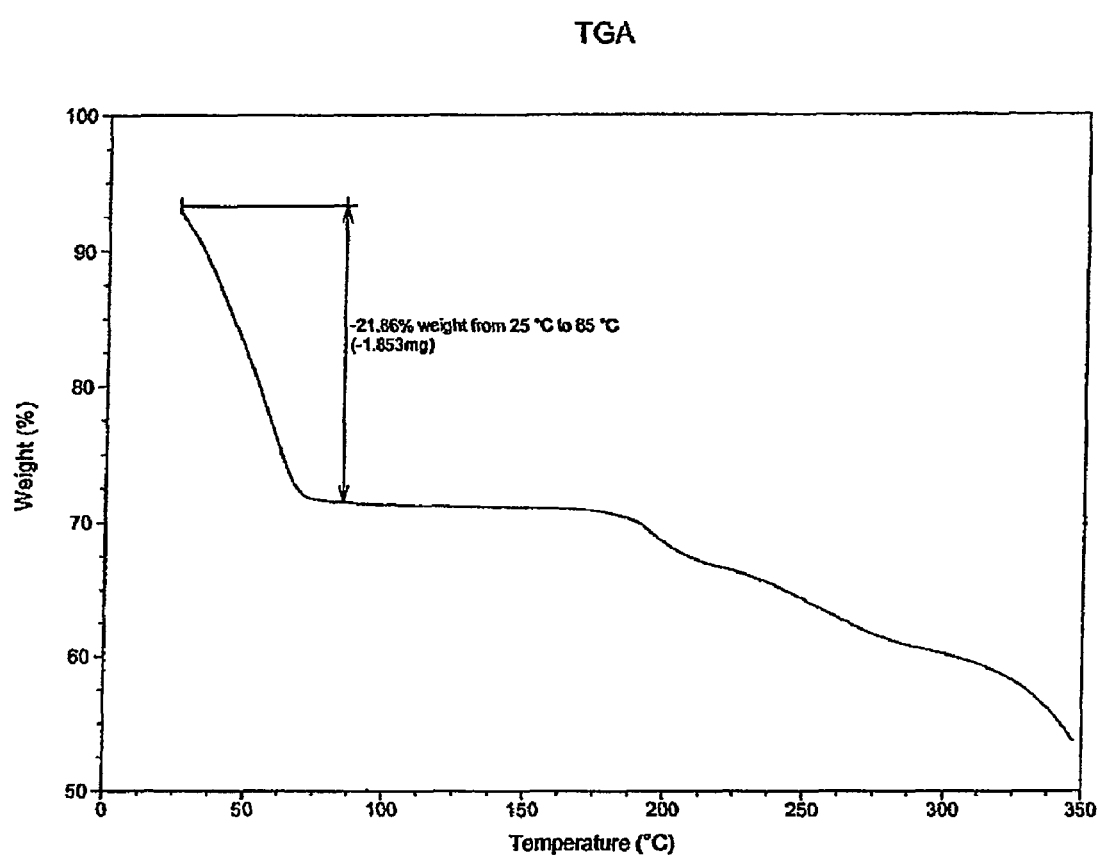
FIG. 16 is a characteristic TGA thermogram of Form D.

Form D was formed when the Amorphous Form was vapor stressed (Example 22). TGA analysis (FIG. 16) showed that Form D exhibited an approximately 8% weight loss on equilibration, followed by a 21.9% weight loss from 25° C. to 85° C. The approximately 30% total weight loss was consistent with approximately 11 moles of water.

Figure 17:
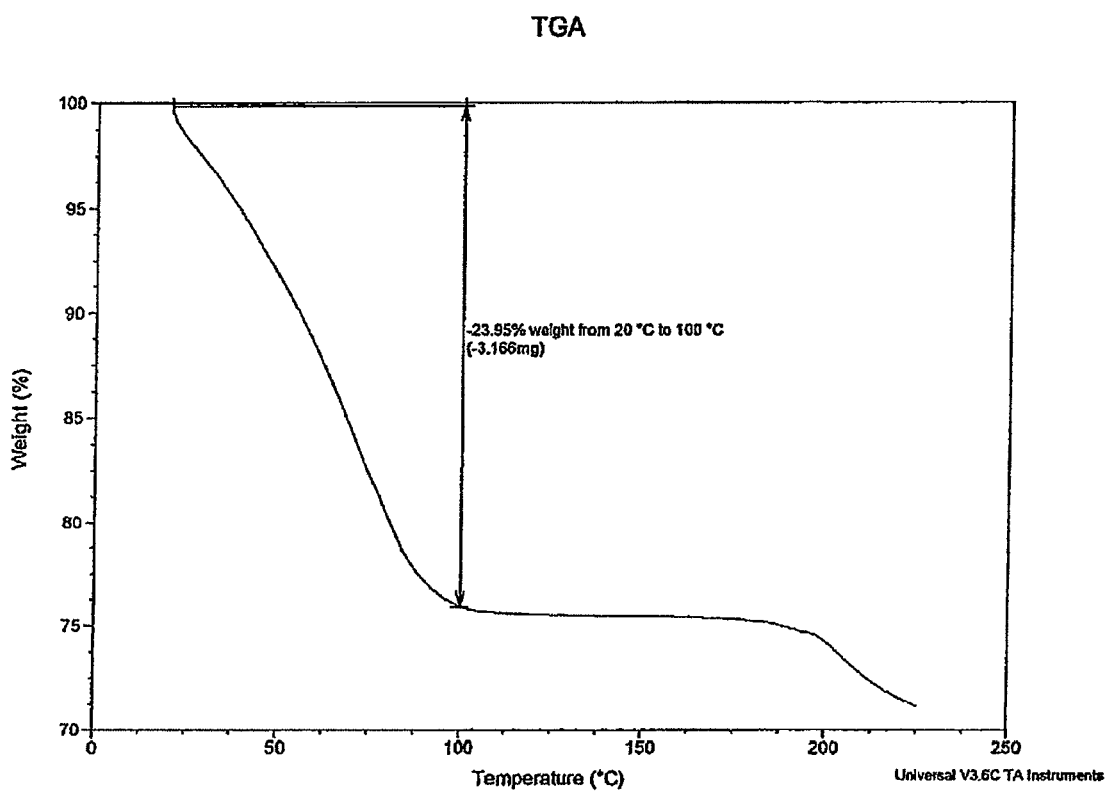
FIG. 17 is a TGA thermogram of a TG-IR analysis of Form D.
Figure 18:
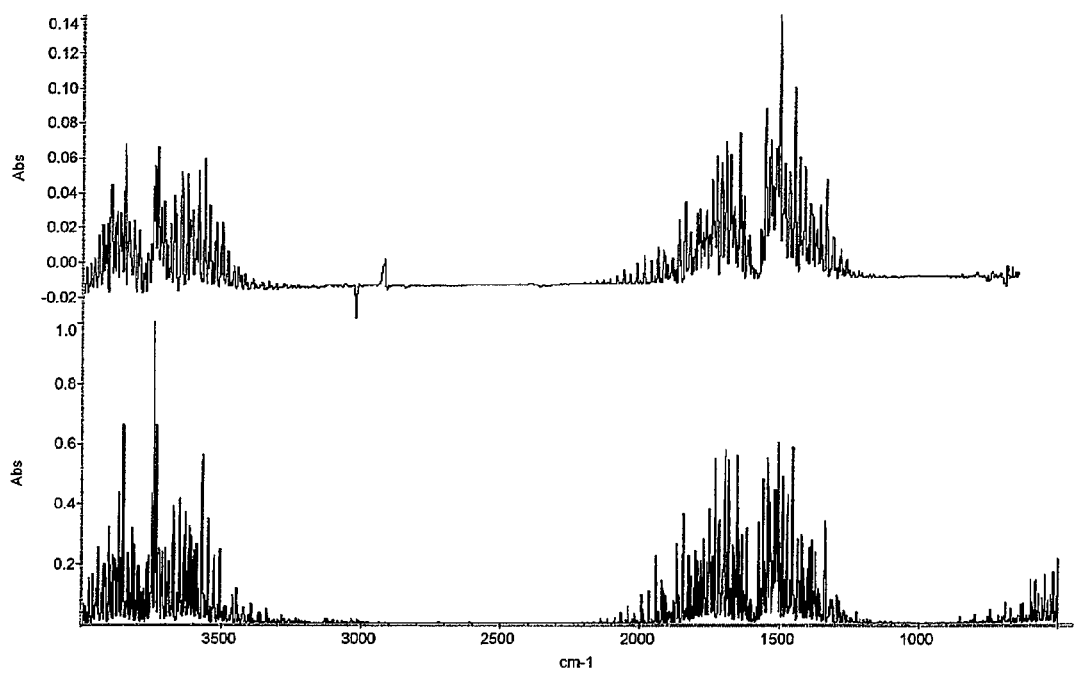
FIG. 18 is the linked IR spectrum (~5 minutes delay) of the TG-IR analysis of Form D. The top spectrum is the IR spectrum of the volatiles evolved at ~5 minutes from the start of the TG analysis (FIG. 17). The bottom spectrum is a reference spectrum of water.

Further, TG-IR analysis (FIGS. 17 and 18) confirms that the weight loss from 20° C. to 100° C. was due to volatilization of water.

DSC analysis of Form D (FIG. 19) showed multiple, broad endotherms with an apparent peak maximum at 88° C., followed by endotherms at approximately 107° C. and 192° C. The data suggested that the solid desolvated/dehydrated, melted and possibly converted to Form A with the subsequent melting of Form A upon continued heating.

Hot stage analysis showed the final melting of the solid at 192° C. (micrograph not included) which further substantiated that Form D converted to Form A which has a melting temperature of about 192° C.

In summary, the characterization data indicated that Form D was a crystalline, hydrated solid.

5. Form E

Form E was precipitated by the evaporation of a H₂O/ACN solvent/antisolvent solution of Compound I (Example 7). The precipitates were characterized by solution ¹H NMR, XRPD, TGA, DSC, TG-IR, hot stage microscopy, and moisture sorption/desorption analysis. Solution ¹H NMR data (spectrum not included) showed that Form E possessed the same chemical structure as Compound I.

Figure 20:
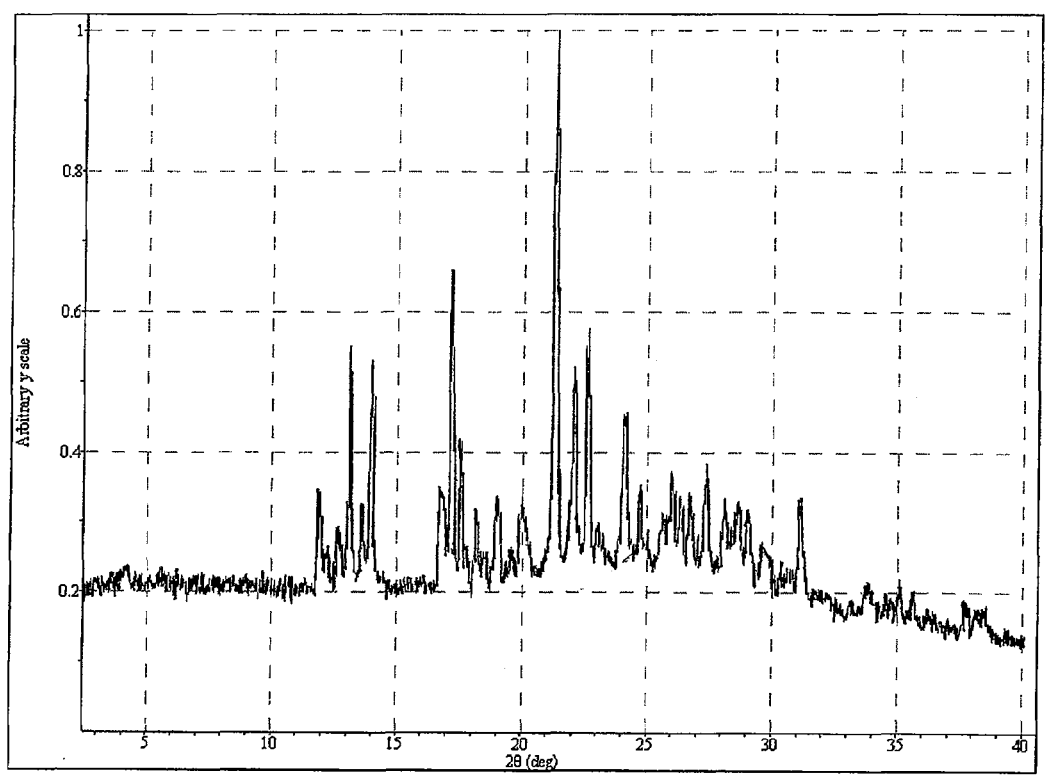
FIG. 20 is a characteristic XRPD spectrum of Form E.

The characteristic XRPD spectrum (CuKα, λ=1.5418 Å) of Form E is shown in FIG. 20. The XRPD diffraction pattern confirmed that Form E was crystalline. The major diffraction peaks expressed in °2θ, and their relative intensities are summarized in Table 5 below.

TABLE 5

Characteristic XRPD Peaks (CuKα) of Form E

| Peak No. | 2θ (°) | d-spacing | Intensity | I/I₀ |
|---|---|---|---|---|
| 1 | 11.90 | 7.43 | 292 | 16 |
| 2 | 12.17 | 7.27 | 121 | 7 |
| 3 | 12.66 | 6.99 | 187 | 10 |
| 4 | 13.10 | 6.75 | 727 | 39 |
| 5 | 13.59 | 6.51 | 266 | 14 |
| 6 | 13.94 | 6.35 | 676 | 37 |
| 7 | 16.78 | 5.28 | 306 | 17 |
| 8 | 17.15 | 5.17 | 1026 | 55 |
| 9 | 17.54 | 5.05 | 450 | 24 |
| 10 | 18.18 | 4.88 | 196 | 11 |
| 11 | 19.02 | 4.66 | 274 | 15 |
| 12 | 20.03 | 4.43 | 239 | 13 |
| 13 | 21.27 | 4.17 | 1849 | 100 |
| 14 | 22.03 | 4.03 | 659 | 36 |
| 15 | 22.61 | 3.93 | 744 | 40 |
| 16 | 23.02 | 3.86 | 121 | 7 |
| 17 | 24.06 | 3.70 | 476 | 26 |
| 18 | 24.70 | 3.60 | 270 | 15 |
| 19 | 25.60 | 3.48 | 145 | 8 |
| 20 | 25.95 | 3.43 | 285 | 15 |
| 21 | 26.31 | 3.38 | 219 | 12 |
| 22 | 26.70 | 3.34 | 191 | 10 |
| 23 | 27.34 | 3.26 | 336 | 18 |
| 24 | 28.08 | 3.18 | 247 | 13 |
| 25 | 28.41 | 3.14 | 128 | 7 |
| 26 | 28.61 | 3.12 | 241 | 13 |
| 27 | 29.00 | 3.08 | 242 | 13 |
| 28 | 29.70 | 3.01 | 114 | 6 |
| 29 | 31.10 | 2.87 | 314 | 17 |
| 30 | 33.76 | 2.65 | 118 | 6 |
| 31 | 34.48 | 2.60 | 95 | 5 |
| 32 | 35.04 | 2.56 | 127 | 7 |
| 33 | 35.58 | 2.52 | 122 | 7 |
| 34 | 37.65 | 2.39 | 117 | 6 |
| 35 | 38.10 | 2.36 | 93 | 5 |
| 36 | 38.42 | 2.34 | 93 | 5 |

The unique set of XRPD peak positions above or a subset thereof can be used to identify Form E. Such subsets of peaks may comprise any five peaks selecting from the group consisting of peaks at about 11.90, 12.66, 13.10, 13.59, 13.94, 17.15, 17.54, 21.27, 22.03, 22.61, 24.06, 24.70, 26.31, 27.34, and 31.10° 2θ. Other subsets of peaks that may be used to identify Form E include two peaks at about 21.27 and 17.15° 2θ, and three other peaks selected from the group consisting of peaks at about 11.90, 12.66, 13.10, 13.59, 13.94, 17.54, 22.03, 22.61, 24.06, 24.70, 26.31, 27.34, and 31.10° 2θ. Another subset of peaks that may be used for identifying Form E comprises peaks located at about 13.10, 13.94, 17.15, 21.27, 26.31 and 27.34° 2θ.

Figure 21:
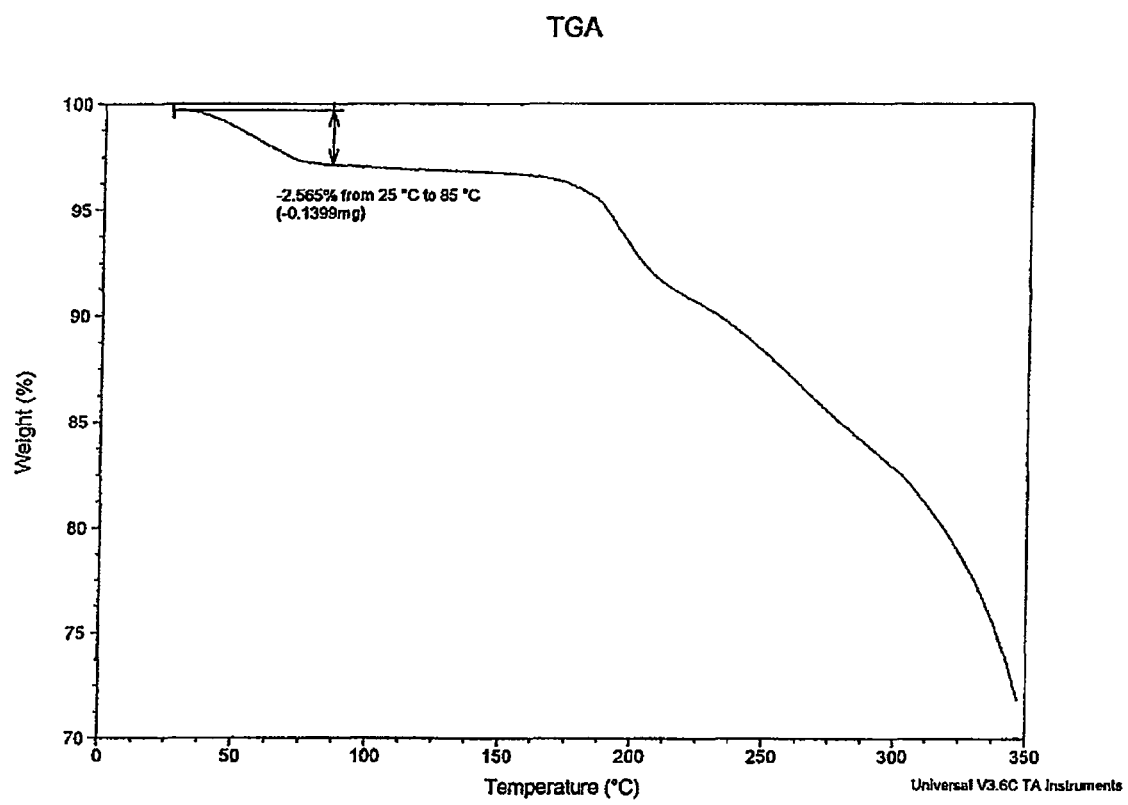
FIG. 21 is a characteristic TGA thermogram of Form E.

TGA analysis (FIG. 21) showed that Form E exhibited a 2.6% weight loss upon heating from 25° C. to 85° C.

Figure 22:
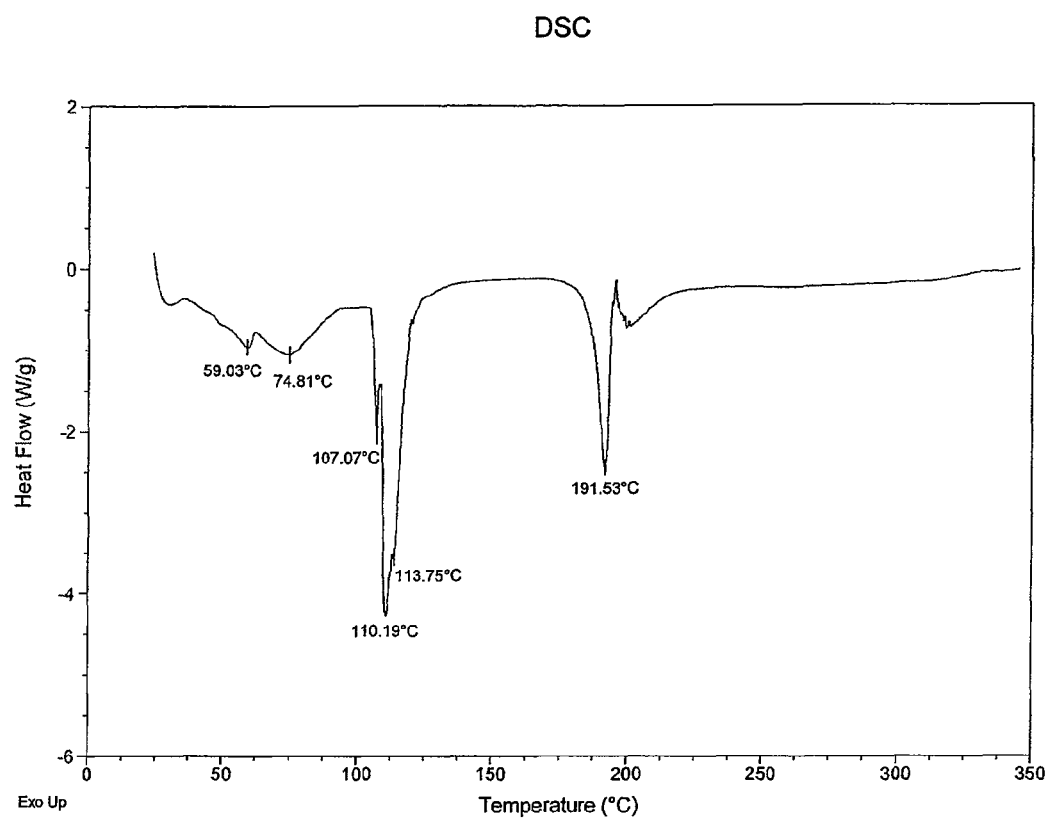
FIG. 22 is a characteristic DSC thermogram of Form E.

DSC analysis (FIG. 22) showed two small endotherms at 59° C. and 75° C. (dehydration), a forked endotherm with peaks at 107° C., 110° C., and 114° C., followed by a single endotherm at 192° C.

Hot stage analysis of Form E (micrographs not included) showed changes in birefringence at 59° C. and 81° C., which was consistent with dehydration of the solid. Hot stage microscopy further showed that the approximate end of melt occurred at about 185° C.

Figure 23:
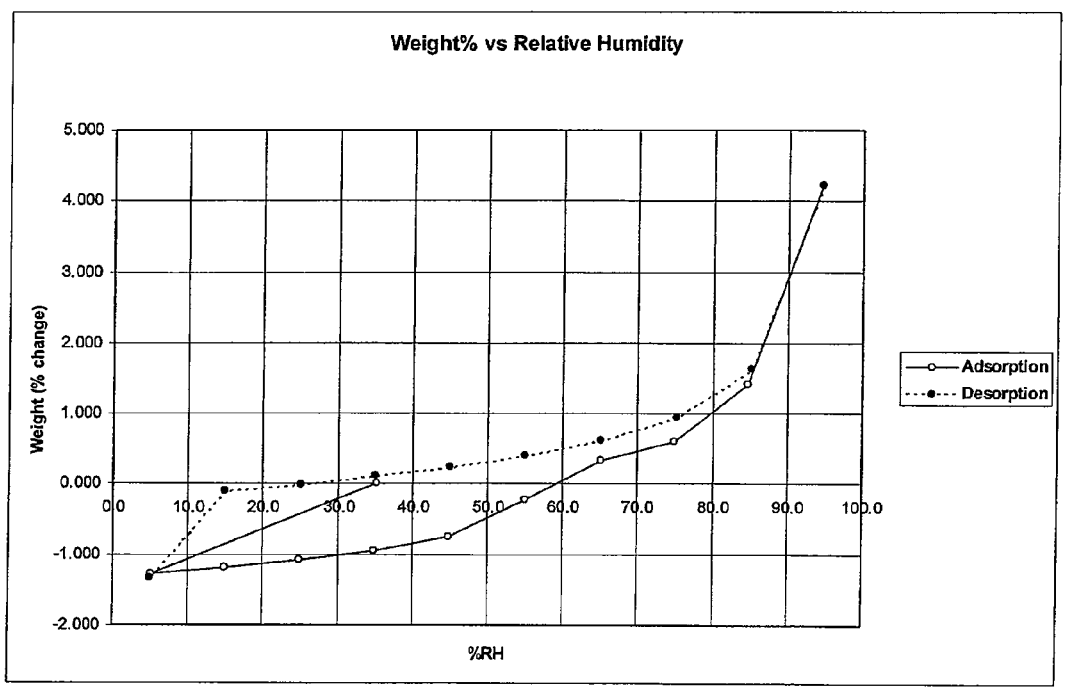
FIG. 23 is a moisture sorption and desorption isotherm of Form E.

Moisture sorption/desorption data (FIG. 23 and Example 24) showed that Form E under dehydrating conditions convert to Form A. A 1.3% weight loss was observed on equilibration to 5% relative humidity. The sample gained approximately 5% weight on sorption from a 5-95% relative humidity change. A loss of approximately 6% weight was observed on desorption to 5% relative humidity. XRPD analysis on the post moisture sorption/desorption sample showed a mixture of Form A and Form E.

In summary, the characterization data indicated that Form E was a crystalline, hydrated solid.

6. Form F

Form F was prepared as a mixture with Form A (Form A+F) by precipitation from a THF:water (9:1) solution of Compound I under slow cooling crystallization conditions (Example 8). Precipitates of Form A+F was characterized by XRPD.

Figure 24:
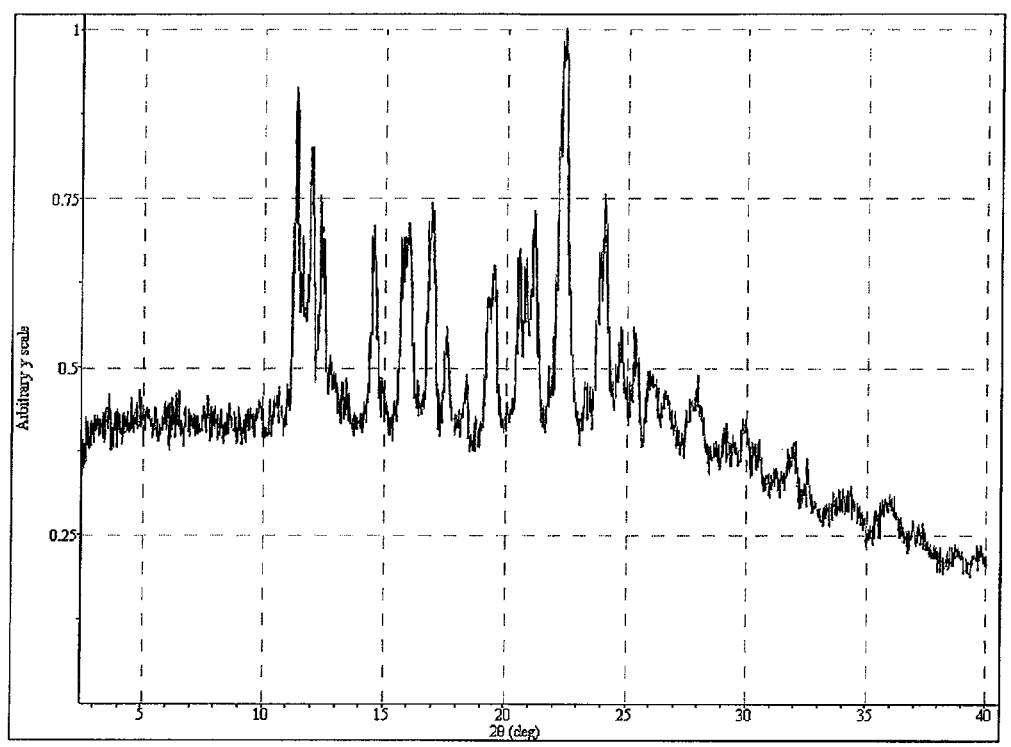
FIG. 24 is a characteristic XRPD spectrum of a mixture of Form A and Form F (Form A+F).

The characteristic XRPD spectrum (CuKα, λ=1.5418 Å) of Form A+F is shown in FIG. 24. The XRPD pattern confirmed that the material was crystalline. The major diffraction peaks expressed in °2θ and their relative intensities are summarized in Table 6.

TABLE 6

Characteristic XRPD Peaks (CuKα) of Form A + F

| Peak No. | 2θ (°) | d-spacing | Intensity | I/I₀ |
|---|---|---|---|---|
| 1 | 11.37 | 7.78 | 420 | 61 |
| 2 | 11.93 | 7.41 | 335 | 49 |
| 3 | 12.39 | 7.14 | 298 | 44 |
| 4 | 12.91 | 6.85 | 77 | 11 |
| 5 | 14.54 | 6.09 | 267 | 39 |
| 6 | 15.86 | 5.58 | 351 | 51 |
| 7 | 16.88 | 5.25 | 358 | 52 |
| 8 | 17.54 | 5.05 | 128 | 19 |
| 9 | 19.39 | 4.57 | 289 | 42 |
| 10 | 20.63 | 4.30 | 258 | 38 |
| 11 | 21.05 | 4.22 | 314 | 46 |
| 12 | 22.34 | 3.98 | 683 | 100 |
| 13 | 23.98 | 3.71 | 355 | 52 |
| 14 | 24.71 | 3.60 | 158 | 23 |
| 15 | 25.29 | 3.52 | 150 | 22 |
| 16 | 26.03 | 3.42 | 127 | 19 |
| 17 | 26.63 | 3.35 | 92 | 13 |
| 18 | 27.80 | 3.21 | 113 | 17 |
| 19 | 30.05 | 2.97 | 81 | 12 |
| 20 | 31.86 | 2.81 | 78 | 11 |

Figure 25:
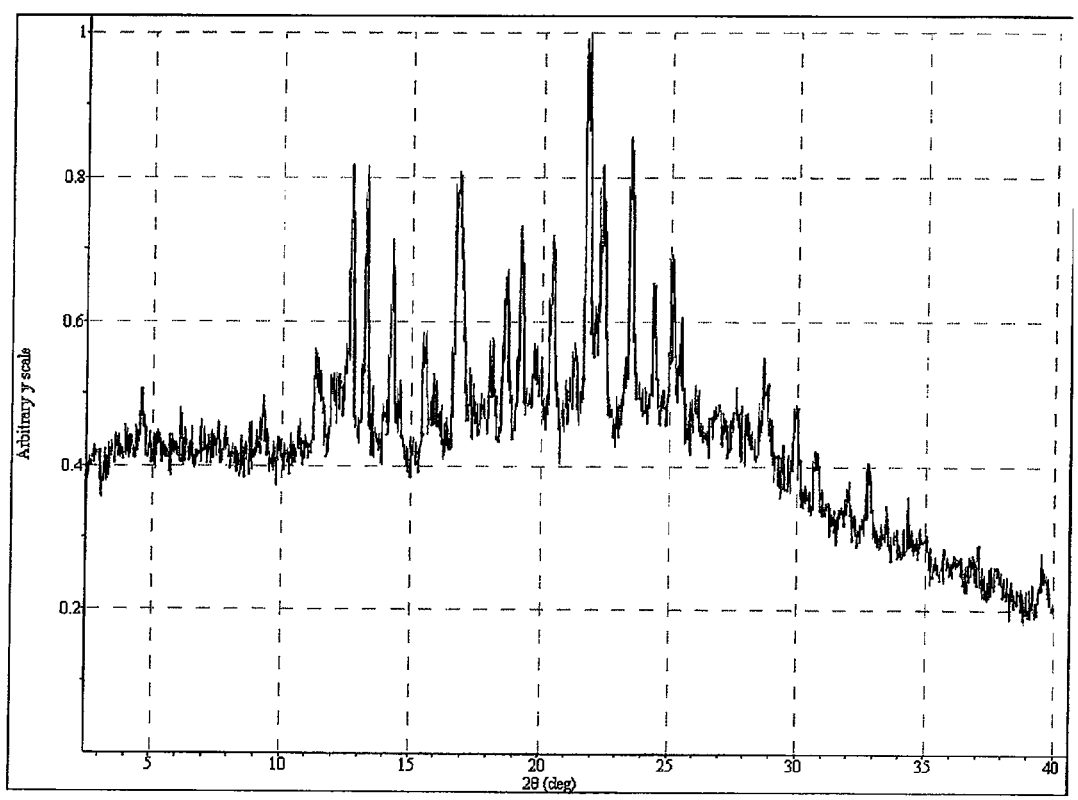
FIG. 25 is a characteristic XRPD spectrum of a mixture of Form A, Form E and Form G (Form A+E+G).

The unique set of XRPD peaks above or a subset of peaks thereof can be used to identify Form A+F of Compound I. A subset of peaks which are characteristic of Form F alone was which may be used to identify Form F was obtained by subtracting the XRPD peaks of Form A from those of Form A+F; this subset comprises peaks at about 12.39, 20.63, 26.03, and 30.05° 2θ and may be used to identify the presence of Form E 7. Form G Form G was prepared as a mixture with Form A and Form E (Form A+E+G) by precipitation from a THF:water (9:1)

solution of Compound I by slurrying at ambient conditions (Example 9). The precipitant was characterized by XRPD and was confirmed to be crystalline. The characteristic XRPD spectrum (CuKα) of Form A+E+G is shown in FIG. 25. The major diffraction peaks expressed in °2θ and their relative intensities are summarized in Table 7.

TABLE 7

Characteristic XRPD Peaks (CuKα) of Form A + E + G

| Peak No. | 2θ (°) | d-spacing | Intensity | I/I$_o$ |
|---|---|---|---|---|
| 1 | 4.60 | 19.21 | 88 | 16 |
| 2 | 9.27 | 9.53 | 57 | 10 |
| 3 | 11.37 | 7.78 | 144 | 26 |
| 4 | 12.01 | 7.37 | 96 | 17 |
| 5 | 12.21 | 7.24 | 93 | 17 |
| 6 | 12.64 | 7.00 | 334 | 60 |
| 7 | 13.22 | 6.69 | 293 | 52 |
| 8 | 13.91 | 6.36 | 50 | 9 |
| 9 | 14.23 | 6.22 | 228 | 41 |
| 10 | 14.59 | 6.07 | 69 | 12 |
| 11 | 15.50 | 5.71 | 142 | 25 |
| 12 | 15.87 | 5.58 | 86 | 15 |
| 13 | 16.81 | 5.27 | 426 | 76 |
| 14 | 17.33 | 5.11 | 79 | 14 |
| 15 | 17.71 | 5.00 | 62 | 11 |
| 16 | 18.08 | 4.90 | 137 | 24 |
| 17 | 18.62 | 4.76 | 230 | 41 |
| 18 | 19.20 | 4.62 | 259 | 46 |
| 19 | 19.77 | 4.49 | 128 | 23 |
| 20 | 20.42 | 4.35 | 273 | 49 |
| 21 | 20.99 | 4.23 | 81 | 14 |
| 22 | 21.28 | 4.17 | 139 | 25 |
| 23 | 21.76 | 4.08 | 560 | 100 |
| 24 | 22.33 | 3.98 | 376 | 67 |
| 25 | 23.44 | 3.79 | 419 | 75 |
| 26 | 23.79 | 3.74 | 95 | 17 |
| 27 | 24.36 | 3.65 | 223 | 40 |
| 28 | 24.69 | 3.60 | 93 | 17 |
| 29 | 25.06 | 3.55 | 281 | 50 |
| 30 | 25.39 | 3.51 | 182 | 33 |
| 31 | 25.77 | 3.45 | 70 | 13 |
| 32 | 25.95 | 3.43 | 107 | 19 |
| 33 | 26.33 | 3.38 | 64 | 11 |
| 34 | 26.83 | 3.32 | 107 | 19 |
| 35 | 27.15 | 3.28 | 78 | 14 |
| 36 | 27.54 | 3.24 | 124 | 22 |
| 37 | 28.07 | 3.18 | 93 | 17 |
| 38 | 28.69 | 3.11 | 176 | 31 |
| 39 | 29.13 | 3.06 | 53 | 9 |
| 40 | 29.87 | 2.99 | 130 | 23 |
| 41 | 30.71 | 2.91 | 98 | 18 |
| 42 | 32.75 | 2.73 | 110 | 20 |

The unique set of XRPD peaks above or a subset thereof can be used to identify Form A+E+G of Compound I. A subset of peaks that is characteristic of Form G was obtained by subtracting the XRPD peaks of Form A and Form E from the XRPD spectrum of Form A+E+G; this subset comprised peaks positioned at about 13.22, 14.23, 18.62, 19.77, 24.36, 25.06, and 30.71° 2θ. This subset of characteristic peaks of Form G may be used for identifying the presence of Form G.

8. Amorphous Form

Figure 26:
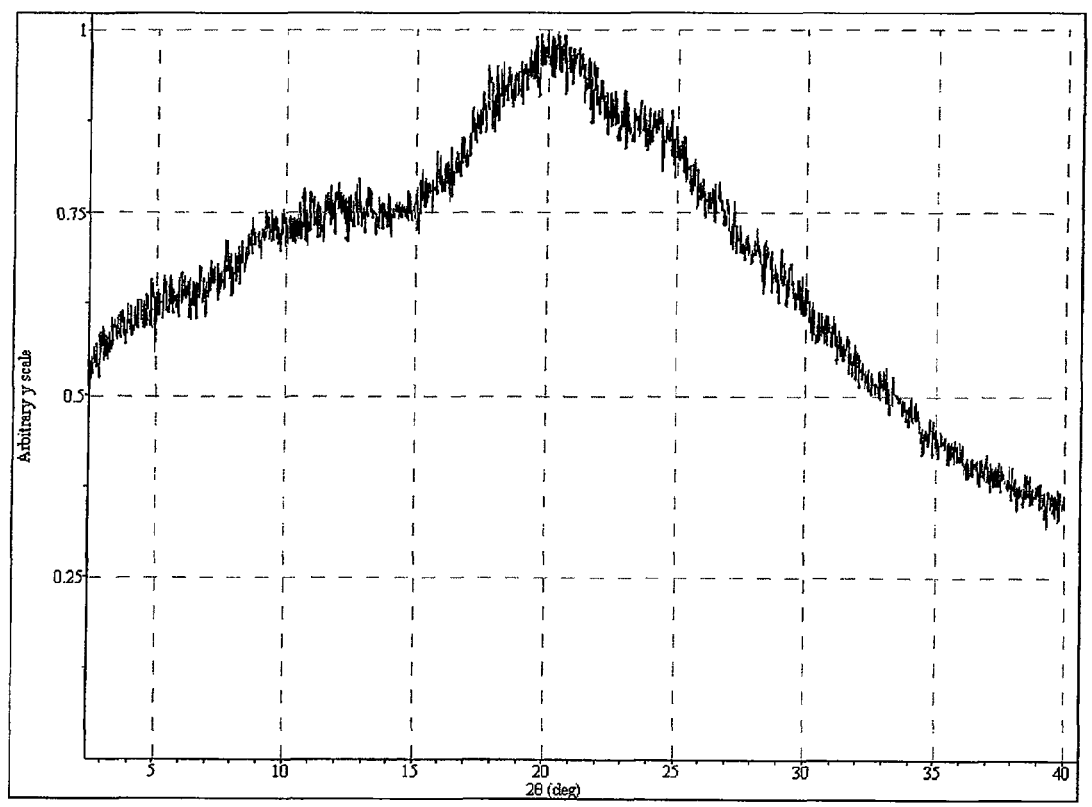
FIG. 26 is a characteristic XRPD spectrum of Amorphous Form.

The Amorphous Form of Compound I was prepared by lyophilization of an aqueous solution of Compound I (Example 10). The residue material was characterized by XRPD and the resulting XRPD spectrum displayed in FIG. 26. The XRPD spectrum shows a broad halo with no specific peaks present, which confirms that the material is amorphous. The material was further characterized by TGA, DSC, hot stage microscopy, and moisture sorption analysis.

Figure 27:
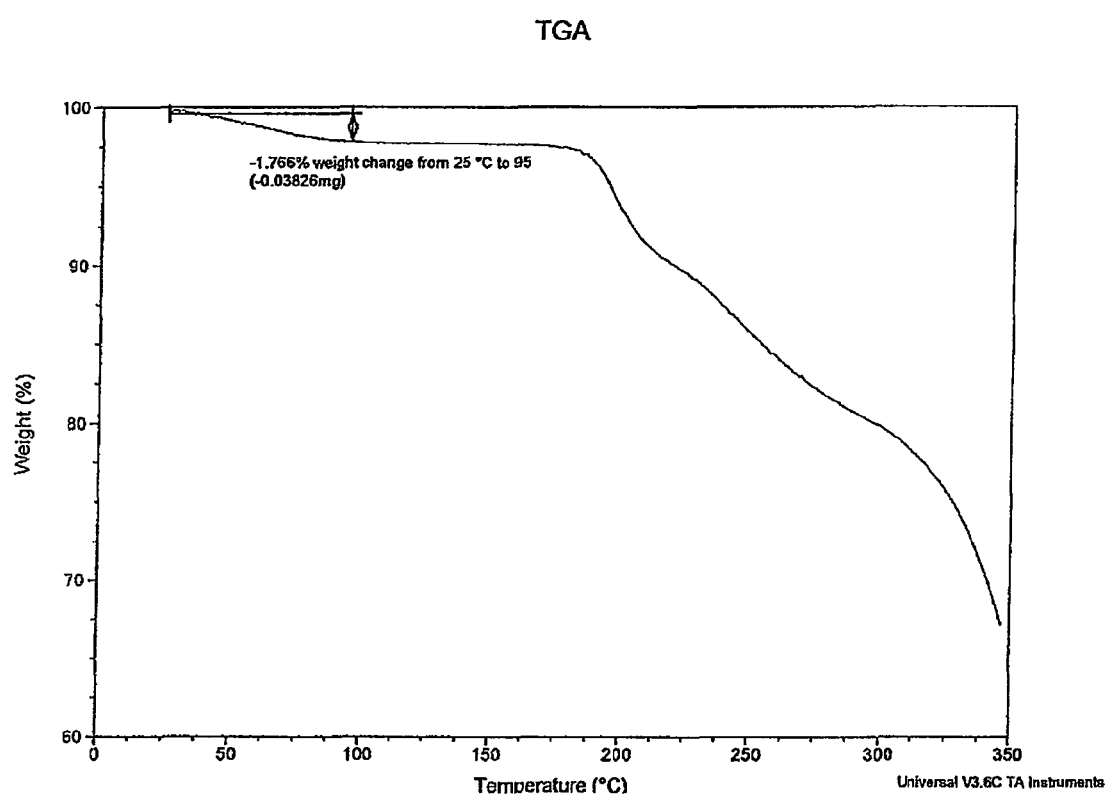
FIG. 27 is a characteristic TGA thermogram of Amorphous Form.

TGA analysis (FIG. 27) showed a 1.8% weight loss from 25° C. to 95° C., which was likely due to loss of residual solvent.

Figure 28:
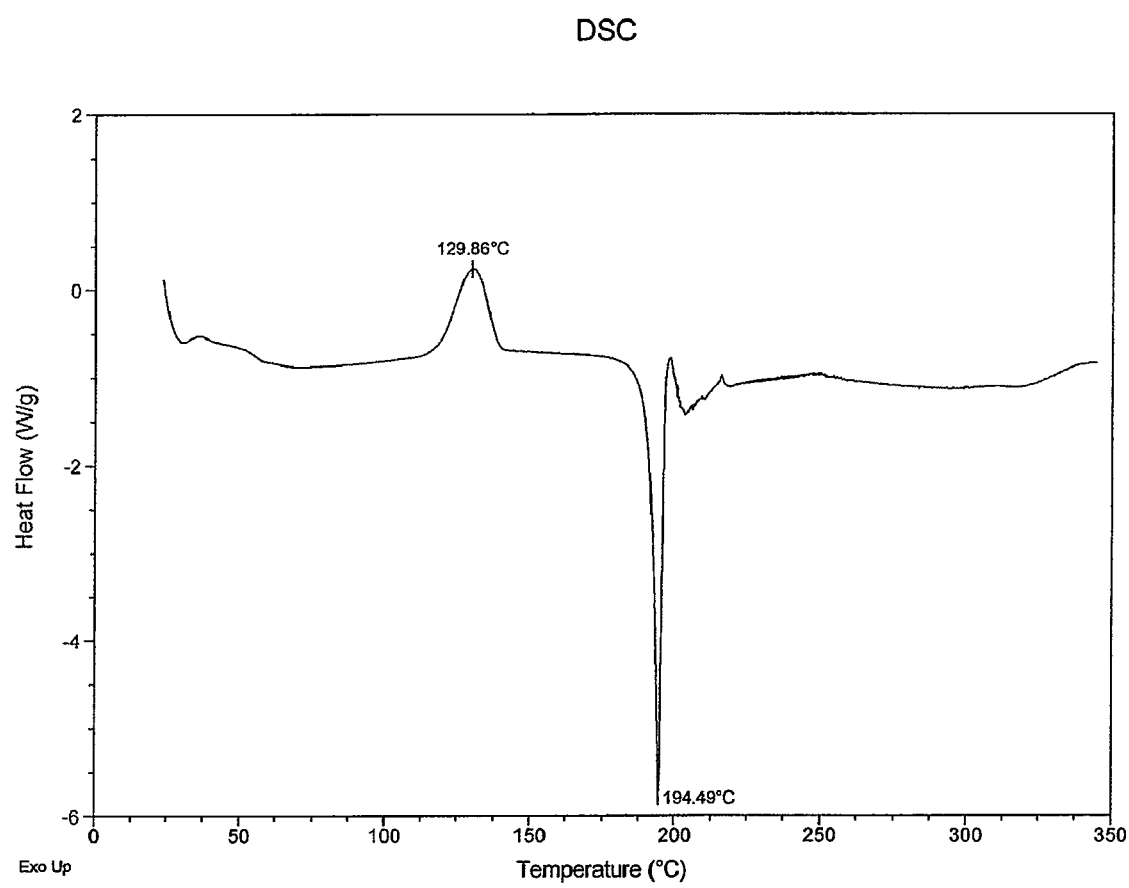
FIG. 28 is a characteristic DSC thermogram of Amorphous Form.
Figure 29:
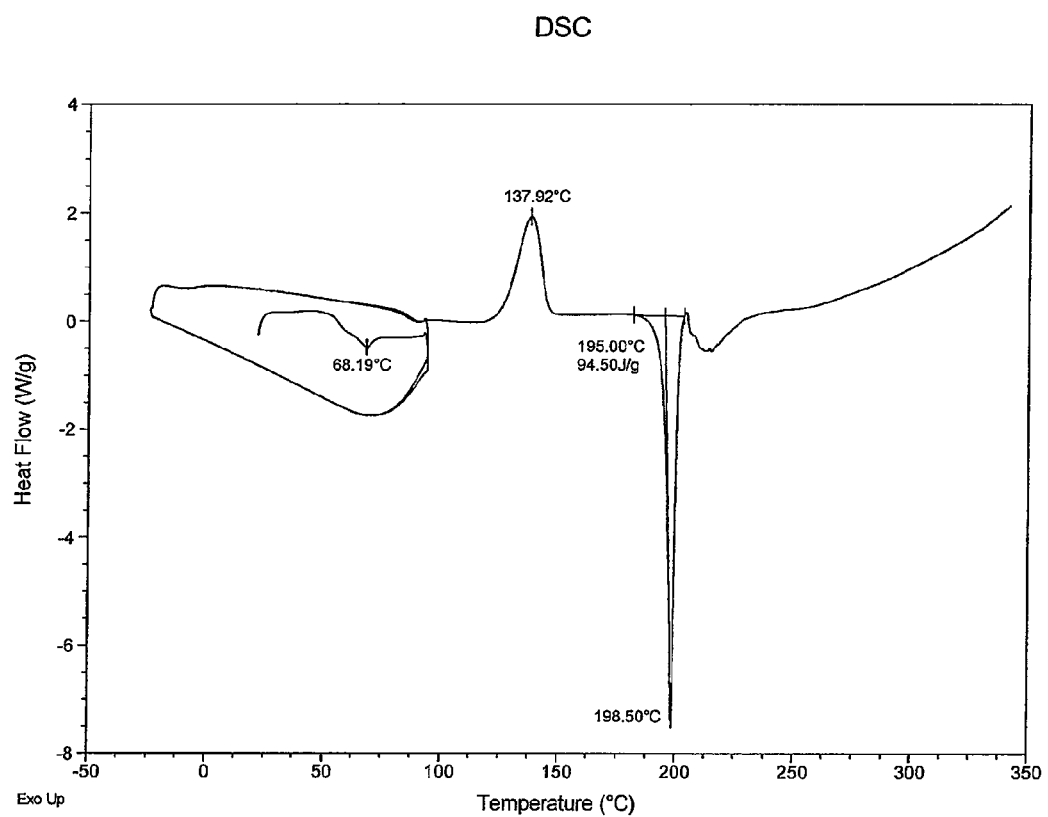
FIG. 29 is a DSC thermogram for assessing the glass transitional temperature of Amorphous Form.

DSC analysis (FIG. 28) showed a slightly concave baseline up to an exotherm at 130° C. (recrystallization), followed by an endotherm at 194° C., which results from the melting of Form A. Hot stage microscopy confirmed these recrystallization and melting events (micrographs not included). An approximate glass transition was observed (FIG. 29) at an onset temperature of 82° C.

Figure 30:
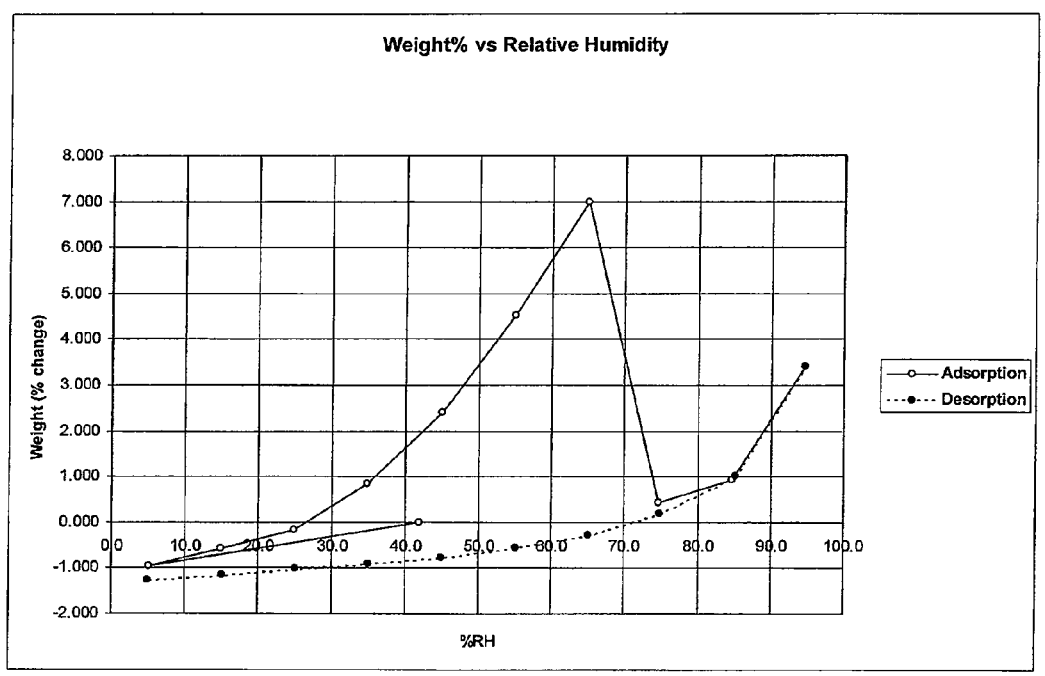
FIG. 30 is a moisture sorption and desorption isotherm of Amorphous Form.
Figure 31:
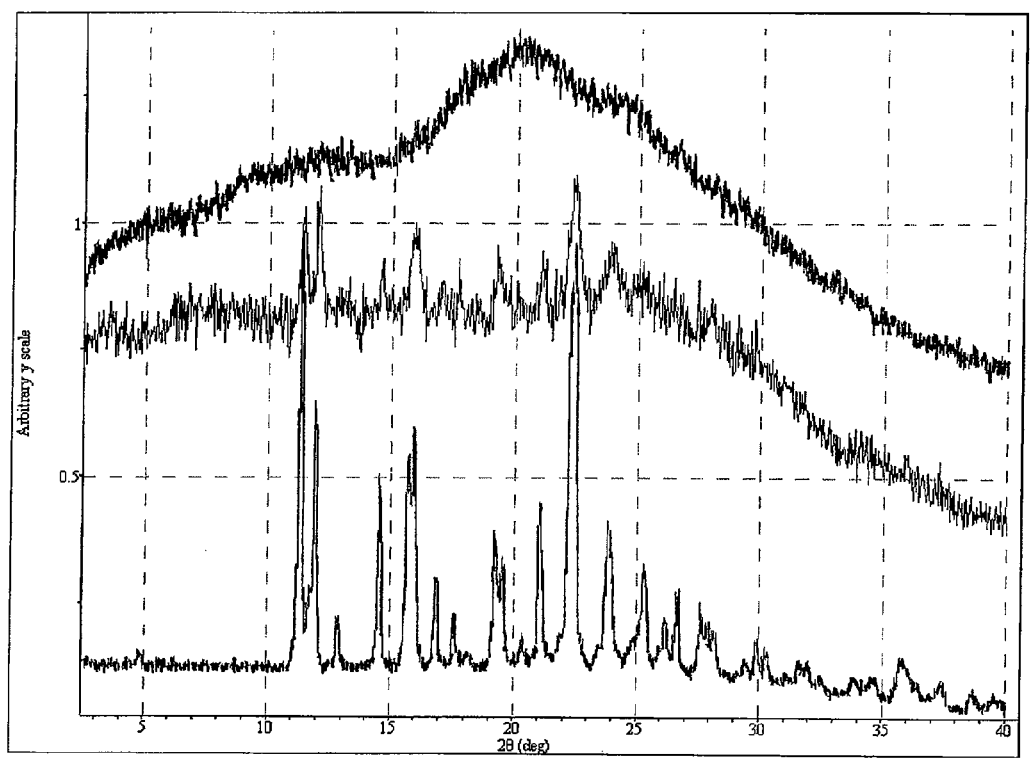
FIG. 31 shows XRPD spectra of Amorphous Form before (top) and after (middle) a moisture sorption/desorption analysis, and an XRPD pattern of Form A (bottom).

Moisture sorption/desorption data (FIG. 30 and Example 25) showed a 1.0% weight loss on equilibration at 5% relative humidity. Approximately 8% of weight was gained up to 65% relative humidity. Approximately 7% of weight was lost at 75% relative humidity. This is likely due to the recrystallization of the amorphous material to a crystalline solid. A 4.4% weight gain was observed on sorption from 75% to 95% relative humidity. Approximately 4.7% weight was lost on desorption from 95% to 5% relative humidity. The solid material remaining after the moisture sorption analysis was determined to be Form A by XRPD (FIG. 31).

Figure 19:
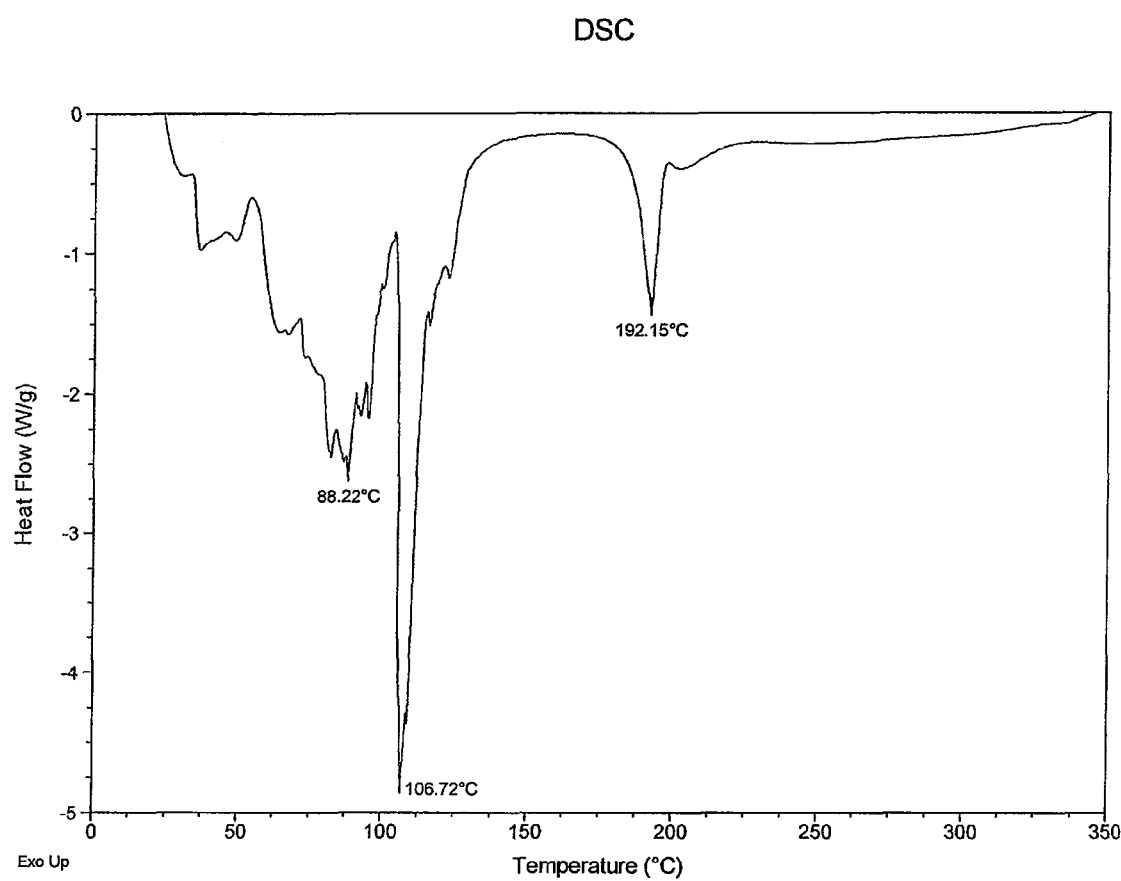
FIG. 19 is a characteristic DSC thermogram of Form D.

Stressing Amorphous Form in acetone or ethanol vapors resulted in Form A (Example 22). Stressing Amorphous Form at 58% and 88% relative humidity resulted in Form A (FIG. 19). Stressing Amorphous Form in water vapor resulted in a mixture of Forms A and D (Example 22).

Indications for Use of Compound I

The present invention also relates to methods to alter, preferably to reduce DPP-IV activity within a subject by administrating Compound I in a form selected from the group consisting of Form A, Form B, Form C, Form D, Form E, Form F, Form G, Amorphous Form, and combinations thereof.

DPP-IV is believed to contribute to the pathology and/or symptomology of several different diseases such that reduction of the activity of DPP-IV in a subject through inhibition may be used to therapeutically address these disease states. Examples of various diseases that may be treated using Compound I of the present invention are described herein. It is noted that additional diseases beyond those disclosed herein may be later identified as the biological roles that DPP-IV plays in various pathways becomes more fully understood.

Compound I may be used to treat or prevent diabetes and obesity related conditions. DPP-IV has been shown to be the primary degrading enzyme of GLP-1 (7-36), in vivo. GLP-1 (7-36) has multiple actions in vivo including the stimulation of insulin secretion, inhibition of glucagon secretion, the promotion of satiety, and the slowing of gastric emptying. The actions of GLP-1 (7-36) are believed to be beneficial in the prevention and treatment of type II diabetes and potentially obesity. DPP-IV degrades GLP-1 (7-36) efficiently to GLP-1 (9-36), which has been speculated to act as a physiological antagonist to GLP-1 (7-36). Inhibiting DPP-IV in vivo is therefore believed to be useful for potentiating endogenous levels of GLP-1 (7-36) and attenuating the formation of its antagonist GLP-1 (9-36). Thus, Compound I are believed to be useful in preventing, delaying the progression, and/or treating diabetes and more particularly, type 2 diabetes mellitus, diabetic dislipidemia, conditions of impaired glucose tolerance (IGT), conditions of impaired fasting plasma glucose (IFG), metabolic acidosis, ketosis, appetite regulation and obesity.

Compound I may be used as immuno-suppressants (or cytokine release suppressant drugs). DPP-IV expression is increased in T-cells upon mitogenic or antigenic stimulation (Mattem, T., et al., *Scand. J. Immunol.*, 1991, 33, 737). It has been reported that inhibitors of DPP-IV and antibodies to DPP-IV suppress the proliferation of mitogen-stimulated and antigen-stimulated T-cells in a dose-dependant manner (Schon, E., et al., *Biol. Chem.*, 1991, 372, 305). Various other functions of T-lymphocytes such as cytokine production, IL-2 mediated cell proliferation and B-cell helper activity have been shown to be dependent on DPP-IV activity (Schon, E., et al., *Scand. J. Immunol.*, 1989, 29, 127). DPP-IV inhibitors, based on boroProline, (Flentke, G. R., et al., *Proc. Nat. Acad. Sci. USA*, 1991, 88, 1556) although unstable, were effective at inhibiting antigen-induced lymphocyte proliferation and IL-2 production in murine $CD4^+$ T-helper cells. Such boronic acid inhibitors have been shown to have an effect in vivo in mice causing suppression of antibody production induced by immune challenge (Kubota, T. et al., *Clin. Exp. Immun.*, 1992, 89, 192). The role of DPP-IV in regulating T lymphocyte activation may also be attributed, in part, to its cell-surface association with the transmembrane phosphatase, CD45. DPP-IV inhibitors or non-active site ligands may possibly disrupt the CD45-DPP-IV association. CD45 is known to be an integral component of the T-cell signaling apparatus. It has been reported that DPP-IV is essential for the penetration and infectivity of HIV-1 and HIV-2 viruses in $CD4^+$ T-cells (Wakselman, M., Nguyen, C., Mazaleyrat, J.-P., Callebaut, C., Krust, B., Hovanessian, A. G., Inhibition of HIV-1 infection of $CD26^+$ but not $CD26^{th}$ cells by a potent cyclopeptidic inhibitor of the DPP-IV activity of CD26, Abstract P.44 of the $24^{th}$ European Peptide Symposium 1996). Additionally, DPP-IV has been shown to associate with the enzyme adenosine deaminase (ADA) on the surface of T-cells (Kameoka, J., et al., *Science*, 193, 26 466). ADA deficiency causes severe combined immunodeficiency disease (SCID) in humans. This ADA-CD26 interaction may provide clues to the pathophysiology of SCID. It follows that inhibitors of DPP-IV may be useful immunosuppressants (or cytokine release suppressant drugs) for the treatment of, among other things, organ transplant rejection; autoimmune diseases such as inflammatory bowel disease, multiple sclerosis and rheumatoid arthritis; and the treatment of AIDS.

Compound I may be used for treating various cancers. It has been shown that lung endothelial cell DPP-IV is an adhesion molecule for lung-metastatic rat breast and prostate carcinoma cells (Johnson, R. C., et al., *J. Cell. Biol.*, 1993, 121, 1423). DPP-IV is known to bind to fibronectin and some metastatic tumor cells are known to carry large amounts of fibronectin on their surface. Potent DPP-IV inhibitors may be useful as drugs to prevent metastases of, for example, breast and prostrate tumors to the lungs.

Compound I may be useful as agents to treat dermatological diseases such as psoriasis and lichen planus. High levels of DPP-IV expression have also been found in human skin fibroblast cells from patients with psoriasis, rheumatoid arthritis (RA) and lichen planus (Raynaud, F., et al., *J. Cell. Physiol.*, 1992, 151, 378). Therefore, DPP-IV inhibitors may be useful as agents to treat these conditions.

Compound I may be useful as a male contraceptive agent, and for treating female infertility and amenorrhea. High DPP-IV activity has been found in tissue homogenates from patients with benign prostate hypertrophy and in prostatosomes. These are prostate derived organelles important for the enhancement of sperm forward motility (Vanhoof, G., et al., *Eur. J. Clin. Chem. Clin. Biochem.*, 1992, 30, 333). DPP-IV inhibitors may also act to suppress sperm motility and therefore act as a male contraceptive agent. Conversely, DPP-IV inhibitors have been implicated as novel for treatment of infertility, and particularly human female infertility due to polycystic ovary syndrome (PCOS, Stein-Leventhal syndrome) which is a condition characterized by thickening of the ovarian capsule and formation of multiple follicular cysts. It results in infertility and amenorrhea.

Compound I may be used to modulate cleavage of various cytokines (stimulating hematopoietic cells), growth factors and neuropeptides. It was discovered that inhibitors of DPP-IV are useful for stimulating the growth and differentiation of hematopoietic cells in the absence of exogenously added cytokines or other growth factors or stromal cells. Stimulated hematopoietic cells are useful for the treatment of disorders that are characterized by a reduced number of hematopoietic cells or their precursors in vivo. Such conditions occur frequently in patients who are immunosuppressed, for example, as a consequence of chemotherapy and/or radiation therapy for cancer.

Compound I may be useful in the treatment of short stature due to growth hormone deficiency (Dwarfism). DPP-IV in human plasma has been shown to cleave N-terminal Tyr-Ala from growth hormone-releasing factor and cause inactivation of the hormone. Accordingly, inhibiting DPP-IV will modulate its effect and may promote GH-dependent tissue growth or re-growth.

Compound I may be useful for the regulation or normalization of neurological disorders. DPP-IV can cleave neuropeptides and has been shown to modulate the activity of neuroactive peptides substance P, neuropeptide Y and CLIP (Mentlein, R., Dahms, P., Grandt, D., Kruger, R., Proteolytic processing of neuropeptide Y and peptide YY by DPP-IV, *Regul. Pept.*, 49, 133, 1993; Wetzel, W., Wagner, T., Vogel, D., Demuth, H.-U., Balschun, D., Effects of the CLIP fragment ACTH 20-24 on the duration of REM sleep episodes, *Neuropeptides*, 31, 41, 1997). Thus, inhibiting DPP-IV would lessen its damaging effect on the neuropeptides.

Compositions, according to the present invention, may be administered, or coadministered with other active agents. These additional active agents may include, for example, one or more other pharmaceutically active agents. Coadministration in the context of this invention is intended to mean the administration of more than one therapeutic agent, one of which includes Compound I. Such co-administration may also be coextensive, that is, occurring during overlapping periods of time or may be sequential, that is, occurring during non-overlapping periods of time. Examples of co-administration of Compound I with other active ingredients in a combination therapy are described in U.S. patent application Ser. No. 11/531,671, filed Sep. 13, 2006, the disclosure of which is expressly incorporated herein by reference in its entirety.

For oncology indications, Compound I may be administered in conjunction with other agents to inhibit undesirable and uncontrolled cell proliferation. Examples of other anticell proliferation agents that may be used in conjunction with Compound I include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA)), cishydroxyproline, d,l-3,4-dehydroproline, thiaproline, beta.-aminopropionitrile fumarate, 4-propyl-5-(4-pyridinyl)-2(3H)-oxazolone, methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta.-1-anticollagenase-serum, alpha.2-antiplasmin, bisantrene, lobenzarit disodium, n-2-carboxyphenyl-4-chloroanthronilic acid disodium or "CCA", thalidomide; angostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

In another embodiment, a therapeutic method is provided that comprises administering Compound I. In another embodiment, a method of inhibiting cell proliferation is provided that comprises contacting a cell with an effective amount of Compound I. In another embodiment, a method of inhibiting cell proliferation in a patient is provided that comprises administering to the patient a therapeutically effective amount of Compound I.

In another embodiment, a method of treating diabetes and related conditions, including, but are not limited to, diabetic dislipidemia, conditions of impaired glucose tolerance (IGT), conditions of impaired fasting plasma glucose (IFG), metabolic acidosis, ketosis, appetite regulation, obesity, in a patient is provided that comprises administering to the patient a therapeutically effective amount of Compound I.

In another embodiment, a method of treating a condition in a patient which is known to be mediated by DPP-IV, or which is known to be treated by DPP-IV inhibitors, comprising administering to the patient a therapeutically effective amount of Compound I. In another embodiment, a method is provided for using Compound I in order to manufacture a medicament for use in the treatment of disease state which is known to be mediated by DPP-IV, or which is known to be treated by DPP-IV inhibitors.

In another embodiment, a method is provided for treating a disease state for which DPP-IV possesses activity that contributes to the pathology and/or symptomology of the disease state, the method comprising: administering Compound I to a subject such that the free base form of Compound I is present in the subject in a therapeutically effective amount for the disease state.

The present invention relates generally to a method comprising administering between 1 mg/day and 250 mg/day of Compound I to a patient, optionally between 2.5 mg and 200 mg of Compound I, optionally between 2.5 mg and 150 mg of Compound I, and optionally between 5 mg and 100 mg of Compound I (in each instance based on the molecular weight of the free base form of Compound I). Specific dosage amounts that may be used include, but are not limited to 2.5 mg, 5 mg, 6.25 mg, 10 mg, 20 mg, 25 mg, 50 mg, 75 mg and 100 mg of Compound I per day. It is noted that the dosage may be administered as a daily dose or weekly dose, once daily or multiple doses per day. It is noted that Compound I may be administered in a form selected from the group consisting of Form A, Form B, Form C, Form D, Form E, Form F, Form G, and Amorphous Form. However, the dosage amounts and ranges provided herein are always based on the molecular weight of the free base form of Compound I.

Compound I may be administered by any route of administration. In particular embodiments, however, the method of the present invention is practiced by administering Compound I orally.

Pharmaceutical Compositions Comprising Compound I where at Least One of Form A, Form B, Form C, Form D, Form E, Form F, Form G, or Amorphous Form is Present Compound I may be used in various pharmaceutical compositions where at least a portion of Compound I is present in the composition in a form selected from the group consisting of Form A, Form B, Form C, Form D, Form E, Form F, Form G, and Amorphous Form. The pharmaceutical composition should contain a sufficient quantity of Compound I to reduce dipeptidyl peptidases activity in vivo sufficiently to provide the desired therapeutic effect. Such pharmaceutical compositions may comprise Compound I present in the composition in a range of between 0.005% and 100% (weight/weight), optionally 0.1-95%, and optionally 1-95%.

In particular embodiments, the pharmaceutical compositions comprise at least 0.1%, 0.25%, 0.5%, 1%, 5%, 10%, 25%, 50%, 75%, 80%, 85%, 90%, 95%, 97%, or 99% of Compound I in a form selected from a group consisting of Form A, Form B, Form C, Form D, Form E, Form F, Form G, Amorphous Form, and a mixture thereof. In another embodiment, a particular polymorphic form selected from the group consisting of Form A, Form B, Form C, Form D, Form E, Form F, Form G, Amorphous Form may comprise at least 0.1%, 1%, 5%, 10%, 25%, 50%, 75%, 80%, 85%, 90%, 95%, 97%, or 99% of the total amount of Compound I (weight/weight) in the pharmaceutical composition.

In addition to Compound I, the pharmaceutical composition may comprise one or more additional components that do not deleteriously affect the use of Compound I. For example, the pharmaceutical compositions may include, in addition to Compound I, conventional pharmaceutical carriers; excipients; diluents; lubricants; binders; wetting agents; disintegrating agents; glidants; sweetening agents; flavoring agents; emulsifying agents; solubilizing agents; pH buffering agents; perfuming agents; surface stabilizing agents; suspending agents; and other conventional, pharmaceutically inactive agents. In particular, the pharmaceutical compositions may comprise lactose, mannitol, glucose, sucrose, dicalcium phosphate, magnesium carbonate, sodium saccharin, carboxymethylcellulose, magnesium stearate, calcium stearate, sodium crosscarmellose, talc, starch, natural gums (e.g., gum acaciagelatin), molasses, polyvinylpyrrolidine, celluloses and derivatives thereof, povidone, crospovidones acetate, sodium citrate, cyclodextrine derivatives, sorbitan monolaurate, triethanolamine sodium acetate, triethanolamine oleate, biocompatible polymers, such as collagen, ethylene vinyl acetate, polyanhydrides, polyglycolic acid, polyorthoesters, polylactic acid and others such agents.

Pharmaceutical compositions according to the present invention may be adapted for administration by any of a variety of routes. For example, pharmaceutical compositions according to the present invention can be administered orally, parenterally, intraperitoneally, intravenously, intraarterially, topically, transdermally, sublingually, intramuscularly, rectally, transbuccally, intranasally, liposomally, via inhalation, vaginally, intraoccularly, via local delivery (for example, by catheter or stent), subcutaneously, intraadiposally, intraarticularly, or intrathecally, optionally in a slow release dosage form. In particular embodiments, the pharmaceutical compounds are administered orally, by inhalation or by injection subcutaneously, intramuscularly, intravenously or directly into the cerebrospinal fluid.

In general, the pharmaceutical compositions of the present invention may be prepared in a gaseous, liquid, semi-liquid, gel, or solid form, and formulated in a manner suitable for the route of administration to be used.

Compositions according to the present invention are optionally provided for administration to humans and animals in unit dosage forms or multiple dosage forms, such as tablets, capsules, pills, powders, dry powders for inhalers, granules, sterile parenteral solutions or suspensions, oral solutions or suspensions, oil-water emulsions, sustained release formulations, such as, but not limited to, implants and microencapsulated delivery systems, containing suitable quantities of Compound I. Methods of preparing such dosage forms are known in the art, and will be apparent to those skilled in this art; for example, see *Remington's Pharmaceutical Sciences*, 19th Ed. (Easton, Pa.: Mack Publishing Company, 1995).

Unit-dose forms, as used herein, refers to physically discrete units suitable for human and animal subjects and packaged individually as is known in the art. Each unit-dose contains a predetermined quantity of Compound I sufficient to produce the desired therapeutic effect, in association with a pharmaceutical carrier, vehicle or diluent. Examples of unit-dose forms include ampoules and syringes, and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules, or bottles of pints or gallons. Hence, multiple dose form may be viewed as a multiple of unit-doses that are not segregated in packaging.

In general, the total amount of Compound I in a pharmaceutical composition according to the present invention should be sufficient to a desired therapeutic effect. This amount may be delivered as a single per day dosage, multiple dosages per day to be administered at intervals of time, or as a continuous release dosage form. It is noted that Compound I may be administered in a form selected from the group consisting of Form A, Form B, Form C, Form D, Form E, Form F, Form G, Amorphous Form, and a mixture thereof. Compound I may advantageously be used when administered to a patient at a daily dose of between 1 mg/day and 250 mg/day of Compound I, optionally between 2.5 mg and 200 mg of Compound I, optionally between 2.5 mg and 150 mg of Compound I, and optionally between 5 mg and 100 mg of Compound I (in each instance based on the molecular weight of the free base form of Compound I). Specific dosage amounts that may be used include, but are not limited to 2.5 mg, 5 mg, 6.25 mg, 10 mg, 20 mg, 25 mg, 50 mg, 75 mg, and 100 mg of Compound I per day. It may be desirable for Compound I to be administered one time per day. Accordingly, pharmaceutical compositions of the present invention may be in the form of a single dose form comprising between 1 mg/day and 250 mg/day of Compound I, optionally between 2.5 mg and 200 mg of Compound I, optionally between 2.5 mg and 150 mg of Compound I, and optionally between 5 mg and 100 mg of Compound I. In specific embodiments, the pharmaceutical composition comprises 2.5 mg, 5 mg, 6.25 mg, 10 mg, 20 mg, 25 mg, 50 mg, 75 mg or 100 mg of Compound I.

A. Formulations for Oral Administration

Oral pharmaceutical dosage forms may be as a solid, gel or liquid where at least a portion of Compound I is present in the composition in a form selected from the group consisting of one or more of Form A, Form B, Form C, Form D, Form E, Form F, Form G, and Amorphous Form.

In certain embodiments, Compound I is provided as solid dosage forms. Examples of solid dosage forms include, but are not limited to pills, tablets, troches, capsules, granules, and bulk powders. More specific examples of oral tablets include compressed, chewable lozenges, troches and tablets that may be enteric-coated, sugar-coated or film-coated. Examples of capsules include hard or soft gelatin capsules. Granules and powders may be provided in non-effervescent or effervescent forms. The powders may be prepared by lyophilization or by other suitable methods.

The tablets, pills, capsules, troches and the like may optionally contain one or more of the following ingredients, or compounds of a similar nature: a binder; a diluent; a disintegrating agent; a lubricant; a glidant; a coloring agent; a sweetening agent; a flavoring agent; and a wetting agent.

Examples of binders that may be used include, but are not limited to, microcrystalline cellulose, gum tragacanth, glucose solution, acacia mucilage, gelatin solution, sucrose, and starch paste.

Examples of diluents that may be used include, but are not limited to, lactose, sucrose, starch, kaolin, salt, mannitol, and dicalcium phosphate.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of lubricants that may be used include, but are not limited to, talc, starch, magnesium or calcium stearate, lycopodium and stearic acid.

Examples of glidants that may be used include, but are not limited to, colloidal silicon dioxide.

Examples of coloring agents that may be used include, but are not limited to, any of the approved certified water soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

When the dosage form is a pill, tablet, torches, or the like, Compound I may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compound I may also be administered as a component of an elixir, emulsion, suspension, microsuspension, syrup, wafer, sprinkle, chewing gum or the like. A syrup may optionally comprise, in addition to the active compounds, sucrose as a sweetening agent and certain preservatives, dyes, colorings, and flavors.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

Examples of oral formulations that may be used to administer Compound I has been described in U.S. patent application Ser. No. 11/531,671, filed Sep. 13, 2006, the disclosure of which is herein expressly incorporated by reference in its entirety.

Exemplary tablet formulations are provided below. It is noted that the examples are, by way of illustration but not limitation. It is also noted that Compound I is present in the formulation in a form selected from the group consisting of one or more of Form A, Form B, Form C, Form D, Form E, Form F, Form G, and Amorphous Form. It is also noted that the formulations provided herein may be varied as is known in the art.

| 12.5 mg of Compound I (weight of free base form) per tablet Core Tablet Formulation | |
|---|---|
| (1) Compound I | 17.0 mg |
| (2) Lactose Monohydrate, NF, Ph, Eur (FOREMOST 316 FAST FLO) | 224.6 mg |
| (3) Microcrystalline Cellulose, NF, Ph, Eur (AVICEL PH 102) | 120.1 mg |
| (4) Croscarmellose Sodium, NF, Ph, Eur (AC-DO-SOL) | 32.0 mg |
| (5) Colloidal Silicon Dioxide, NF, Ph, Eur (CAB-O-SIL M-5P) | 3.2 mg |
| (6) Magnesium Stearate, NF, Ph, Eur (MALLINCKRODT, Non-bovine Hyqual) | 3.2 mg |
| TOTAL (per tablet) | 400.0 mg |

Film Coat (12.0 mg in total)
(1) Opadry II 85F18422, White - Portion 1 (COLORCON)
(2) Opadry II 85F18422, White - Portion 2 (COLORCON)
(3) Opadry II 85F18422, White - Portion 3 (COLORCON)

| 25 mg of Compound I (weight of free base form) per tablet Core Tablet Formulation | |
|---|---|
| (1) Compound I | 34.0 mg |
| (2) Lactose Monohydrate, NF, Ph, Eur (FOREMOST 316 FAST FLO) | 207.6 mg |
| (3) Microcrystalline Cellulose, NF, Ph, Eur (AVICEL PH 102) | 120.1 mg |
| (4) Croscarmellose Sodium, NF, Ph, Eur (AC-DO-SOL) | 32.0 mg |
| (5) Colloidal Silicon Dioxide, NF, Ph, Eur (CAB-O-SIL M-5P) | 3.2 mg |
| (6) Magnesium Stearate, NF, Ph, Eur (MALLINCKRODT, Non-bovine Hyqual) | 3.2 mg |
| TOTAL (per tablet) | 400.0 mg |

Film Coat (12.0 mg in total)
(1) Opadry II 85F18422, White - Portion 1 (COLORCON)
(2) Opadry II 85F18422, White - Portion 2 (COLORCON)
(3) Opadry II 85F18422, White - Portion 3 (COLORCON)

| 50 mg of Compound I (weight of free base form) per tablet Core Tablet Formulation | |
|---|---|
| (1) Compound I | 68.0 mg |
| (2) Lactose Monohydrate, NF, Ph, Eur (FOREMOST 316 FAST FLO) | 173.6 mg |
| (3) Microcrystalline Cellulose, NF, Ph, Eur (AVICEL PH 102) | 120.1 mg |
| (4) Croscarmellose Sodium, NF, Ph, Eur (AC-DO-SOL) | 32.0 mg |
| (5) Colloidal Silicon Dioxide, NF, Ph, Eur (CAB-O-SIL M-5P) | 3.2 mg |
| (6) Magnesium Stearate, NF, Ph, Eur (MALLINCKRODT, Non-bovine Hyqual) | 3.2 mg |
| TOTAL (per tablet) | 400.0 mg |

Film Coat (12.0 mg in total)
(1) Opadry II 85F18422, White - Portion 1 (COLORCON)
(2) Opadry II 85F18422, White - Portion 2 (COLORCON)
(3) Opadry II 85F18422, White - Portion 3 (COLORCON)

B. Injectables, Solutions and Emulsions

Compound I present in a form or a mixture of forms selected from the group consisting of Form A, Form B, Form C, Form D, Form E, Form F, Form G, and Amorphous Form may be formulated for parenteral administration. Parenteral administration generally characterized by injection, either subcutaneously, intramuscularly or intravenously. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the route of administration and the indication of disease to be treated.

Injectables may be prepared in any conventional form. These formulations include, but are not limited to, sterile solutions, suspensions, microsuspensions, and emulsions ready for injection, and solid forms, e.g., lyophilized or other powders including hypodermic tablets, ready to be combined with a carrier just prior to use. Generally, the resulting formulation may be a solution, microsuspension, suspension and emulsion. The carrier may be an aqueous, non-aqueous liquid, or a solid vehicle that can be suspended in liquid.

Examples of carriers that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of Compound I in the parenteral formulation may be adjusted so that an injection administers a pharmaceutically effective amount sufficient to produce the desired pharmacological effect. The exact concentration of Compound I and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of Compound I to the treated tissue(s). Compound I may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

Compound I may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

C. Powders

Compound I in a form or a mixture of forms selected from the group consisting of Form A, Form B, Form C, Form D, Form E, Form F, Form G, and Amorphous Form may be prepared as powders, which can be reconstituted for administration as solutions, emulsions and other mixtures. The powders may also be formulated as solids or gels.

Powders of Compound I may be prepared by grinding, spray drying, lyophilzation and other techniques that are well known in the art. Sterile, lyophilized powder may be prepared by dissolving Compound I in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, Compound I is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of Compound I.

D. Topical Administration

Compound I present in a form selected from the group consisting of Form A, Form B, Form C, Form D, Form E, Form F, Form G, and Amorphous Form may also be administered as topical mixtures. Topical mixtures may be used for local and systemic administration. The resulting mixture may be a solution, suspension, microsuspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

Compound I may be formulated for topical applications to the respiratory tract. These pulmonary formulations can be in the form of an aerosol, solution, emulsion, suspension, microsuspension for a nebulizer, or as a microfine powder for insufflation, alone or in combination with an inert carrier such as lactose. In such a case, the particles of the formulation will typically have diameters of less than 50 microns, preferably less than 10 microns. Examples of aerosols for topical application, such as by inhalation are disclosed in U.S. Pat. Nos. 4,044,126, 4,414,209, and 4,364,923, which describe aerosols for delivery of a steroid useful for treatment inflammatory diseases, particularly asthma.

Compound I may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions or suspensions of Compound I alone or in combination with other pharmaceutically acceptable excipients can also be administered.

E. Formulations for Other Routes of Administration

Depending upon the disease state being treated, Compound I present in one form or a mixture of forms selected from the group consisting of Form A, Form B, Form C, Form D, Form E, Form F, Form G, and Amorphous Form may be formulated for other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Kits and Articles of Manufacture Comprising Compound I Polymorphs

The present invention is also directed to kits and other articles of manufacture for treating diseases associated with dipeptidyl peptidases. It is noted that diseases are intended to cover all conditions for which the dipeptidyl peptidases possesses activity that contributes to the pathology and/or symptomology of the condition.

In one embodiment, a kit is provided that comprises a pharmaceutical composition comprising Compound I where greater than 0.1%, 1%, 5%, 10%, 25%, 50%, 75%, 80%, 85%, 90%, 95%, 97% or 99% of Compound I (by weight) is present in a form selected from the group consisting of Form A, Form B, Form C, Form D, Form E, Form F, Form G, and Amorphous Form; and instructions for use of the kit. Optionally, the composition comprises at least 0.1%, 0.25%, 0.5%, 1%, 5%, 10%, 25%, 50%, 75%, 80%, 85%, 90%, 95%, 97%, or 99% of Compound I. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a pharmaceutical composition comprising Compound I where greater than 0.1%, 1%, 5%, 10%, 25%, 50%, 75%, 80%, 85%, 90%, 95%, 97% or 99% of Compound I (by weight) is present in the composition in a form selected from the group consisting of Form A, Form B, Form C, Form D, Form E, Form F, Form G, and Amorphous Form; and packaging materials. Optionally, the composition comprises at least 0.1%, 0.25%, 0.5%, 1%, 5%, 10%, 25%, 50%, 75%, 80%, 85%, 90%, 95%, 97%, or 99% of Compound I. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

Example 1

Preparation of 2-[6-(3-amino-piperidin-1-yl)-3-methyl-2,4-dioxo-3,4-dihydro-2H-pyrimidin-1-ylmethyl]-4-fluoro-benzonitrile succinate (Compound I)

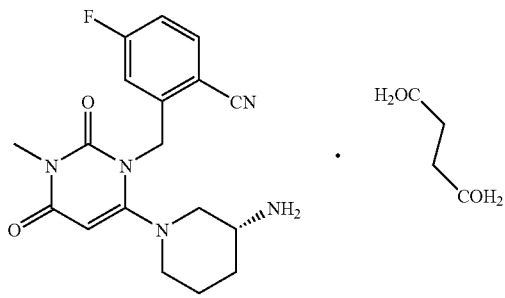

Compound I may be prepared by the follow synthetic route (Scheme 1)

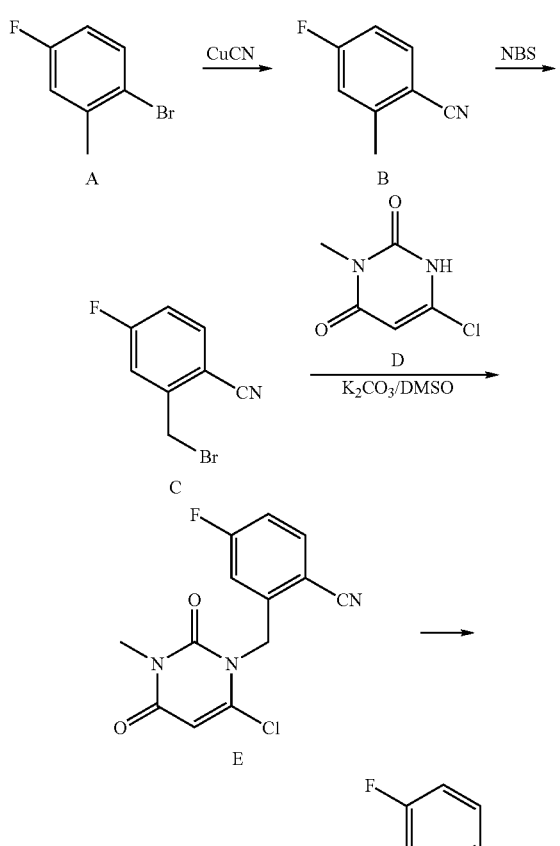

A. Preparation of 4-fluoro-2-methylbenzonitrile (Compound B)

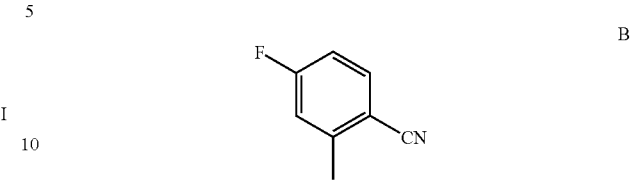

Compound B was prepared by refluxing a mixture of 2-bromo-5-fluoro-toluene (Compound A) (3.5 g, 18.5 mmol) and CuCN (2 g, 22 mmol) in DMF (100 mL) for 24 hours. The reaction was diluted with water and extracted with hexane. The organics were dried over $MgSO_4$ and the solvent removed to give product B (yield 60%). $^1$H-NMR (400 MHz, $CDCl_3$): δ 7.60 (dd, J=5.6, 8.8 Hz, 1H), 6.93-7.06 (m, 2H), 2.55 (s, 3H).

B. Preparation of 2-bromomethyl-4-fluorobenzonitrile (Compound C)

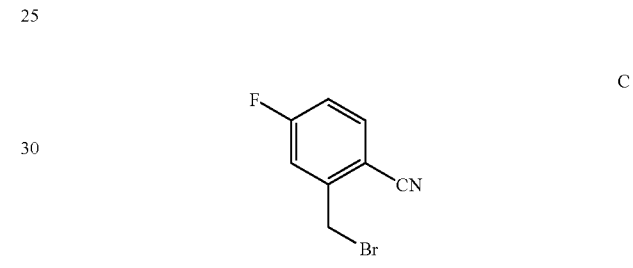

Compound C was prepared by refluxing a mixture of 4-fluoro-2-methylbenzonitrile (Compound B) (2 g, 14.8 mmol), N-bromosuccinimide (NBS) (2.64 g, 15 mmol) and azo-bis-isobutyronitrile (AIBN) (100 mg) in $CCl_4$ under nitrogen for 2 hours. The reaction was cooled to room temperature. The solid was removed by filtration. The organic solution was concentrated to give the crude product the form of an oil, which was used in the next step without further purification. $^1$H-NMR (400 MHz, $CDCl_3$): δ 7.68 (dd, J=5.2, 8.4 Hz, 1H), 7.28 (dd, J=2.4, 8.8 Hz, 1H), 7.12 (m, 1H), 4.6 (s, 2H).

C. Preparation of 2-(6-chloro-3-methyl-2,4-dioxo-3,4-dihydro-2H-pyrimidin-1-ylmethyl)-4-fluoro-benzonitrile (Compound D)

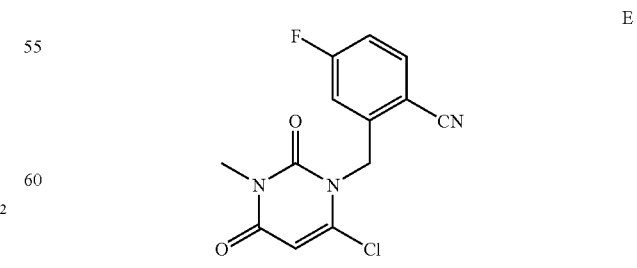

Compound E was prepared by stirring a mixture of crude 3-methyl-6-chlorouracil D (0.6 g, 3.8 mmol), 2-bromomethyl-4-fluorobenzonitrile (0.86 g, 4 mmol) and $K_2CO_3$ (0.5 g, 4 mmol) in DMSO (10 mL) at 60° C. for 2 hours. The reaction was diluted with water and extracted with EtOAc. The organics were dried over MgSO$_4$ and the solvent removed. The residue was purified by column chromatography. 0.66 g of the product was obtained (yield: 60%). $^1$H-NMR (400 MHz, CDCl$_3$): δ 7.73 (dd, J=7.2, 8.4 Hz, 1H), 7.26 (d, J=4.0 Hz, 1H), 7.11-7.17 (m, 1H), 6.94 (dd, J=2.0, 9.0 Hz, 1H), 6.034 (s, 2H), 3.39 (s, 3H). MS (ES) [m+H] calc'd for C$_{13}$H$_9$ClFN$_3$O$_2$, 293.68; found 293.68.

D. Preparation of 2-(6-chloro-3-methyl-2,4-dioxo-3, 4-dihydro-2H-pyrimidin-1-ylmethyl)-4-fluoro-benzonitrile (Compound F)

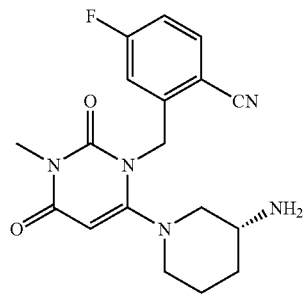

Compound F was prepared by mixing and stirring 2-(6-chloro-3-methyl-2,4-dioxo-3,4-dihydro-2H-pyrimidin-1-ylmethyl)-4-fluoro-benzonitrile (Compound E) (300 mg, 1.0 mmol), (R)-3-amino-piperidine dihydrochloride (266 mg, 1.5 mmol) and sodium bicarbonate (500 mg, 5.4 mmol) in a sealed tube in EtOH (3 mL) at 100° C. for 2 hrs. The final compound was obtained as trifluoroacetate (TFA) salt after HPLC purification. $^1$H-NMR (400 MHz, CD$_3$OD): δ. 7.77-7.84 (m, 1H), 7.16-7.27 (m, 2H), 5.46 (s, 1H), 5.17-5.34 (ABq, 2H, J=35.2, 15.6 Hz), 3.33-3.47 (m, 2H), 3.22 (s, 3H), 2.98-3.08 (m, 1H), 2.67-2.92 (m, 2H), 2.07-2.17 (m, 1H), 1.82-1.92 (m, 1H), 1.51-1.79 (m, 2H). MS (ES) [m+H] calc'd for C$_{18}$H$_{20}$FN$_5$O$_2$, 357.38; found, 357.38.

E. Preparation of Compound I: the succinic acid salt of 2-(6-Chloro-3-methyl-2,4-dioxo-3,4-dihydro-2H-pyrimidin-1-ylmethyl)-4-fluoro-benzonitrile

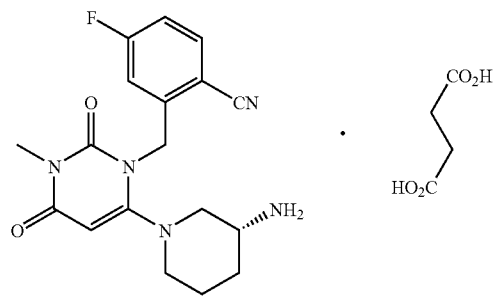

The TFA salt prepared in the above step (Example 1, Step D) was suspended in DCM, and then washed with saturated Na$_2$CO$_3$. The organic layer was dried and removed in vacuo. The benzonitrile product (approximately 10 mg) was dissolved in MeOH (1 mL) and to which succinic acid in THF (1.05 equivalents) was added. The solutions were allowed to stand for three days open to the air. If a precipitate formed, the solid was collected by filtration. If no solid formed, the mixture was concentrated in vacuo, and the succinate salt was obtained after removing the solvent. $^1$H-NMR (400 MHz, CD$_3$OD): δ. 7.77-7.84 (m, 1H), 7.12-7.26 (m, 2H), 5.47 (s, 1H), 5.21-5.32 (ABq, 2H, J=32.0, 16.0 Hz), 3.35-3.5 (m, 2H), 3.22 (s, 3H), 3.01-3.1 (m, 1H), 2.69-2.93 (m, 2H), 2.07-2.17 (m, 1H), 1.83-1.93 (m, 1H), 1.55-1.80 (m, 2H). MS (ES) [m+H] calc'd for C$_{18}$H$_{20}$FN$_5$O$_2$, 357.38; found, 357.38.

Compound I such prepared was found to be crystalline as determined by x-ray powder diffraction analysis (FIG. 1). The crystal material was designated Form A.

Example 2

Approximate Solubility of Compound I in Different Solvents

Compound I prepared by the method described in Example 1 was used for the solubility study. Solvents and other reagents were of ACS or HPLC grade and were used as received.

A weighed sample (typically about 20-25 mg) of Compound I was treated at ambient temperature with aliquots (typically ≧50 μL) of the test solvent with sonication between additions. Solvents were either reagent or HPLC grade. Solubility was estimated from the total volume of solvent used to obtain a clear solution, as determined by visual inspection. Solubility is expressed as "less than" when dissolution was not observed. If dissolution occurred after the last aliquot was added then solubility is expressed as "greater than or equal to" (≧). The actual solubilities may be greater than determined, due to over addition of solvent (large aliquots) or slow dissolution rates. Approximate solubilities of Compound I are summarized in Table A. The solubility values have been rounded to the nearest whole number and are reported to the nearest mg/mL.

TABLE A

Approximate Solubilities of Compound I

| Solvent | Solubility (mg/mL)[a] |
|---|---|
| Acetone | 2 |
| Acetonitrile (ACN) | <1 |
| Dichloromethane (DCM) | <1 |
| Dimethyl Formamide (DMF) | 68 |
| 1,4-Dioxane | <1 |
| Ethanol (EtOH) | 2 |
| Ethyl Acetate (EtOAc) | <1 |
| di-Ethyl ether | <1 |
| Hexanes | <1 |
| 2-Propanol (IPA) | <1 |
| Methanol (MeOH) | 20 |
| Tetrahydrofuran (THF) | <1 |
| Toluene | <1 |
| Trifluoroethanol (TFE) | >200 |
| Water (H$_2$O) | 51 |
| ACN:H$_2$O (85:15) | 101 |
| EtOH:H$_2$O (95:5) | 5 |
| IPA:H$_2$O (88:12) | 11 |

[a]Approximate solubilities are calculated based on the total solvent used to give a solution; actual solubilities may be greater because of the volume of the solvent portions utilized or a slow rate of dissolution. Solubilities are reported to the nearest mg/mL.

Example 3

Polymorph Screen

Compound I as prepared by the method described in Example 1 was used as the starting material for the polymorph screen. Solvents and other reagents were of ACS or HPLC grade and were used as received.

A. Sample Generation.

Solids for form identification were prepared via the following methods from Compound I.

1. Fast Evaporation (FE)

A solution of Compound I was prepared in test solvents. The sample was placed in the hood, uncovered, to evaporate under ambient conditions. The solids were analyzed by XRPD for form identification.

2. Slow Evaporation (SE)

A solution of Compound I was prepared in test solvents. The sample was placed in the hood, covered with foil rendered with pinholes, to evaporate under ambient conditions. The solids were analyzed by XRPD for form identification.

3. Room Temperature (RT) Slurries

An excess amount of Compound I was slurried in test solvent on a rotating wheel for approximately 5 or 7 days. The solids were typically collected by vacuum filtration, air dried in the hood, and analyzed by XRPD for form identification.

4. Elevated Temperature Slurries

Excess Compound I was slurried in test solvents at 47° C. on a shaker block for approximately 5 days. The solids were collected by vacuum filtering, dried in the hood, and then analyzed by XRPD for form identification.

5. Slow Cooling Crystallization (SC)

A saturated or near saturated solution of Compound I was prepared at elevated temperature. The samples were filtered through warmed 0.2 µm filters into warmed vials. The heat source was turned off and the samples slowly cooled to ambient temperature. If precipitation did not occur within a day the samples were placed in the refrigerator. The samples were transferred to a freezer if precipitation did not occur within several days. The solids were collected by decanting the solvent or vacuum filtration, dried in the hood and analyzed by XRPD for form identification.

6. Crash Cooling Crystallization (CC)

A saturated or near saturated solution of Compound I was prepared at elevated temperature. The samples were filtered through warmed 0.2 µm filters into warmed vials then rapidly cooled in an acetone/dry ice or ice bath. If precipitation did not occur after several minutes the samples were placed in the refrigerator or freezer. Solids were collected by decanting solvent or vacuum filtration, dried in the hood, and then analyzed by XRPD. Samples that did not precipitate under subambient conditions after several days were evaporated in the hood and analyzed by XRPD for form identification.

7. Solvent/Antisolvent Crystallization (S/AS)

A solution of Compound I was prepared in test solvent. A miscible antisolvent was added with a disposable pipette. Precipitate was collected by vacuum filtration or decanting solvent. The samples were stored under subambient conditions if precipitation did not occur. If solids were not observed after several days the samples were evaporated in the hood. Collected solids were analyzed by XRPD for form identification.

8. Relative Humidity (RH) Stressing Experiments

Samples of Compound I were placed uncovered in approximately 58%, 88%, and 97% relative humidity jars. The samples were stored in the jars for approximately 8 days. The solids were collected and analyzed by XRPD for form identification.

9. Lyophilization

Compound I was dissolved in water in a glass vial. The solution was frozen by swirling the vial in an acetone/dry ice bath. The frozen sample was placed on the lyophilizer until all of the frozen solvent was removed. The solids were collected and analyzed by XRPD for form identification.

10. Grinding Experiments

Aliquots of Compound I were ground manually with a mortar and pestle as a dry solid and a wet paste in water. The samples were ground for approximately three minutes. The solids were collected and analyzed by XRPD for form identification.

11. Dehydration Experiments

Hydrated samples of Compound I were dehydrated at ambient conditions (2 days) and in an ambient temperature vacuum oven (1 day). The solids were collected and analyzed by XRPD for form identification.

12. Vapor Stress Experiments

Amorphous Compound I was placed in acetone, ethanol, and water vapor chambers for up to eight days. The solids were collected and analyzed by XRPD for form identification.

B. Sample Characterization.

The following analytical techniques and combination thereof were used determine the physical properties of the solid phases prepared.

1. X-Ray Powder Diffraction (XRPD)

X-ray powder diffraction (XRPD) analyses were performed using an Inel XRG-3000 diffractometer equipped with a CPS (Curved Position Sensitive) detector with a 2θ (2θ) range of 120°. Real time data were collected using Cu-Kα radiation starting at approximately 4° 2θ at a resolution of 0.03° 2θ. The tube voltage and amperage were set to 40 kV and 30 mA, respectively. The pattern is displayed from 2.5 to 40° 2θ. Samples were prepared for analysis by packing them into thin-walled glass capillaries. Each capillary was mounted onto a goniometer head that is motorized to permit spinning of the capillary during data acquisition. The samples were analyzed for approximately 5 minutes. Instrument calibration was performed using a silicon reference standard. Peak picking was performed using the automatic peak picking in the Shimadzu XRD-6000 Basic Process version 2.6. The files were converted to Shimadzu format before performing the peak picking analysis. Default parameters were used to select the peaks.

2. Thermogravimetric Analysis (TGA)

Thermogravimetric (TG) analyses were performed using a TA Instruments 2950 thermogravimetric analyzer. Each sample was placed in an aluminum sample pan and inserted into the TG furnace. The furnace was first equilibrated at 25° C., then heated under nitrogen at a rate of 10° C./min, up to a final temperature of 350° C. Nickel and Alumel™ were used as the calibration standards.

3. Differential Scanning Calorimetry (DSC)

Differential scanning calorimetry (DSC) was performed using a TA Instruments differential scanning calorimeter 2920. The sample was placed into an aluminum DSC pan, and the weight accurately recorded. The pan was covered with a lid and then crimped. The sample cell was equilibrated at 25° C. and heated under a nitrogen purge at a rate of 10° C./min, up to a final temperature of 350° C. Indium metal was used as the calibration standard. Reported temperatures are at the transition maxima.

For studies of the glass transition temperature ($T_g$) of the amorphous material, the sample cell was equilibrated at ambient temperature, then heated under nitrogen at a rate of 20° C./min, up to 100° C. The sample cell was then allowed to cool and equilibrate at −20° C. It was again heated at a rate of 20° C./min up to 100° C. and then cooled and equilibrated at −20° C. The sample cell was then heated at 20° C./min up to a final temperature of 350° C. The $T_g$ is reported from the onset point of the transition.

4. Hot Stage Microscopy.

Hot stage microscopy was performed using a Linkam hot stage (model FTIR 600) mounted on a Leica DM LP microscope. The samples were prepared between two cover glasses and observed using a 20× objective with crossed polarizers and first order compensator. Each sample was visually observed as the stage was heated. Images were captured using a SPOT Insight™ color digital camera with SPOT Software v. 3.5.8. The hot stage was calibrated using USP melting point standards.

5. Thermogravimetric-Infrared (TG-IR)

Thermogravimetric infrared (TG-IR) analyses were acquired on a TA Instruments thermogravimetric (TG) analyzer model 2050 interfaced to a Magna 560® Fourier transform infrared (FT-IR) spectrophotometer (Thermo Nicolet) equipped with an Ever-Glo mid/far IR source, a potassium bromide (KBr) beamsplitter, and a deuterated triglycine sulfate (DTGS) detector. The TG instrument was operated under a flow of helium at 90 and 10 cc/min for the purge and balance, respectively. Each sample was placed in a platinum sample pan, inserted into the TG furnace, accurately weighed by the instrument, and the furnace was heated from ambient temperature to 250° C. at a rate of 20° C./min. The TG instrument was started first, immediately followed by the FT-IR instrument. Each IR spectrum represents 32 co-added scans collected at a spectral resolution of 4 cm$^{-1}$. A background scan was collected before the beginning of the experiment. Wavelength calibration was performed using polystyrene. The TG calibration standards were nickel and Alumel™. Volatiles were identified from a search of the High Resolution Nicolet TGA Vapor Phase spectral library.

6. Fourier Transform Infrared Spectroscopy (FT-IR)

Infrared spectra were acquired on a Magna-IR 560® or 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. A diffuse reflectance accessory (the Collector™, Thermo Spectra-Tech) was used for sampling. Each spectrum represents 256 co-added scans collected at a spectral resolution of 4 cm$^{-1}$. Sample preparation consisted of physically mixing the sample with KBr and placing the sample into a 13-mm diameter cup. A background data set was acquired on a sample of KBr. A Log 1/R(R=reflectance) spectrum was acquired by taking a ratio of these two data sets against each other. Wavelength calibration was performed using polystyrene. Automatic peak picking was performed using Omnic version 7.2.

7. Fourier Transform Raman Spectroscopy (FT-Raman)

FT-Raman spectra were acquired on a Raman accessory module interfaced to a Magna 860 Fourier transform infrared (FT-IR) spectrophotometer (Thermo Nicolet). This module uses an excitation wavelength of 1064 nm and an indium gallium arsenide (InGaAs) detector. Approximately 0.5 W of Nd:YVO$_4$ laser power was used to irradiate the sample. The samples were prepared for analysis by placing the material in a glass tube and positioning the tube in a gold-coated tube holder in the accessory. A total of 256 sample scans were collected from at a spectral resolution of 4 cm$^{-1}$, using Happ-Genzel apodization. Wavelength calibration was performed using sulfur and cyclohexane. Automatic peak picking was performed using Omnic version 7.2.

8. Solid State Nuclear Magnetic Resonance Spectroscopy ($^{13}$C-NMR)

The solid-state $^{13}$C cross polarization magic angle spinning (CP/MAS) NMR spectrum was acquired at ambient temperature on a Varian$^{UNITY}$ INOVA-400 spectrometer (Larmor frequencies: $^{13}$C=100.542 MHz, $^{1}$H=399.799 MHz). The sample was packed into a 4 mm PENCIL type zirconia rotor and rotated at 12 kHz at the magic angle. The spectrum was acquired with phase modulated (SPINAL-64) high power $^{1}$H decoupling during the acquisition time using a $^{1}$H pulse width of 2.2 μs (900), a ramped amplitude cross polarization contact time of 5 ms, a 30 ms acquisition time, a 10 second delay between scans, a spectral width of 45 kHz with 2700 data points, and 100 co-added scans. The free induction decay (FID) was processed using Varian VNMR 6.1C software with 32768 points and an exponential line broadening factor of 10 Hz to improve the signal-to-noise ratio. The first three data points of the FID were back predicted using the VNMR linear prediction algorithm to produce a flat baseline. The chemical shifts of the spectral peaks were externally referenced to the carbonyl carbon resonance of glycine at 176.5 ppm.

9. Solution Nuclear Magnetic Resonance Spectroscopy ($^{1}$H-NMR)

The solution $^{1}$H NMR spectrum was acquired at ambient temperature with a Varian$^{UNITY}$ INOVA-400 spectrometer at a $^{1}$H Larmor frequency of 399.803 MHz. The sample was dissolved in methanol. The spectrum was acquired with a $^{1}$H pulse width of 8.4 μs, a 2.50 second acquisition time, a 5 second delay between scans, a spectral width of 6400 Hz with 32000 data points, and 40 co-added scans. The free induction decay (FID) was processed using Varian VNMR 6.1C software with 65536 points and an exponential line broadening factor of 0.2 Hz to improve the signal-to-noise ratio. The spectrum was referenced to internal tetramethylsilane (TMS) at 0.0 ppm.

10. Moisture Sorption/Desorption Analysis

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Crystallization experiments performed for the polymorph screen are summarized in Tables B and C. Table B summarizes the crystallization experiments in various solvent. Table C summarized the crystallization experiments in various solvents/antisolvents.

TABLE B

Crystallization Experiments of Compound I from Solvents

| Solvent | Conditions[a] | XRPD Form[b] | Color/Morphology |
|---|---|---|---|
| Acetone | FE | A | white, aggregates of birefringent aciculars |
|  |  | A | white + yellow, needles |
|  | SE | A | light yellow, needles + blades in large rosettes |
|  |  | — | light yellow, spherulite |
|  | partial dissolution of the light yellow spherulite precipitated from acetone by SE | A | white, needles |
|  | RT slurry, 7 days | A | white, needles |
|  | SC (60° C.) | A | white, tiny needles |
|  | CC | qty. too small | white, tiny needles/spherulites |
| ACN | FE | A-peaks, PO | white, needles/rosettes |
|  | SE | A | white, needles |
|  | RT slurry, 7 days | A | white, needles |
|  | SC (60° C.) | A | white, blades/spherulites |
| DCM | RT slurry, 7 days | A | white, needles |
| 1,4-Dioxane | FE | low crystallinity A | yellow, needles, glass |
|  | RT slurry, 7 days | A | white, needles |
|  | SC (60° C.) | A | white, needles |
| DMF | FE | A | off white, needles |
| EtOH | FE | A | off white, needles/rosettes + unknown morphology |
|  |  | A | off white, needles, spherulites |
|  | SE | A | white, needles/spherulites |
|  | SC (60° C.) | A | off white, spherulites |
|  | CC-evaporated | A | white, needles, spherulites |
| EtOAc | RT slurry, 7 days | A | white, needles |
|  | SC (60° C.) | A | white, needles/spherulites |
| di-Ethyl ether | RT slurry, 7 days | A | white, needles |
| Hexanes | RT slurry, 7 days | A | white, needles |
| MeOH | FE | A | white, irregularly shaped, w/birefringent acicular regions |
|  |  | A | off white, needles, spherulites |
|  | SE | A | white, needles |
|  | RT slurry, 5 days | A | white, tiny needles |
|  | SC (60° C.) | A | yellow, spherulites of tiny needles |
|  | CC | A | white, needles |
| IPA | RT slurry, 7 days | A | white, needles |
|  | SC (60° C.) | Pattern C | white, needles |
|  |  | C-peaks |  |
|  |  | low crystallinity A | white, spherulites |
|  |  | low crystallinity A + B | white, spherulites |
|  |  | low crystallinity A + B | white, needles, spherulites |
|  |  | low crystallinity A + B | white, unknown, spheres |
|  |  | A | white, spheres |
|  |  | low crystallinity material | white, needles + unknown |
|  |  | low crystallinity material | white, unknown, spheres |
|  |  | low crystallinity A + B | white, unknown |
|  |  | low crystallinity A + B | white, needles, spheres |
|  |  | low crystallinity material | white, needles + unknown |
|  |  | low crystallinity A + B | white, needles |
| THF | RT slurry, 7 days | A | white, needles |
|  | SC (60° C.) | low crystallinity A | white, tiny needles |
| Toluene | RT slurry, 7 days | A | white, needles |
| TFE | FE | A | off white, needles, glass |
|  | SE | A | off white, needles |
| Water | FE | A | white, needles/rosettes |
|  |  | A | white, off white edges, needles/spherulites |
|  |  | A | white, brown edges, needles/spherulites |

TABLE B-continued

Crystallization Experiments of Compound I from Solvents

| Solvent | Conditions[a] | XRPD Form[b] | Color/Morphology |
|---|---|---|---|
| | SE | A | off white, some pink spots, needles |
| | | A | white w/brown edges, needles |
| | | A | white w/brown edges, needles |
| | RT slurry, 5 days | A | off white, needles |
| | SC (60° C.) | A | off white, needles/spherulites |
| Water | CC | A + B + peaks | white, needles/spherulites |
| | lyophilization | amorphous | — |
| ACN:H$_2$O (85:15) | FE | A | white, aggregates of birefringent aciculars |
| | SE | A | off white, needles/spherulites |
| EtOH:H$_2$O (95:5) | FE | A + 1 peak | white + light yellow, needles/rosettes |
| | SE | A | white, needles |
| | RT slurry, 7 days | A | white, needles |
| | elevated temp. slurry | A | white, light yellow, small sticky orange-ish spot, needles |
| | CC | A + B | white, blades, needles |
| | CC | A + B | white, blades, needles |
| | | A + B | off white, blades/spherulites |
| IPA:H$_2$O (88:12) | FE | low crystallinity A + B | white, fine blades, aciculars, birefringent |
| | SE | A + B | white, pink spots, needles |
| | | A + B | white, needles |
| | partial SE | A + B | white, needles |
| | RT slurry, 5 days | A | white, tiny needles |
| | SC (60° C.) | A + B | white, needles, spherulites |
| | | A + B | white, needles |
| | CC | A + B | white, needles/spherulites |
| THF:H$_2$O (9:1) | RT slurry, 13 days | A + E + G peaks | white, needles |
| | elevated temp. slurry | A | light yellow, white, needles |
| | SC (60° C.) | A + B | white, needles/blades |
| | | A + B | white needles, spherulites |
| | | A + B | |
| | | A + minor E | off white, needles |
| | | A + F peaks | white, needles |
| | SC (60° C.), 70° C., 1 day | A + F peaks | white, glass, needles |
| | damp 2333-34-03 | A + E + G peaks | white, needles |
| | SC (60° C.), 70° C., 3 days | A + F peaks | off white, glass + needles |
| — | Post MB of a sample prepared by CC from EtOH:H$_2$O (95:5) | A + B | — |
| | Post MB of a lyophilized sample from H$_2$O solution | low crystallinity A | — |
| | Post MB of a sample crystallized from H$_2$O/ACN | A + small quantity of E | — |
| | ground (dry) ~3 minutes | A | — |
| — | ground (wet) ~3 minutes | A | — |
| | Form A + B, under vacuum, overnight | A | off white, needles |
| | Form A + B, at ambient, ~2 days | A | off white, needles |

[a]FE = fast evaporation; SE = slow evaporation; RT = room temperature; SC = slow cool; CC = crash cool, MB = moisture sorption/desorption analysis
[b]qty = quantity; PO = preferred orientation

TABLE C

Crystallization Experiments of Compound I in Various Solvent/Antisolvent

| Solvent | Antisolvent | Form | Color/Morphology |
|---|---|---|---|
| DMF | ACN | A | off white, needles/spherulites |
|  | toluene | A | white, needles/spherulites |
|  | EtOAc | A | white, spherulites |
|  | IPA | A | white, needles/spherulites |
| MeOH | ACN | $A^a$ | white + yellow, needles |
|  | DCM | $A^a$ | white + yellow, needles |
| TFE | IPE | A | white, tiny spherulites |
|  | ACN | A | off white, needles, spherulites |
|  | IPA | A | white, tiny spherulites |
|  | EtOAc | A | white, tiny spherulites |
| $H_2O$ | ACN | $D^a$ | off white, needles |
|  |  | $A^a$ | white, brown edges, needles/blades |
|  |  | $E^a$ | off white, needles |
|  |  | $A^a$ | white + light yellow, needles |
|  |  | $A^a$ | white, off white at edges, needles/spherulites |
|  |  | $A^a$ | white w/brown edges, needles |
|  |  | $A^a$ | white w/brown edges, needles |
|  |  | $A^a$ | off white, brown at edges, needles/spherulites |
|  |  | $A^a$ | white, needles |
|  |  | $A^a$ | white, needles |
|  |  | A | white/off white, needles |
|  | dioxane | $A + B^a$ | off white, needles |
|  | THF | $A^a$ | light yellow solid/paste, needles |

$^a$precipitated by evaporation of solvent

Example 4

Preparation of Form A+B

Approximately 40 mg of Compound I starting material was dissolved in 4 mL of isopropanol:water (88:12). The vial was covered with a piece of aluminum foil rendered with five pinholes for slow evaporation. Solids yielding Form A+B were recovered after 14 days.

Example 5

Preparation of Form C

A slurry of Compound I starting material (40 mg) in IPA (8 mL) was stirred on a hot plate set to 60° C., 300 rpm for approximately 5 hours. The slurry was filtered through a warmed 0.2 μm nylon filter into a warmed vial, and the hot plate was turned off to slow cool the solution. The sample was stored at ambient temperature for approximately one day, then transferred to a refrigerator for approximately 3 days. A clear solution was observed. After 3 days in the refrigerator, the sample was transferred to a freezer for approximately 5 days. The solids were collected by vacuum filtration and dried in the hood.

Example 6

Preparation of Form D

A sample of Compound I starting material (40 mg) was dissolved in water (400 μl). The solution was filtered through a 0.2 μm nylon filter into a clean vial. Approximately half a disposable pipette full of acetonitrile was added to the water solution. No precipitation was observed. The sample was placed into a refrigerator for approximately 12 days. Precipitates were not observed. The solution was placed in the hood, uncovered, to evaporate. Solids yielding Form D were recovered after two days.

Example 7

Preparation of Form E

A sample of Compound I (40 mg) was dissolved in water (400 μl). The solution was filtered through a 0.2 μm nylon filter into a clean vial. Approximately ¾ a disposable pipette full of acetonitrile was added to the water solution. The sample was agitated by hand. No precipitation was observed. The solution was placed in the hood, uncovered, to evaporate. Solids were recovered after 10 days.

Example 8

Preparation of Form A+F

A sample of Compound I (51 mg) was dissolved in 800 μl of a THF:water (9:1) solution. The sample was stirred on a hot plate set at 60° C., 300 rpm for approximately one hour. The hot plate was turned off to allow the clear solution to slow cool. After the sample reached room temperature, it was placed in the refrigerator to induce precipitation. Precipitates were observed after approximately two days. The solvent was decanted and the solids allowed to air dry.

Example 9

Preparation of Form A+E+G

A slurry of Compound I (79 mg) was prepared in 1 mL of THF:water (9:1). The sample was slurried at ambient conditions for 13 days. The solids were collected by filtration and air dried. The resulting solids yielded a mixture of Forms A+E+G.

Example 10

Preparation of Amorphous Form

A sample of Compound I (40 mg) was dissolved in 1000 μl of water. The solution was filtered through a 0.2 μm nylon filter into a clean vial then frozen in a dry ice/acetone bath. The vials were covered with a Kimwipe then placed on a lyophilizer overnight. The resulting solids yielded Amorphous Form.

Example 11

Characterization of Form A

Material prepared by the procedure of Example 1 was designated as Form A. The material was characterized by XRPD, TGA, DSC, hot stage microscopy, FT-IR, FT-Raman, $^1$H NMR, and $^{13}$C NMR. The analyses were conducted according to the procedures outlined in Section B of Example 3.

The characteristic spectra and thermograms for Form A are reported in FIGS. 1-7. The characterization data are summarized in Table D.

TABLE D

Characterization Data of Form A of Compound I

| Sample Source | Technique | Analysis/Result |
|---|---|---|
| Prepared by procedure of Example 1 | XRPD | crystalline (FIG. 1) |
| | TGA | insignificant weight loss from 25° C. to 165° C. (FIG. 2) |
| | DSC | endotherm 195° C. (FIG. 2) |
| | Hot stage microscopy | T = 26° C. |
| | | T = 34° C. |
| | | T = 89° C. |
| | | T = 110° C. |
| | | T = 177° C., melt onset |
| | | T = 184° C., approximate melting point |
| | IR | FIG. 4 A-D |
| | Raman | FIG. 5 A-D |
| | $^1$H NMR | consistent with chemical structure (FIG. 6) |
| | $^{13}$C NMR | consistent with chemical structure (FIG. 7) |

T = temperature

Example 12

Characterization of Form A+B

Form A+B material was prepared according to Example 4.
The material was characterized by XRPD, TGA, DSC, hot stage microscopy, TG-IR and moisture sorption/desorption analysis. The analyses were conducted according to the procedures outlined in Section B of Example 3.

The characteristic spectra and thermograms for Form A+B are reported in FIGS. 8-13. The characterization data of Form A+B are summarized in Table E.

TABLE E

Characterization Data of Form A + B

| Sample Source | Technique | Analysis/Result |
|---|---|---|
| Crystallized from IPA:H$_2$O (88:12), by slow evaporation (SE) | XRPD | Crystalline (FIG. 8) |
| | TGA | 2.0% weight loss from 25° C. to 98° C. 0.7% weight loss from 98° C. to 175° C. (FIG. 9) |
| | DSC | broad endotherm 100° C. small endotherm 138° C., 163° C. endotherm 193° C. (FIG. 12) |
| | Hot Stage | T = 26° C., birefringence with extinction |
| | | T = 99° C., no changes observed |
| | | T = 145° C., no changes observed |
| | | T = 165° C., no changes observed |
| | | T = 179° C., some particles appear to be melting |
| | | T = 185° C., particles appear to be melting |
| | | T = 188° C., possible end of melt, approximate melting point |
| | | T = 233° C., sample appears brown, suggesting decomposition |
| | | T = 302° C., sample brown, cooled to approximately 30° C., no recrystallization |
| | TG-IR | 2.4% weight loss from 21° C. to 105° C. and water by IR (FIGS. 10-11) |
| Crystallized from EtOH:H$_2$O (95:5) by crash cooling (CC) | MB | 0.7% weight loss on equilibration at 5% RH 1.2% weight gain from 5-95% RH 1.2% weight lost from 95-5% RH (FIG. 13) |

T = temperature,
RH = relative humidity, and
MB = moisture sorption/desorption analysis

Example 13

Characterization of Form C

Form C material was prepared according to Example 5. The material was characterized by XRPD. The XRPD spectrum of Form C is reported in FIG. 14.

Example 14

Characterization of Form D

Form D material was prepared according to Example 6.

The material was characterized by $^1$H NMR, XRPD, TGA, DSC, TG-IR, and hot stage microscopy. The characterization analyses were conducted according to the procedures outlined in Section B of Example 3. The characteristic spectra and thermograms for Form D are reported in FIGS. 15-19. The characterization data of Form D are summarized in Table F.

TABLE F

Characterization Data of Form D

| Sample Source | Technique | Analysis/Result |
|---|---|---|
| H$_2$O/ACN evaporated | XRPD | crystalline (FIG. 15) |
| | TGA | ~8% weight lost on equilibration, and 21.9% weight loss from 25° C. to 85° C. (FIG. 16) |
| | DSC | broad, noisy endotherm at 88° C., endotherm at 107° C. and 192° C. (FIG. 19) |
| | TG-IR | 24.0% weight loss when heated from 20° C. to 100° C. due to evaporation of water (FIGS. 17-18) |
| | Hot stage microscopy | T = 25° C., birefringence with extinction |
| | | T = 84° C., no changes |
| | | T = 90° C., no changes |
| | | T = 115° C., no changes |
| | | T = 184° C., small particles appear to be melting |
| | | T = 188° C., melt appears to continue |
| | | T = 192° C., approximate end of melt |
| | | T = 218° C., condensation on the cover slip |
| | | T = 230° C., melt appears to have evaporated and condensed on the cover slip. Cooled to ambient, no recrystallization |
| | $^1$H NMR | consistent with chemical structure |

T = temperature,
MB = moisture sorption/desorption analysis

Example 15

Characterization of Form E

Form E material was prepared according to Example 7.

The material was characterized by $^1$H NMR, XRPD, TGA, DSC, TG-IR, and hot stage microscopy, moisture sorption/desorption analysis (m s/des). The characterization analyses were conducted according to the procedures outlined in Section B of Example 3.

The characteristic spectra and thermograms for Form D are reported in FIGS. 20-23. The moisture sorption and desorption isotherm of Form E is reported in FIG. 23. The characterization data of Form E are summarized in Table G.

TABLE G

Characterization Data of Form E

| Sample Source | Technique | Analysis/Result |
|---|---|---|
| H₂O/ACN evaporated | XRPD | Crystalline (FIG. 20) |
| | TGA | 2.6% weight loss from 25° C. to 85° C. (FIG. 21) |
| | DSC | small endotherms at 59° C., 75° C.; forked endotherms at 107° C., 110° C., 114° C.; and endotherm at 192° C. (FIG. 22) |
| | Hot stage microscopy | T = 26° C., birefringence with extinction<br>T = 59° C., changes in birefringence<br>T = 81° C., changes in birefringence<br>T = 124° C., no changes, refocused<br>T = 169° C., needles appear to be forming<br>T = 179° C., more needles, possible melt onset<br>T = 183° C., continued melt<br>T = 185° C., approximate end of melt<br>T = 208° C., sample appears brown, decomposition<br>T = 250° C., sample appears brown |
| | MB | 1.3% weight loss on equilibration, 5.4% weight gain from 5-95% RH, and 5.5% weight lost from 95-5% RH (FIG. 23). |
| | ¹H NMR | consistent with chemical structure |

T = temperature,
RH = relative humidity,
MB = moisture sorption/desorption analysis

Example 16

Characterization of Form A+F

Form A+F material was prepared according to Example 8. The material was characterized by XRPD. The resulted XRPD spectrum of Form A+F is reported in FIG. 24.

Example 17

Characterization of Form G

Form A+E+G material was prepared according to Example 9. The material was characterized by XRPD. The resulted XRPD spectrum of Form A+E+G is reported in FIG. 25.

Example 18

Characterization of Amorphous Form

The amorphous form of Compound I was prepared by according to Example 10.

Amorphous Form material was characterized by XRPD TGA, DSC, hot stage microscopy, and moisture sorption/desorption analysis. The glass transition temperature of Form A was evaluated using the procedure outlined in Example 3, Section B-3. The material resulted after the moisture sorption/desorption analysis was characterized by XRPD.

The characteristic spectra and thermograms of Amorphous Form are reported in FIGS. 26-29. The moisture sorption and desorption isotherm of Amorphous Form is reported in FIG. 30. The DSC thermogram for the determination of glass transition temperature of Amorphous Form is reported in FIG. 31. The characterization data of Amorphous Form is summarized in Table H below.

TABLE H

Characterization Data of Amorphous Form

| Sample Source | Technique | Analysis/Result |
|---|---|---|
| Lyophilized from Compound I in water | XRPD | Amorphous (FIG. 26) |
| | TGA | 1.8% weight loss from 25° C. to 95° C. (FIG. 27) |
| | DSC | slightly concave baseline to exotherm 130° C. endotherm 194° C. (FIG. 28) approximate glass transition at 82° C., exotherm at 138° C. and endotherm 199° C. (FIG. 29) |
| | Hot stage microscopy | T = 25° C., some particles appear birefringent with extinction<br>T = 100° C. no changes<br>T = 116° C., appears to be recrystallizing<br>T = 131° C., appears to be recrystallizing<br>T = 145° C., no changes<br>T = 174° C., possible start of melt<br>T = 185° C., continued melt<br>T = 188° C., possible end of melt<br>T = 207° C., no change |
| | MB | 1.0% weight lost on equilibration at 5% RH, 4.4% weight gain from 5-95% RH, and 4.7% weight lost from 95-5% RH (FIG. 30) |
| | Post MB XRPD | Crystalline, Form A (FIG. 31) |

T = temperature,
RH = relative humidity,
MB = moisture sorption/desorption analysis

Example 19

Relative Humidity Stressing Experiments

Aliquots of Form A of Compound I were stored under approximately 50% and 97% relative humidity for 29 days. An aliquot of a mixture of Form A+B was stressed at 88% relative humidity for 23 days. Amorphous Form was stressed at 58% and 88% relative humidity for 23 days. The solids remaining were characterized by XRPD and determined to be Form A. The result is summarized in Table 1.

TABLE I

Relative Humidity Stressing Experiments of Polymorphic Form A and Form A + B of Compound I

| % RH | Initial Form | Days | Form |
|---|---|---|---|
| 97 | A | 29 | A |
| 58 | A | 29 | A |
| 88 | A + B | 23 | A |
| 58 | amorphous | 23 | A |
| 88 | amorphous | 23 | A |

Example 20

Dehydration Experiment

Aliquots of Form A+B of Compound I were stored at ambient condition for two days and in an ambient temperature vacuum over for one day. The solids were collected and analyzed by XRPD and confirmed to be Form A.

Example 21

Slurry Interconversion Studies

Samples of mixture of Form A and Form B of Compound I were slurried in water and THF:water (9:1), for up to 13 days. The result solid materials isolated were characterized by X-Ray powder diffraction and determined to be either Form A or Form A+B. The result is summarized in Table J.

TABLE J

Slurry Experiments of Form A + B of Compound I

| Solvent | Initial Forms | Days (approximate) | Final Form |
|---|---|---|---|
| Water | A + B | went into solution, evaporated | A |
| THF:H₂O (9:1) | A + B | 13 | A + B |

Example 22

Vapor Stress of Amorphous Solid of Compound I

Solids of Amorphous Form of Compound I were stressed in acetone and ethanol vapor stress chambers for 4 days. Other aliquots of the solids were stressed in a water vapor chamber for 4 days and 8 days. The remaining solids were analyzed by XRPD. The amorphous solids convert to Form A after exposure in acetone and ethanol and convert to a mixture of Form A and Form D after exposure to water vapor. The results of these experiments are summarized in Table K.

TABLE K

Vapor Stress of Amorphous Solid of Compound I

| Solvent | Days | Color/morphology | Form |
|---|---|---|---|
| Acetone | 4 | off white, irregular | A |
| EtOH | 4 | off white, irregular | A |
| Water | 4 | off white, irregular, almost liquid/drops | A + D |
|  | 8 | white, irregular, appear "damp" | low crystallinity |

Example 23

Moisture Sorption/Desorption Study on Form A+B

Moisture sorption and desorption study was conducted on a sample of Form A+B. The sample was prepared by crashed cooling crystallization (Example 3, section A.6) of the polymorphic forms from a ethanol:water (95:5) solution of Compound I. The moisture sorption and desorption study was conducted according to the procedures outlined in Example 3, section B. 10. The data collected is plotted in FIG. 13 and summarized in Table L.

TABLE L

Moisture Sorption/Desorption of Form A + B

| Elapsed Time min | Weight mg | Weight % chg | Samp Temp ° C. | Samp RH % |
|---|---|---|---|---|
| 0.1 | 3.184 | 0.000 | 25.03 | 62.77 |
| 91.5 | 3.163 | −0.665 | 25.05 | 5.14 |
| 137.8 | 3.178 | −0.184 | 25.04 | 14.88 |
| 165.5 | 3.184 | 0.004 | 25.07 | 25.03 |
| 179.7 | 3.187 | 0.098 | 25.06 | 34.82 |
| 196.2 | 3.191 | 0.208 | 25.06 | 44.88 |

TABLE L-continued

Moisture Sorption/Desorption of Form A + B

| Elapsed Time min | Weight mg | Weight % chg | Samp Temp ° C. | Samp RH % |
|---|---|---|---|---|
| 208.7 | 3.193 | 0.284 | 25.06 | 54.95 |
| 219.7 | 3.195 | 0.347 | 25.08 | 65.00 |
| 231.9 | 3.197 | 0.406 | 25.05 | 75.01 |
| 243.8 | 3.199 | 0.466 | 25.09 | 84.92 |
| 256.6 | 3.202 | 0.563 | 25.08 | 94.67 |
| 265.2 | 3.200 | 0.510 | 25.08 | 85.01 |
| 274.2 | 3.199 | 0.456 | 25.08 | 75.35 |
| 285.2 | 3.197 | 0.406 | 25.04 | 64.94 |
| 296.5 | 3.195 | 0.353 | 25.07 | 55.02 |
| 307.3 | 3.194 | 0.299 | 25.07 | 45.07 |
| 319.3 | 3.192 | 0.237 | 25.06 | 34.92 |
| 338.5 | 3.189 | 0.149 | 25.09 | 25.11 |
| 359.7 | 3.185 | 0.020 | 25.09 | 14.96 |
| 445.9 | 3.163 | −0.658 | 25.10 | 4.83 |

Example 24

Moisture Sorption/Desorption Study on Form E

Moisture sorption and desorption study was conducted on a sample of Form E. The sample was prepared by solvent/antisolvent crystallization (Example 3, section A.7) by the addition of acetonitrile to Compound I in water. The moisture sorption and desorption study was conducted according to the procedures outlined in Example 3, section B. 10. The data collected is plotted in FIG. 23 and summarized in Table M.

TABLE M

Moisture Sorption/Desorption of Form E

| Elapsed Time min | Weight mg | Weight % chg | Samp Temp ° C. | Samp RH % |
|---|---|---|---|---|
| 0.1 | 3.704 | 0.000 | 24.77 | 35.22 |
| 138.3 | 3.657 | −1.268 | 24.77 | 5.23 |
| 154.5 | 3.660 | −1.187 | 24.78 | 14.89 |
| 170.5 | 3.664 | −1.074 | 24.78 | 24.87 |
| 184.5 | 3.669 | −0.947 | 24.78 | 34.83 |
| 203.4 | 3.676 | −0.755 | 24.78 | 44.87 |
| 253.5 | 3.695 | −0.223 | 24.79 | 55.04 |
| 281.1 | 3.716 | 0.325 | 24.78 | 65.05 |
| 301.2 | 3.726 | 0.608 | 24.78 | 74.87 |
| 322.2 | 3.756 | 1.410 | 24.79 | 84.67 |
| 415.8 | 3.860 | 4.216 | 24.78 | 94.73 |
| 452.4 | 3.764 | 1.632 | 24.77 | 85.18 |
| 471.9 | 3.739 | 0.949 | 24.78 | 75.25 |
| 487.4 | 3.727 | 0.616 | 24.78 | 65.16 |
| 499.6 | 3.718 | 0.398 | 24.78 | 55.05 |
| 512.2 | 3.713 | 0.236 | 24.78 | 45.03 |
| 526.0 | 3.708 | 0.112 | 24.79 | 35.13 |
| 543.5 | 3.703 | −0.013 | 24.79 | 25.02 |
| 557.2 | 3.700 | −0.102 | 24.79 | 14.94 |
| 730.6 | 3.655 | −1.322 | 24.77 | 5.03 |

Example 25

Moisture Sorption/Desorption Study of Amorphous Form

Moisture sorption and desorption study was conducted on a sample of Amorphous Form. The sample was prepared by lyophilolization of a solution of Compound I in water (Example 3, section A.9). The moisture sorption and desorption study was conducted according to the procedures outlined in Example 3, section B.10. The data collected is plotted in FIG. 29 and summarized in Table N.

TABLE N

| Moisture Sorption/Desorption of Amorphous Form | | | | |
|---|---|---|---|---|
| Elapsed Time min | Weight mg | Weight % chg | Samp Temp ° C. | Samp RH % |
| 0.1 | 2.720 | 0.000 | 25.04 | 41.98 |
| 84.0 | 2.694 | −0.975 | 25.06 | 5.09 |
| 113.6 | 2.704 | −0.589 | 25.06 | 14.98 |
| 158.4 | 2.716 | −0.166 | 25.05 | 24.92 |
| 277.5 | 2.743 | 0.841 | 25.04 | 34.90 |
| 392.7 | 2.785 | 2.393 | 25.03 | 45.05 |
| 470.8 | 2.844 | 4.540 | 25.02 | 54.99 |
| 508.0 | 2.910 | 6.988 | 25.02 | 64.90 |
| 654.6 | 2.732 | 0.437 | 25.02 | 74.82 |
| 703.8 | 2.745 | 0.922 | 25.03 | 84.78 |
| 806.9 | 2.813 | 3.400 | 25.02 | 94.59 |
| 877.9 | 2.748 | 1.010 | 25.02 | 85.31 |
| 957.5 | 2.725 | 0.176 | 25.02 | 74.92 |
| 1039.8 | 2.713 | −0.280 | 25.03 | 65.07 |
| 1092.3 | 2.705 | −0.545 | 25.04 | 55.11 |
| 1144.4 | 2.699 | −0.776 | 25.05 | 45.07 |
| 1179.2 | 2.695 | −0.912 | 25.05 | 35.06 |
| 1210.7 | 2.692 | −1.026 | 25.05 | 25.13 |
| 1243.6 | 2.689 | −1.148 | 25.04 | 15.06 |
| 1278.0 | 2.686 | −1.269 | 25.05 | 4.97 |

What is claimed is:

1. A composition comprising Compound I having the formula

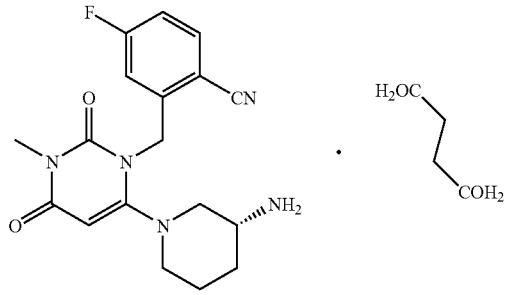

wherein a portion of Compound I is present as polymorphic Form B characterized by one or more physical properties selected from the group consisting of:
(i) an X-ray powder diffraction pattern (CuKα) comprising diffraction peaks at about 12.5, 18.83 and 24.46° 2θ; and
(ii) a differential scanning calorimetry spectrum comprising a broad endotherm at about 100° C., and two other endotherms at about 138° C. and about 163° C.

2. The composition according to claim 1, wherein greater than 0.1% of Compound I (by weight) is present in the composition as Form B.

3. The composition according to claim 1, wherein greater than 1% of Compound I (by weight) is present in the composition as Form B.

4. The composition according to claim 1, wherein greater than 10% of Compound I (by weight) is present in the composition as Form B.

5. The composition according to claim 1, wherein greater than 50% of Compound I (by weight) is present in the composition as Form B.

6. A method for preparing a composition of Compound I according to claim 1 comprising crystallizing Compound I from a solvent selected from the group consisting of: (i) isopropanol, (ii) ethanol and water (95:5), (ii) isopropanol and water (88:12), (iii) tetrahydrofuran and water (9:1), and (iv) water.

7. A method for preparing a composition of Compound I according to claim 1 comprising adding dioxane to Compound I dissolved in water.

8. A pharmaceutical composition comprising a composition of Compound I according to claim 1, and one or more pharmaceutical carriers.

9. The pharmaceutical composition according to claim 8 that is adapted for administration via a route selected from the group consisting of oral, parenteral, topical, transdermal, and pulmonary.

10. The pharmaceutical composition according to claim 8 that is in an oral dosage form selected from the group consisting of pills, tablets, capsules, emulsions, suspensions, microsuspensions, wafers, sprinkles, chewing gum, powders, lyophilized powders, granules, and troches.

11. The pharmaceutical composition according to claim 8, wherein the polymorphic form of the Compound I is at least partially preserved for a period of time following administration.

12. A composition comprising Compound I having the formula

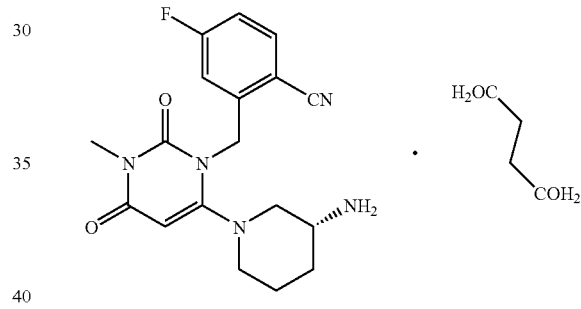

wherein a portion of Compound I is present as polymorphic Form C characterized by an X-ray powder diffraction pattern (CuKα) comprising diffraction peaks at about 5.44 and 6.07° 2θ.

13. The composition according to claim 12, wherein greater than 0.1% of Compound I (by weight) is present in the composition as Form C.

14. The composition according to claim 12, wherein greater than 1% of Compound I (by weight) is present in the composition as Form C.

15. The composition according to claim 12, wherein greater than 10% of Compound I (by weight) is present in the composition as Form C.

16. The composition according to claim 12, wherein greater than 50% of Compound I (by weight) is present in the composition as Form C.

17. A method for preparing a composition of Compound I according to claim 12 comprising crystallizing Compound I from an isopropanol solution of Compound I.

18. A pharmaceutical composition comprising a composition of Compound I according to claim 12 and one or more pharmaceutical carriers.

19. The pharmaceutical composition according to claim 18 that is adapted for administration via a route selected from the group consisting of oral, parenteral, topical, transdermal, and pulmonary.

20. The pharmaceutical composition according to claim 18 that is in an oral dosage form selected from the group consisting of pills, tablets, capsules, emulsions, suspensions, microsuspensions, wafers, sprinkles, chewing gum, powders, lyophilized powders, granules, and troches.

21. The pharmaceutical composition according to claim 18, wherein the polymorphic form of the Compound I is at least partially preserved for a period of time following administration.

22. A composition comprising Compound I having the formula

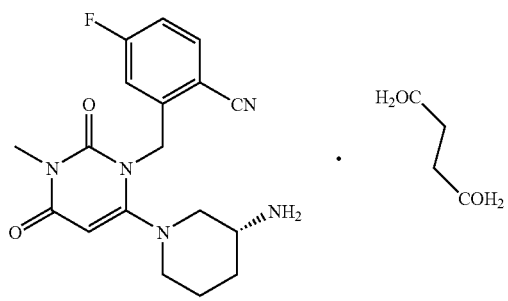

wherein a portion of Compound I is present as polymorphic Form D characterized by one or more physical properties selected from the group consisting of:
(i) an X-ray powder diffraction pattern (CuKα) comprising one diffraction peak at about 24.33° 2θ, and four other diffraction peaks selected from the group consisting of peaks at about 12.19, 16.71, 22.08, 22.88, and 23.27° 2θ;
(ii) an X-ray powder diffraction pattern (CuKα) comprising one diffraction peak at about 24.33° 2θ, and four other diffraction peaks selected from the group consisting of peaks at about 12.19, 14.04, 16.71, 17.75, 18.86, 19.96, 22.08, 22.88, 23.27, 25.02, 25.49, 26.03, and 27.99° 2θ; and
(ii) a differential scanning calorimetry spectrum comprising a broad endotherm centered at about 88° C. and two other endotherms at about 107° C. and 192° C.

23. The composition according to claim 22, wherein greater than 0.1% of Compound I (by weight) is present in the composition as Form D.

24. The composition according to claim 22, wherein greater than 1% of Compound I (by weight) is present in the composition as Form D.

25. The composition according to claim 22, wherein greater than 10% of Compound I (by weight) is present in the composition as Form D.

26. The composition according to claim 22, wherein greater than 50% of Compound I (by weight) is present in the composition as Form D.

27. A method for preparing a composition of Compound I according to claim 22, comprising adding acetonitrile to Compound I dissolved in water.

28. A pharmaceutical composition comprising a composition of Compound I according to claim 22, and one or more pharmaceutical carriers.

29. The pharmaceutical composition according to claim 28 that is adapted for administration via a route selected from the group consisting of oral, parenteral, topical, transdermal, and pulmonary.

30. The pharmaceutical composition according to claim 28 that is in an oral dosage form selected from the group consisting of pills, tablets, capsules, emulsions, suspensions, microsuspensions, wafers, sprinkles, chewing gum, powders, lyophilized powders, granules, and troches.

31. The pharmaceutical composition according to claim 28, wherein the polymorphic form of the Compound I is at least partially preserved for a period of time following administration.

32. A composition comprising Compound I having the formula

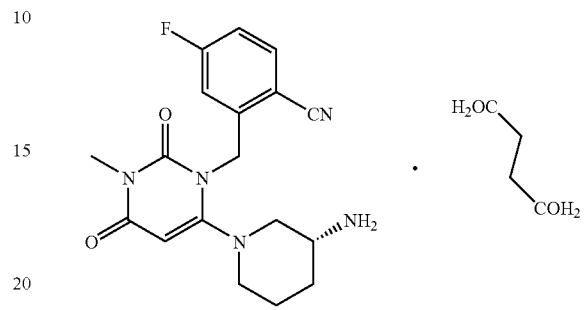

wherein a portion of Compound I is present as polymorphic Form E characterized by one or more physical properties selected from the group consisting of:
(i) an X-ray powder diffraction pattern (CuKα) comprising diffraction peaks at about 13.10, 13.94, 17.15, and 21.27° 2θ;
(ii) an X-ray powder diffraction pattern (CuKα) comprising two diffraction peaks at about 21.27 and 17.15° 2θ, and three diffraction peaks selected from the group consisting of peaks at about 11.90, 12.66, 13.10, 13.59, 13.94, 17.54, 22.03, 22.61, 24.06, 24.70, 26.31, 27.34, and 31.10° 2θ; and
(iii) a differential scanning calorimetry spectrum comprising a forked endotherm that comprises peaks at about 107° C., about 110° C. and about 114° C.

33. The composition according to claim 32, wherein greater than 0.1% of Compound I (by weight) is present in the composition as Form E.

34. The composition according to claim 32, wherein greater than 1% of Compound I (by weight) is present in the composition as Form E.

35. The composition according to claim 32, wherein greater than 10% of Compound I (by weight) is present in the composition as Form E.

36. The composition according to claim 32, wherein greater than 50% of Compound I (by weight) is present in the composition as Form E.

37. A method for preparing a composition of Compound I according to claim 32, comprising: adding acetonitrile to Compound I dissolved in water.

38. A pharmaceutical composition comprising a composition of Compound I according to claim 32, and one or more pharmaceutical carriers.

39. The pharmaceutical composition according to claim 38 that is adapted for administration via a route selected from the group consisting of oral, parenteral, topical, transdermal, and pulmonary.

40. The pharmaceutical composition according to claim 38 that is in an oral dosage form selected from the group consisting of pills, tablets, capsules, emulsions, suspensions, microsuspensions, wafers, sprinkles, chewing gum, powders, lyophilized powders, granules, and troches.

41. The pharmaceutical composition according to claim 38, wherein the polymorphic form of the Compound I is at least partially preserved for a period of time following administration.

42. A composition comprising Compound I having the formula

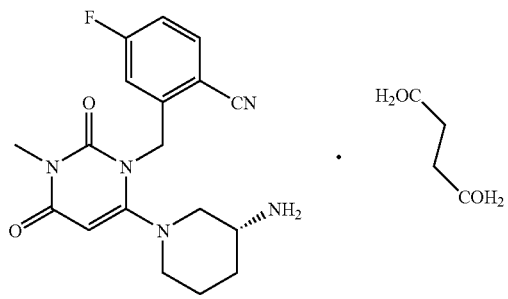

wherein a portion of Compound I is present as polymorphic Form F characterized by an X-ray powder diffraction pattern (CuKα) comprising diffraction peaks at about 12.39, 20.63, 26.03, and 30.05° 2θ.

43. The composition according to claim 42, wherein greater than 0.1% of Compound I (by weight) is present in the composition as Form F.

44. The composition according to claim 42, wherein greater than 1% of Compound I (by weight) is present in the composition as Form F.

45. The composition according to claim 42, wherein greater than 10% of Compound I (by weight) is present in the composition as Form F.

46. The composition according to claim 42, wherein greater than 50% of Compound I (by weight) is present in the composition as Form F.

47. A method of preparing a composition of Compound I according to claim 42 comprising: crystallizing Compound I from tetrahydrofuran and water solution of Compound I.

48. A pharmaceutical composition comprising a composition of Compound I according to claim 42, and one or more pharmaceutical carriers.

49. The pharmaceutical composition according to claim 48 that is adapted for administration via a route selected from the group consisting of oral, parenteral, topical, transdermal, and pulmonary.

50. The pharmaceutical composition according to claim 48 that is in an oral dosage form selected from the group consisting of pills, tablets, capsules, emulsions, suspensions, microsuspensions, wafers, sprinkles, chewing gum, powders, lyophilized powders, granules, and troches.

51. The pharmaceutical composition according to claim 48, wherein the polymorphic form of the Compound I is at least partially preserved for a period of time following administration.

52. A composition comprising Compound I having the formula

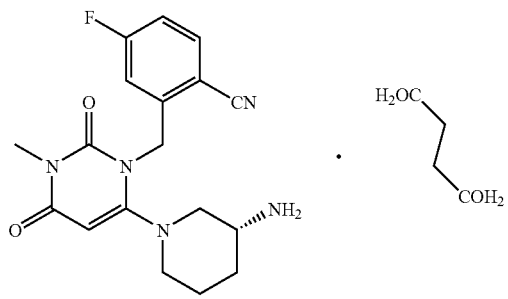

wherein a portion of Compound I is present as polymorphic Form G characterized by an X-ray powder diffraction pattern (CuKα) comprising five or more diffraction peaks selected from the group consisting of diffraction peaks at about 13.22, 14.23, 18.62, 19.77, 24.36, 25.06, and 30.71° 2θ.

53. The composition according to claim 52, wherein greater than 0.1% of Compound I (by weight) is present in the composition as Form G.

54. The composition according to claim 52, wherein greater than 1% of Compound I (by weight) is present in the composition as Form G.

55. The composition according to claim 52, wherein greater than 10% of Compound I (by weight) is present in the composition as Form G.

56. The composition according to claim 52, wherein greater than 50% of Compound I (by weight) is present in the composition as Form G.

57. A method for preparing a composition of Compound I according to claim 52 comprising: crystallizing Compound I from a tetrahydrofuran and water solution of Compound I.

58. A pharmaceutical composition comprising a composition of Compound I according to claim 52, and one or more pharmaceutical carriers.

59. The pharmaceutical composition according to claim 58 that is adapted for administration via a route selected from the group consisting of oral, parenteral, topical, transdermal, and pulmonary.

60. The pharmaceutical composition according to claim 58 that is in an oral dosage form selected from the group consisting of pills, tablets, capsules, emulsions, suspensions, microsuspensions, wafers, sprinkles, chewing gum, powders, lyophilized powders, granules, and troches.

61. The pharmaceutical composition according to claim 58, wherein the polymorphic form of the Compound I is at least partially preserved for a period of time following administration.

62. A composition comprising Compound I having the formula

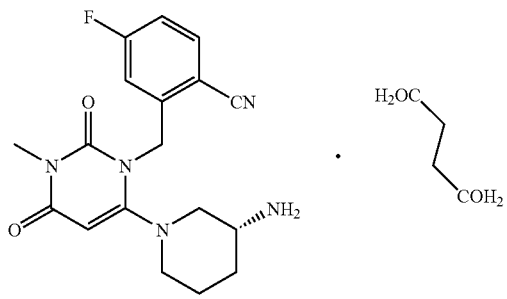

wherein a portion of Compound I is present as Amorphous Form, characterized by one or more physical properties selected from the group consisting of:
(i) an XRPD diffraction pattern (CuKα) characterized by a broad halo with no discernable diffraction peak; and
(ii) a glass transition temperature at about 82° C. and an exotherm at about 138° C.

63. The composition according to claim 62, wherein greater than 0.1% of Compound I (by weight) is present in the composition as Amorphous Form.

64. The composition according to claim 62, wherein greater than 1% of Compound I (by weight) is present in the composition as Amorphous Form.

65. The composition according to claim 62, wherein greater than 5% of Compound I (by weight) is present in the composition as Amorphous Form.

66. The composition according to claim 62, wherein greater than 10% of Compound I (by weight) is present in the composition as Amorphous Form.

67. The composition according to claim 62, wherein greater than 50% of Compound I (by weight) is present in the composition as Amorphous Form.

68. The composition according to claim 62, wherein greater than 75% of Compound I (by weight) is present in the composition as Amorphous Form.

69. The composition according to claim 62, wherein greater than 90% of Compound I (by weight) is present in the composition as Amorphous Form.

70. The composition according to claim 62, wherein greater than 95% of Compound I (by weight) is present in the composition as Amorphous Form.

71. The composition according to claim 62, wherein greater than 97% of Compound I (by weight) is present in the composition as Amorphous Form.

72. The composition according to claim 62, wherein greater than 99% of Compound I (by weight) is present in the composition as Amorphous Form.

73. A method for preparing a composition of Compound I according to claim 62 comprising: lyophilizing a water solution of Compound I.

74. A pharmaceutical composition comprising a composition of Compound I according to claim 62, and one or more pharmaceutical carriers.

75. The pharmaceutical composition according to claim 74 that is adapted for administration via a route selected from the group consisting of oral, parenteral, topical, transdermal, and pulmonary.

76. The pharmaceutical composition according to claim 74 that is in an oral dosage form selected from the group consisting of pills, tablets, capsules, emulsions, suspensions, microsuspensions, wafers, sprinkles, chewing gum, powders, lyophilized powders, granules, and troches.

77. The pharmaceutical composition according to claim 74, wherein the polymorphic form of the Compound I is at least partially preserved for a period of time following administration.

* * * * *